(12) United States Patent
Hansen et al.

(10) Patent No.: US 12,209,123 B2
(45) Date of Patent: *Jan. 28, 2025

(54) ANTIBODIES TO FELINE MCDONOUGH SARCOMA (FMS)-LIKE TYROSINE KINASE 3 RECEPTOR LIGAND (FLT3L) AND USES THEREOF FOR TREATING AUTOIMMUNE AND INFLAMMATORY DISEASES

(71) Applicant: Horizon Therapeutics Ireland DAC, Dublin (IE)

(72) Inventors: Anna Hansen, Dublin (IE); Xiaodong Xiao, Dublin (IE); Peter Pavlik, Dublin (IE); Yan Chen, Dublin (IE); Catherine Rachel Ettinger, Dublin (IE)

(73) Assignee: Horizon Therapeutics Ireland DAC (IE)

( * ) Notice: Subject to any disclaimer, the term of this patent is extended or adjusted under 35 U.S.C. 154(b) by 76 days.

This patent is subject to a terminal disclaimer.

(21) Appl. No.: 17/814,075

(22) Filed: Jul. 21, 2022

(65) Prior Publication Data

US 2023/0056815 A1 Feb. 23, 2023

Related U.S. Application Data

(63) Continuation of application No. 16/969,774, filed as application No. PCT/US2019/017877 on Feb. 13, 2019, now Pat. No. 11,512,127.

(60) Provisional application No. 62/630,571, filed on Feb. 14, 2018.

(51) Int. Cl.
*C07K 16/40* (2006.01)
*C07K 16/24* (2006.01)

(52) U.S. Cl.
CPC ........ *C07K 16/243* (2013.01); *C07K 2317/24* (2013.01); *C07K 2317/52* (2013.01); *C07K 2317/565* (2013.01); *C07K 2317/567* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,495,285 A | 1/1985 | Shimizu et al. | |
| 4,496,689 A | 1/1985 | Mitra | |
| 4,609,546 A | 9/1986 | Hiratani | |
| 4,640,835 A | 2/1987 | Shimizu et al. | |
| 4,670,417 A | 6/1987 | Iwasaki et al. | |
| 4,766,106 A | 8/1988 | Katre et al. | |
| 4,791,192 A | 12/1988 | Nakagawa et al. | |
| 4,816,567 A | 3/1989 | Cabilly et al. | |
| 4,946,778 A | 8/1990 | Ladner et al. | |
| 5,225,539 A | 7/1993 | Winter | |
| 5,530,101 A | 6/1996 | Queen et al. | |
| 5,545,806 A | 8/1996 | Lonberg et al. | |
| 5,545,807 A | 8/1996 | Surani et al. | |
| 5,554,512 A | 9/1996 | Lyman et al. | |
| 5,569,825 A | 10/1996 | Lonberg et al. | |
| 5,585,089 A | 12/1996 | Queen et al. | |
| 5,624,821 A | 4/1997 | Winter et al. | |
| 5,625,126 A | 4/1997 | Lonberg et al. | |
| 5,633,425 A | 5/1997 | Lonberg et al. | |
| 5,639,641 A | 6/1997 | Pedersen et al. | |
| 5,641,870 A | 6/1997 | Rinderknecht et al. | |
| 5,648,260 A | 7/1997 | Winter et al. | |
| 5,661,016 A | 8/1997 | Lonberg et al. | |
| 5,693,762 A | 12/1997 | Queen et al. | |
| 5,714,352 A | 2/1998 | Jakobovits | |
| 5,723,323 A | 3/1998 | Kauffman et al. | |
| 5,750,373 A | 5/1998 | Garrard et al. | |
| 5,763,192 A | 6/1998 | Kauffman et al. | |
| 5,766,886 A | 6/1998 | Studnicka et al. | |
| 5,814,476 A | 9/1998 | Kauffman et al. | |
| 5,817,483 A | 10/1998 | Kauffman et al. | |
| 5,824,514 A | 10/1998 | Kauffman et al. | |
| 5,885,793 A | 3/1999 | Griffiths et al. | |
| 5,955,358 A | 9/1999 | Huse | |
| 5,969,108 A | 10/1999 | Mccafferty et al. | |
| 5,976,862 A | 11/1999 | Kauffman et al. | |
| 6,172,197 B1 | 1/2001 | McCafferty et al. | |
| 6,180,370 B1 | 1/2001 | Queen et al. | |
| 6,204,023 B1 | 3/2001 | Robinson et al. | |
| 6,300,064 B1 | 10/2001 | Knappik et al. | |
| 6,331,431 B1 | 12/2001 | Glaser et al. | |
| 6,521,404 B1 | 2/2003 | Griffiths et al. | |
| 6,544,731 B1 | 4/2003 | Griffiths et al. | |
| 6,555,313 B1 | 4/2003 | Griffiths et al. | |
| 6,582,915 B1 | 6/2003 | Griffiths et al. | |

(Continued)

FOREIGN PATENT DOCUMENTS

EP 0229246 A2 7/1987
WO WO-8705330 A1 9/1987

(Continued)

OTHER PUBLICATIONS

Raglan et al., Int J Cancer. Oct. 1, 2019;145(7):1719-1730. doi: 10.1002/ijc.31961. Epub Feb. 20, 2019. PMID: 30387875.*
Gimbrone et al., Circ Res. Feb. 19, 2016;118(4):620-36. doi: 10.1161/CIRCRESAHA.115.306301. PMID: 26892962 PMCID: PMC4762052.*
Breijyeh et al., Molecules. Dec. 8, 2020;25(24):5789. doi: 10.3390/molecules25245789. PMID: 33302541 PMCID: PMC7764106.*
Kipriyanov et al., Mol Biotechnol. Jan. 2004;26(1):39-60. doi: 10.1385/MB:26:1:39. PMID: 14734823.*
Van Belle et al., J Autoimmun. Jun. 2010;34(4):445-52. doi: 10.1016/j.jaut.2009.11.010. Epub Dec. 9, 2009. PMID: 12490959 PMCID: PMC2803035.*

(Continued)

*Primary Examiner* — Michael Szperka

(57) ABSTRACT

Provided herein are anti-FLT3L antibodies and methods of using the antibodies to treat autoimmune and other inflammatory diseases.

19 Claims, 31 Drawing Sheets

Specification includes a Sequence Listing.

(56) References Cited

U.S. PATENT DOCUMENTS

| | | | |
|---|---|---|---|
| 6,593,081 | B1 | 7/2003 | Griffiths et al. |
| 6,602,994 | B1 | 8/2003 | Cash et al. |
| 6,653,068 | B2 | 11/2003 | Frisch et al. |
| 6,706,484 | B1 | 3/2004 | Knappik et al. |
| 7,083,784 | B2 | 8/2006 | Dall'Acqua et al. |
| 7,264,963 | B1 | 9/2007 | Knappik et al. |
| 7,342,110 | B2 | 3/2008 | Hoffee et al. |
| 7,537,932 | B1 | 5/2009 | Hannum et al. |
| 7,538,195 | B2 | 5/2009 | Singh et al. |
| 7,557,189 | B2 | 7/2009 | Hoffee et al. |
| 7,635,666 | B1 | 12/2009 | McCafferty et al. |
| 7,723,270 | B1 | 5/2010 | McCafferty et al. |
| 8,647,470 | B2 | 2/2014 | Esser |
| 11,512,127 | B2 * | 11/2022 | Hansen ............... A61P 37/02 |
| 2002/0160004 | A1 | 10/2002 | Lyman et al. |
| 2002/0160974 | A1 | 10/2002 | Banchereau et al. |
| 2005/0158313 | A1 | 7/2005 | Rosen |
| 2005/0261229 | A1 | 11/2005 | Gillies et al. |
| 2006/0142430 | A1 | 6/2006 | Harrington et al. |
| 2009/0263474 | A1 * | 10/2009 | Banchereau ........ A61P 19/00 435/7.1 |
| 2013/0156764 | A1 * | 6/2013 | Levis ............ A61K 31/7068 514/19.6 |
| 2014/0308201 | A1 | 10/2014 | Batt et al. |
| 2021/0002360 | A1 | 1/2021 | Hansen et al. |

FOREIGN PATENT DOCUMENTS

| | | |
|---|---|---|
| WO | WO-9014424 A1 | 11/1990 |
| WO | WO-9014430 A1 | 11/1990 |
| WO | WO-9014443 A1 | 11/1990 |
| WO | WO-9203461 A1 | 3/1992 |
| WO | WO-9306213 A1 | 4/1993 |
| WO | WO-9418219 A1 | 8/1994 |
| WO | WO-9906834 A2 | 2/1999 |
| WO | WO-02067760 A2 | 9/2002 |
| WO | WO-2006020145 A2 | 2/2006 |
| WO | WO-2009100309 A2 | 8/2009 |
| WO | WO-2011113041 A2 | 9/2011 |
| WO | 2016024255 | 2/2016 |
| WO | WO-2019160976 A1 | 8/2019 |

OTHER PUBLICATIONS

Al-Lazikani B., et al., "Standard Conformations for the Canonical Structures of Immunoglobulins," Journal of molecular biology, Nov. 1997, vol. 273 (4), pp. 927-948.

Altschul et al., "Gapped BLAST and PSI-BLAST: a new generation of protein database search programs," Nucleic Acids Research (1997) 25(17):3389-3402.

Altschul S.F., et al. "Local Alignment Statistics," Methods in Enzymology, 1996, vol. 266, pp. 460-480.

Andersson S.E.M., et al., "Activation of Fms-Like Tyrosine Kinase 3 Signaling Enhances Survivin Expression in a Mouse Model of Rheumatoid Arthritis," PLoS One, Oct. 17, 2012, vol. 7, No. 10, e47668, pp. 01-09.

Aplin J.D., et al., "Preparation, Properties, and Applications of Carbohydrate Conjugates of Proteins and Lipids," Critical Reviews Biochemistry, May 1981, vol. 10, No. 4, pp. 259-306.

Astier A.L., et al., "RNA Interference Screen in Primary Human T Cells Reveals FLT3 as a Modulator of IL-10 Levels," Journal of Immunology, 2010, vol. 184, No. 2, pp. 685-693.

Barbas C.F., et al., "In Vitro Evolution of a Neutralizing Human Antibody to Human Immunodeficiency Virus Type 1 to Enhance Affinity and Broaden Strain Cross-reactivity," Proceedings of the National Academy of Sciences, Apr. 1994, vol. 91 (9), pp. 3809-3813.

Boerner P., et al., "Production of Antigen-Specific Human Monoclonal Antibodies From in Vitro-primed Human Splenocytes," Journal of Immunology, Jul. 1991, vol. 147, No. 1, pp. 86-95.

Brennan M., et al., "Preparation of Bispecific Antibodies by Chemical Recombination of Monoclonal Immunoglobulin G1 Fragments," Science, Jul. 5, 1985, vol. 229, No. 4708, pp. 81-83.

Carter P., et al., "Humanization of an Anti-p185HER2 Antibody for Human Cancer Therapy," Proceedings of the National Academy of Sciences, May 1992, vol. 89 (10), pp. 4285-4289.

Chothia C., et al., "Canonical Structures for the Hypervariable Regions of Immunoglobulins," Journal of Molecular Biology, Aug. 20, 1987, vol. 196, No. 4, pp. 901-917.

Clackson T., et al., "Making Antibody Fragments Using Phage Display Libraries," Nature, Aug. 15, 1999, vol. 352, No. 6336, pp. 624-628.

Cole S.P.C., et al., "The EBV-Hybridoma Technique and its Application to Human Lung Cancer," Monoclonal Antibodies and Cancer Therapy, 1985, pp. 77-96.

Dall'Acqua W.F., et al., "Properties of Human IgG1s Engineered for Enhanced Binding to the Neonatal Fc Receptor (FcRn)," Journal of Biological Chemistry, Aug. 18, 2006, vol. 281, No. 33, pp. 23514-23524.

Deboy C.A., et al., "FLT-3 Expression and Function on Microglia in Multiple Sclerosis," Experimental and Molecular Pathology, Oct. 1, 2010, vol. 89, No. 2, pp. 109-116 (18 pages).

Edelman G.M., et al., "The Covalent Structure of an Entire GammaG Immunoglobulin Molecule," Biochemistry, Mar. 21, 1969, vol. 63, pp. 78-85.

Edge A.S.B., et al., "Deglycosylation of Glycoproteins by Trifluoromethanesulfonic Acid," Analytical Biochemistry, Nov. 15, 1981, vol. 118, No. 1, pp. 131-137.

Examination Report for Singapore Application No. 11202007702U, mailed Mar. 11, 2022, 5 pages.

Extended European Search Report for Application No. 19754925.6, mailed Oct. 19, 2021, 9 pages.

Fiore N., et al., "Immature Myeloid and Plasmacytoid Dendritic Cells Infiltrate Renal Tubulointerstitium in Patients with Lupus Nephritis," Molecular Immunology, Jan. 2008, vol. 45, No. 1, pp. 259-265.

Gram H., et al., "In Vitro Selection And Affinity Maturation Of Antibodies From A Naive Combinatorial Immunoglobulin Library," Proceedings of the National Academy of Sciences, Apr. 1992, vol. 89 (8), pp. 3576-3580.

Guimond M., et al., "In Vivo Role of Flt3 Ligand and Dendritic Cells in NK Cell Homeostasis," The Journal of Immunology, Mar. 15, 2010, vol. 184, No. 6, pp. 2769-2775.

Hansen A.M., et al., "Elucidation of FLT3 Ligand-dependent Dendritic Cell Activity In Autoimmune Disease," Presented at the 15th International Symposium on Dendritic Cells in Aachen, Germany, Jun. 10-14, 2018, 01 page.

Holdgate N., et al., "Recent Advances in Primary Sjogren's Syndrome [version 1; referees: 3 approved]," F1000Research, 2016, 5(F1000 Faculty Revision)-1412, 10 Pages.

Hoogenboom H.R., et al., "By-Passing Immunisation: Human Antibodies From Synthetic Repertoires of Germline VH Gene Segments Rearranged in Vitro," Journal of Molecular Biology, Sep. 20, 1992, vol. 227, No. 2, pp. 381-388.

Horizon Therapeutics Plc, Virtual R&D Day Presentation, Sep. 29, 2021, 118 pages.

Horizon Therapeutics Plc, Virtual R&D Day Remarks, Sep. 29, 2021, 24 pages.

Huse W.D., et al., "Generation of a Large Combinatorial Library of the Immunoglobulin Repertoire in Phage Lambda," Research Article, Dec. 8, 1989, vol. 246, pp. 1275-1281.

International Search Report for International Application No. PCT/US2019/017877, mailed Jun. 25, 2019, 05 Pages.

International Written Opinion for Application No. PCT/US2019/017877, mailed Jun. 25, 2019, 05 Pages.

Jones P.T., et al., "Replacing the Complementarity-Determining Regions in a Human Antibody with those from a Mouse," Nature, May 1986, vol. 321, pp. 522-525.

Karlin and Atschul, "Methods for assessing the statistical significance of molecular sequence features by using general scoring schemes," Proc. Natl. Acad. Sci. USA 87:2264-2268 (1990).

(56) References Cited

OTHER PUBLICATIONS

Karlin S., et al., "Applications And Statistics For Multiple High-scoring Segments In Molecular Sequences," Proceedings of National Academy of Sciences, Jun. 15, 1993, vol. 90, No. 12, pp. 5873-5877.
Kohler, G., et al., "Pillars Article: Continuous Cultures of Fused Cells Secreting Antibody of Predefined Specificity," Nature, Mar. 1975, vol. 256, No. 5517, pp. 495-497. The Journal of Immunology, Mar. 2005, 1:174(5):2453-2455.
Lemmon, M.A., et al., "Cell Signaling by Receptor Tyrosine Kinases", Cell, 2010, 141, 1117-1134.
Li X., et al., "Sniping the Scout: Targeting the Key Molecules in Dendritic Cell Functions for Treatment of Autoimmune Diseases," Pharmacological Research, May 2016, vol. 107, pp. 27-41, ISSN: 1043-6618, XP029533460, DOI: 10.1016/j.phrs.2016.02.023, Epub Feb. 27, 2016.
Lund J., et al., "Human Fc Gamma RI and Fc Gamma RII Interact with Distinct but Overlapping Sites on Human IgG," Journal of Immunology, Oct. 15, 1991, vol. 147, No. 8, pp. 2657-2662.
Mahmoud T.I., et al., "Autoimmune Manifestations in Aged Mice Arise from Early-Life Immune Dysregulation," Science Translational Medicine, Oct. 19, 2016, vol. 8, No. 361: 361ra137, 27 Pages.
Marks J.D., et al., "By-Passing Immunization: Building High Affinity Human Antibodies by Chain Shuffling," Nature Biotechnology, Jul. 1992, vol. 10 (7), pp. 779-783.
Marks J.D., et al., "By-Passing Immunization: Human Antibodies from V-gene Libraries Displayed on Phage," Journal of Molecular Biology, Dec. 1991, vol. 222, pp. 581-597.
McCafferty J., et al., "Phage Antibodies: Filamentous Phage Displaying Antibody Variable Domains," Nature, Dec. 1990, vol. 348 (6301), pp. 552-554.
Morgan A., et al., "The N-terminal End of the CH2 Domain of Chimeric Human IgG1 Anti-HLA-DR is Necessary for Clq, FcγRI and FcγRIII Binding," Immunology, Oct. 1995, vol. 86, No. 2, pp. 319-324.
Morimoto K., et al., "Single-step Purification of F(ab')2 Fragments of Mouse Monoclonal Antibodies (Immunoglobulins G1) by Hydrophobic Interaction High Performance Liquid Chromatography Using TSKgel Phenyl-5PW," Journal of Biochemical and Biophysical Methods, Mar. 1992, vol. 24, No. 1-2, pp. 107-117.
Notice of Allowance for U.S. Appl. No. 16/969,774, mailed Jul. 11, 2022, 5 pages.
Notice of Allowance for U.S. Appl. No. 16/969,774, mailed Jun. 16, 2022, 8 pages.
Oganesyan V., et al., "Structural Characterization of a Human Fc Fragment Engineered for Lack of Effector Functions," Acta Crystallographica Section D Biology Crystallography, May 14, 2008, vol. D64, pp. 700-704.
Palucka A.K., et al., "The Interplay of Dendritic Cell Subsets in Systemic Lupus Erythematosus", Immunology and Cell Biology, Oct. 2002, vol. 80, No. 5, pp. 484-488.
Presta L.G., et al., "Humanization of an Antibody Directed Against IgE," Journal of Immunology, Sep. 1, 1993, vol. 151, No. 5, pp. 2623-2632.
Ramos M.I., et al., "FMS-Related Tyrosine Kinase 3 Ligand (Flt3L)/CD135 Axis in Rheumatoid Arthritis," Arthritis Research and Therapy, 2013, vol. 15, No. R209, 13 pages.
Ramos M.I.P., et al., "Absence of Fms-like Tyrosine Kinase 3 Ligand (Flt3L) Signalling Protects Against Collagen-induced Arthritis," Annals of the Rheumatic Diseases, Jan. 2015, vol. 74 (1), pp. 211-219, XP055849443, GB ISSN: 0003-4967, DOI: 10.1136/annrheumdis-2013-203371, Epublished onSep. 24, 2013, [Retrieved on Oct. 8, 2013] Retrieved from URL: https://ard.bmj.com/content/annrheumdis/74/1/211.full.pdf?with-ds=yes.
Riechmann L., et al., "Reshaping Human Antibodies for Therapy," Nature, Mar. 1988, vol. 332, No. 24, pp. 323-327.

Robinson D.R., et al., "The Protein Tyrosine Kinase Family of The Human Genome," Oncogene, 2000, vol. 19, No. 49, pp. 5548-5557.
Rothe C., et al., "The Human Combinatorial Antibody Library HuCAL GOLD Combines Diversification of All Six CDRs According to the Natural Immune System with a Novel Display Method for Efficient Selection of High-Affinity Antibodies," Journal of Molecular Biology, Feb. 29, 2008, vol. 376, No. 4, pp. 1182-1200, DOI:0.1016/j.jmb.2007.12018.
Schier R., et al., "Isolation of Picomolar Affinity Anti-c-erbB-2 Single-Chain Fv by Molecular Evolution of the Complementarity Determining Regions in the Center of the Antibody Binding Site," Journal of Molecular Biology, Nov. 8, 1996, vol. 263, No. 4, pp. 551-567.
Search and Examination Report for Singapore Application No. 11202007702U, mailed Mar. 9, 2022, 2 pages.
Sheets M.D., et al., "Efficient Construction of a Large Nonimmune Phage Antibody Library: The Production of High-Affinity Human Single-Chain Antibodies to Protein Antigens," Proceedings of the National Academy of Sciences, USA, May 26, 1998, vol. 95 (11), pp. 6157-6162.
Sims M.J., et al., "A Humanized CD18 Antibody Can Block Function Without Cell Destruction," Journal of Immunology, Aug. 15, 1993, vol. 151, No. 4, pp. 2296-2308.
Sojar H.T., et al., "A Chemical Method for the Deglycosylation of Proteins," Archives of Biochemistry and Biophysics, Nov. 15, 1987, vol. 259, No. 1, pp. 52-57.
Stemmer W.P.C., "Rapid Evolution of a Protein in Vitro by DNA Shuffling," Nature, Aug. 4, 1994, vol. 370, No. 6488, pp. 389-391.
Thotakura N.R., et al., "Enzymatic Deglycosylation of Glycoproteins," Methods in Enzymology, 1987, vol. 138, pp. 350-359.
Tobon G.J., et al., "The Fms-Like Tyrosine Kinase 3 Ligand, a Mediator of B Cell Survival, is also a Marker of Lymphoma in Primary Sjogren's Syndrome," Arthritis and Rheumatism, Nov. 2010, vol. 62, No. 11, pp. 3447-3456.
"UniProtKB—P36888 (FLT3_Human)," UniProt Accession No. P36888, Jun. 1, 1994, 16 pages.
"UniProtKB—Q00342 (FLT3_Mouse)," UniProt Accession No. Q00342, Apr. 1, 1993, 14 pages.
"UniProtKB, Numero Accesion . A0A1F9WZN4_9BACT," Uncharacterized Protein, Feb. 15, 2017, 05 pages.
"UniProtKB, Numero Accesion. A0A1H6YLR2_9ACTN," Haloacetate dehalogenase, Nov. 22, 2017, 04 pages.
"UniProtKB, Numero Accesion. A0A1Q9DGW5_SYMMI," Multidrug Resistance Protein 1, Apr. 12, 2017, 09 pages.
Vaughan T.J., et al., "Human Antibodies with Sub-nanomolar Affinities Isolated from a Large Non-immunized Phage Display Library," Nature Biotechnology, 1996, vol. 14, pp. 309-314.
Verhoeyen M., et al., "Reshaping Human Antibodies: Grafting an Antilysozyme Activity," Science, Mar. 25, 1988, vol. 239, No. 4847, pp. 1534-1536.
Whartenby K.A., et al., "Inhibition of FL T3 signaling targets DCs to Ameliorate Autoimmune Disease," PNAS, Nov. 15, 2005, vol. 102, No. 46, pp. 16741-16746.
Xiao et al., "A High-Throughput Platform for Population Reformatting and Mammalian Expression of Phage Display Libraries To Enable Functional Screening as Full-Length IgG", mAbs, (2017) 9:6, :996-1006.
Xiao et al., "A Novel Dual Expression Platform for High Throughput Functional Screening of Phage Libraries in Product like Format", PLoS ONE (2015)10(10): e0140691, 16 pages.
Kazi et al., "FMS-Like tyrosine kinase 3/FLT3: From basic science to clinical implications," Physiological Reviews, Published: May 8, 2019, 99(3), pp. 1433-1466.
Wilson et al., "Dendritic cell Flt3—regulation, roles and repercussions for immunotherapy," Immunology & Cell Biology, Oct. 2021, (9), pp. 962-971.
Search Report issued to application No. CN201980013516.0, dated Mar. 28, 2024.

* cited by examiner

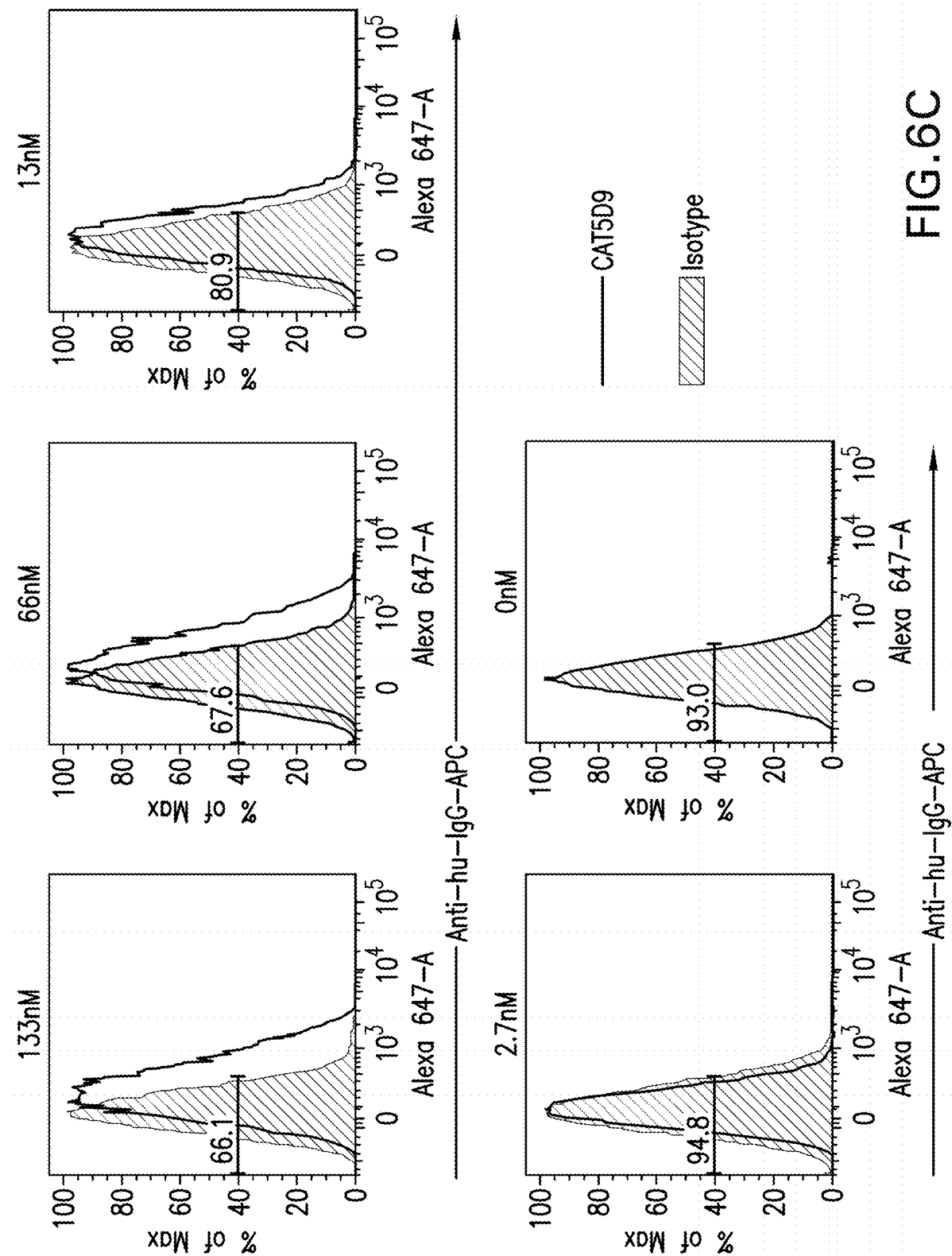

FIG. 14
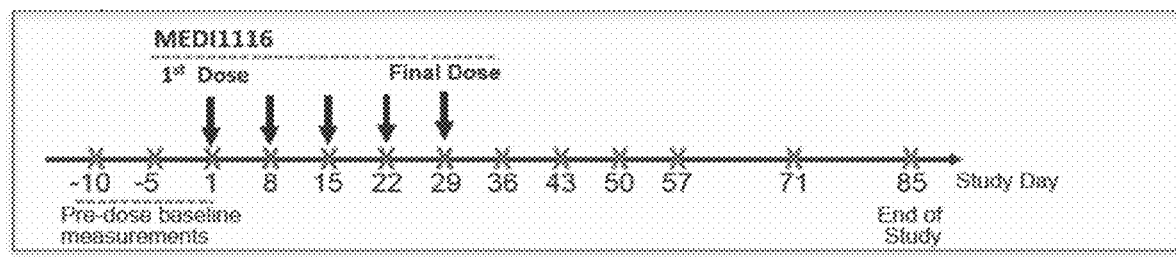
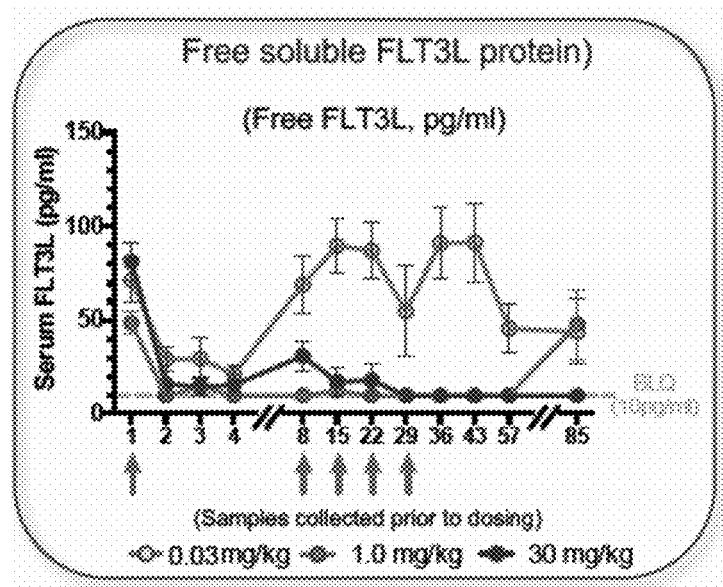
FIG. 15A

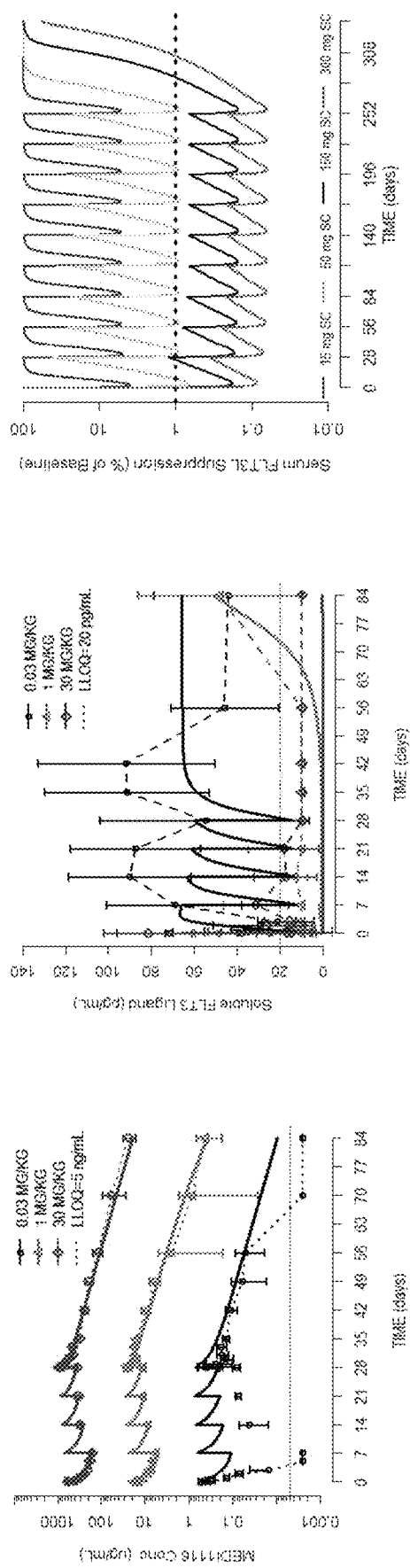

SEQUENCE LISTING

```
Sequence total quantity: 72
SEQ ID NO: 1              moltype = AA  length = 120
FEATURE                   Location/Qualifiers
REGION                    1..120
                          note = AM40_VH
source                    1..120
                          mol_type = protein
                          organism = synthetic construct
SEQUENCE: 1
QVQLVQSGAE VKKPGSSVKV SCKASGGTFS SYALSWVRQA PGQGLEWMGT RPPTSRTASY   60
AQKFQGRVTI TVDESTSTGY MELSSLRSED TAVYYCASND FVYGSYRFWG QGTTVTVSSA  120

SEQ ID NO: 2              moltype = AA  length = 111
FEATURE                   Location/Qualifiers
REGION                    1..111
                          note = AM40_VL
source                    1..111
                          mol_type = protein
                          organism = synthetic construct
SEQUENCE: 2
NFMLTQPHSV SESPGKTVTI SCTRTSGNIA GYFVQWYQQR PGSSPTTVIY EDYQRPSGVP   60
DRFSGSIDSS SNSASLTISG LKTEDEADYY CQSYDDYRRA AFGGGTKLTV L           111

SEQ ID NO: 3              moltype = AA  length = 119
FEATURE                   Location/Qualifiers
REGION                    1..119
                          note = SC4017_VH
source                    1..119
                          mol_type = protein
                          organism = synthetic construct
SEQUENCE: 3
QVQLVQSGAE VKKPGSSVKV SCKASGGTFS SYALSWVRQA PGQGLEWMGT RPPTSRTASY   60
AQKFQGRVTI TVDESTSTGY MELSSLRSED TAVYYCASND FVYGSYRFWG QGTTVTVSS   119

SEQ ID NO: 4              moltype = AA  length = 111
```

```
FEATURE                 Location/Qualifiers
REGION                  1..111
                        note = SC4017_VL
source                  1..111
                        mol_type = protein
                        organism = synthetic construct
SEQUENCE: 4
NFMLTQPHSV SESPGKTVTI SCTRTSGWIA GYFVQWYQQR PGSSPTTVIY EDYQRPSGVP    60
DRFSGSIDSS SNSASLTISG LKTEDEADYY CQSYDDYRRA AFGGGTKLTV L             111

SEQ ID NO: 5            moltype = AA  length = 119
FEATURE                 Location/Qualifiers
REGION                  1..119
                        note = CAT5D9_VH
source                  1..119
                        mol_type = protein
                        organism = synthetic construct
SEQUENCE: 5
QVQLVQSGAE VKKPGSSVKV SCKISGGTFS SYALSWVRQA PGQGLEWMGG IIPVFRTASY    60
AQKFQGRVTI TVDESASTGY IELSSLKSED TATYYCASNN YVVGSYRFWG QGTTVTVSS     119

SEQ ID NO: 6            moltype = AA  length = 111
FEATURE                 Location/Qualifiers
REGION                  1..111
                        note = CAT5D9_VL
source                  1..111
                        mol_type = protein
                        organism = synthetic construct
SEQUENCE: 6
NFMLTQPHSV SESPGKTVTI SCTRTSGNIA GYFVQWYQQR PGSSPTTVIY EDYQRPSGVP    60
DRFSGSIDRS SNSASLTISG LKPDDEADYY CQSYDDTSQG VFGAGTKVTV L             111

SEQ ID NO: 7            moltype = AA  length = 120
FEATURE                 Location/Qualifiers
REGION                  1..120
                        note = CAT8_VH
source                  1..120
                        mol_type = protein
                        organism = synthetic construct
SEQUENCE: 7
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARSS GYYGANFDFW GQGTTVTVSS    120

SEQ ID NO: 8            moltype = AA  length = 109
FEATURE                 Location/Qualifiers
REGION                  1..109
                        note = CAT8_VL
source                  1..109
                        mol_type = protein
                        organism = synthetic construct
SEQUENCE: 8
QSVLTQPPSA SGTPGQRVAI SCSGSSSNIG SGYVYWYQQV PGTAPTLLIH RNNQRPSGVP    60
DRFSGSKSGT SASLAISGLR SEDEADYYCA AWDDSLSGYV FGTGTKVTV                109

SEQ ID NO: 9            moltype = AA  length = 123
FEATURE                 Location/Qualifiers
REGION                  1..123
                        note = CAT26_VH
source                  1..123
                        mol_type = protein
                        organism = synthetic construct
SEQUENCE: 9
EVQLLESGGG LVQPGGSLRL SCAASGFTFS SYAVSWVRQA PGKGLEWVSA ISGSGGSTYY    60
ADSVKGRFTI SRDNSKNTLY LQMNSLRAED TAVYYCVKDA YGSSWYFYYF DYWGQGTMVT    120
VSS                                                                  123

SEQ ID NO: 10           moltype = AA  length = 110
FEATURE                 Location/Qualifiers
REGION                  1..110
                        note = CAT26_VL
source                  1..110
                        mol_type = protein
                        organism = synthetic construct
SEQUENCE: 10
QSVLTQPPSA SGTPGQRVTI SCSGSSSNIG INPVNWYQQL PGTAPKVLIY SDKYRPSGVA    60
DRFSGSKSGT SASLAISGLQ SEDEADYFCA AWDDSLNGRV FGTGTKLTVL               110

SEQ ID NO: 11           moltype = AA  length = 126
FEATURE                 Location/Qualifiers
```

```
REGION                    1..126
                          note = DYAX3_VH
source                    1..126
                          mol_type = protein
                          organism = synthetic construct
SEQUENCE: 11
EVQLLESGGG LVQPGGSLRL SCAASGFTFS MYEMRWVRQA PGKGLEWVSV IPSGGKTFYA    60
DSVKGRFTIS RDNSKNTLYL QMNSLRAEDT AVYYCARYSR WFGQLGFYSH YAMDVWSQGT   120
TVTVSS                                                              126

SEQ ID NO: 12             moltype = AA  length = 108
FEATURE                   Location/Qualifiers
REGION                    1..108
                          note = DYAX3_VL
source                    1..108
                          mol_type = protein
                          organism = synthetic construct
SEQUENCE: 12
DIQMTQSPSS LSASVGDRVA ITCRASQSID TYLNWYQQKP GKAPKLLIYA ASKLEDGVPS    60
RFSGSGTGTD FTLTIRSLQP EDFASYFCQQ SYSSPGITFG PGTKVEIK                108

SEQ ID NO: 13             moltype = AA  length = 127
FEATURE                   Location/Qualifiers
REGION                    1..127
                          note = DYAX5_VH
source                    1..127
                          mol_type = protein
                          organism = synthetic construct
SEQUENCE: 13
EVQLLESGGG LVQPGGSLRL SCAASGFTFS SYIMVWVRQA PGKGLEWVSS IYSSGGSTSY    60
ADSVKGRFTI SRDNSKNTLY LQMNSLRAED TAVYYCTRYS RWFGQLGFYS HYAMDVWSQG   120
TTVTVSS                                                             127

SEQ ID NO: 14             moltype = AA  length = 108
FEATURE                   Location/Qualifiers
REGION                    1..108
                          note = DYAX5_VL
source                    1..108
                          mol_type = protein
                          organism = synthetic construct
SEQUENCE: 14
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPWTFG QGTKVEIK                108

SEQ ID NO: 15             moltype = DNA  length = 360
FEATURE                   Location/Qualifiers
misc_feature              1..360
                          note = AM40_VH
source                    1..360
                          mol_type = other DNA
                          organism = synthetic construct
SEQUENCE: 15
caggtgcagc tggtgcagtc tggggctgag gtgaagaagc ctgggtcctc ggtgaaggtc    60
tcctgcaagg cttctggagg caccttcagc agttatgctc ttagctgggt gcgacaggcc   120
cctggacaag ggcttgagtg gatgggaacg cggccgcca cctcccggac agcaagctac    180
gcacagaaat tcagggcag agtcacgatt accgtggacg aatccacgag cacaggctac    240
atggagctga gcagcctgag atctgaggac acggccgtgt attactgtgc gtcaaacgac   300
ttcgtgtacg ggagttatcg tttctggggc caagggacca cggtcaccgt ctcctcagcg   360

SEQ ID NO: 16             moltype = DNA  length = 333
FEATURE                   Location/Qualifiers
misc_feature              1..333
                          note = AM40_VL
source                    1..333
                          mol_type = other DNA
                          organism = synthetic construct
SEQUENCE: 16
aattttatgc tgactcagcc ccactctgtg tcggagtctc cggggaagac ggtaaccatc    60
tcctgcaccc gcaccagtgg gaacattgcc ggctactttg tgcagtggta ccagcagcgc   120
ccggcagtt ccccaccac tgtgatctat gaggattacc aacgaccctc tggggtccct    180
gatcggttct ctggctccat cgacagctcc tccaactctg cctccctcac catctctgga   240
ctgaagactg aggacgaggc tgactactat tgtcagtctt atgatgacta ccggcgggcg   300
gcgttcggcg gagggaccaa gctgaccgtc cta                                333

SEQ ID NO: 17             moltype = DNA  length = 357
FEATURE                   Location/Qualifiers
misc_feature              1..357
                          note = SC4017_VH
source                    1..357
```

```
                              mol_type = other DNA
                              organism = synthetic construct
SEQUENCE: 17
caggtgcagc tggtgcagtc tggggctgag gtgaagaagc ctgggtcctc ggtgaaggtc    60
tcctgcaagg cttctggagg caccttcagc agttatgctc ttagctgggt gcgacaggcc   120
cctggacaag gcttgagtg gatgggaacg cggccgccga cctcccggac agcaagctac   180
gcacagaaat tcagggcag agtcacgatt accgtggacg aatccacgag cacaggctac    240
atggagctga gcagcctgag atctgaggac acggccgtgt attactgtgc gtcaaacgac   300
ttcgtgtacg gagttatcg tttctgggc aagggacca cggtcaccgt ctcctca         357

SEQ ID NO: 18              moltype = DNA  length = 333
FEATURE                    Location/Qualifiers
misc_feature               1..333
                              note = SC4017_VL
source                     1..333
                              mol_type = other DNA
                              organism = synthetic construct
SEQUENCE: 18
aattttatgc tgactcagcc ccactctgtg tcggagtctc ggggaagac ggtaaccatc     60
tcctgcaccc gcaccagtgg gtggattgcc ggctactttg tgcagtggta ccagcagcgc   120
ccgggcagtt cccccaccac tgtgatctat gaggattacc aacgaccctc tggggtccct   180
gatcggttct ctggctccat cgacagctcc tccaactctg cctccctcac catctctgga   240
ctgaagactg aggacggc tgactactat tgtcagtctt atgatgacta ccggcgggcg    300
gcgttcggcg gagggaccaa gctgaccgtc cta                                333

SEQ ID NO: 19              moltype = DNA  length = 357
FEATURE                    Location/Qualifiers
misc_feature               1..357
                              note = CAT5D9_VH
source                     1..357
                              mol_type = other DNA
                              organism = synthetic construct
SEQUENCE: 19
caggtgcagc tggtgcagtc tggggctgag gtgaagaagc ctgggtcctc ggtgaaggtc    60
tcctgcaaga tttctggagg caccttcagc agttatgctc ttagctgggt gcgacaggcc   120
cctggacaag gcttgagtg gatgggaggg atcatccctg tctttcggac agcaagctac    180
gcacagaaat tcagggcag agtcacgatt accgtggacg aatccgcgag cacaggctac    240
atagaactga gcagcctgaa atctgaggac acggccacat attactgtgc gtcaaataat    300
tacgtttggg ggagttatcg tttctgggc aggggacca cggtcaccgt ctcctca         357

SEQ ID NO: 20              moltype = DNA  length = 333
FEATURE                    Location/Qualifiers
misc_feature               1..333
                              note = CAT5D9_VL
source                     1..333
                              mol_type = other DNA
                              organism = synthetic construct
SEQUENCE: 20
aattttatgc tgactcagcc ccactctgtg tcggagtctc ggggaagac ggtcaccatc     60
tcctgcaccc gcaccagtgg gaacattgcc ggctactttg tgcagtggta ccagcagcgc   120
ccgggcagtt cccccaccac tgtgatctat gaggattacc aacgaccctc tggggtccct   180
gatcggttct ctggctccat cgacaggtcc tccaactctg cctccctcac catctctgga   240
ctgaagcctg acgacgaggc tgactactat tgtcagtctt atgatgacac ctctcaaggt   300
gtgttcggcg cagggaccaa ggtcaccgtc cta                                333

SEQ ID NO: 21              moltype = DNA  length = 360
FEATURE                    Location/Qualifiers
misc_feature               1..360
                              note = CAT8_VH
source                     1..360
                              mol_type = other DNA
                              organism = synthetic construct
SEQUENCE: 21
gaggtgcagc tgttggagtc tgggggaggc ttggtacagc ctgggggtc cctgagactc     60
tcctgtgcag cctctggatt cacctttagc agctatgcca tgagctgggt ccgccaggct   120
ccagggaagg gctggagtg gtctcagct attagtggta gtggtggtag cacatactac    180
gcagactccg tgaagggccg gttcaccatc tccagagaca attccaagaa cacgctgtat   240
ctgcaaatga acagcctgag agccgaggac acggccgtgt attactgtgc gagaagcagc   300
ggctactacg gggccaattt tgacttctgg ggcagggga ccacggtcac cgtctcgagt    360

SEQ ID NO: 22              moltype = DNA  length = 327
FEATURE                    Location/Qualifiers
misc_feature               1..327
                              note = CAT8_VL
source                     1..327
                              mol_type = other DNA
                              organism = synthetic construct
SEQUENCE: 22
cagtctgtgc tgacgcagcc gccctcagcg tccgggaccc ccgggcagag ggtcgccatc     60
```

```
tcttgttctg gaagcagctc aacatcgga agtggttatg tatactggta tcagcaggtc    120
ccaggaacgg ccccacact cctcatccat aggaataatc agcggccctc agggtccct     180
gaccgattct ctggctccaa gtctggcacc tcagcctccc tggccatcag tgggctccgg   240
tccgaggatg aggctgatta ttactgtgca gcgtgggatg acagcctgag tggttatgtc   300
ttcggaactg ggaccaaggt caccgtc                                       327

SEQ ID NO: 23              moltype = DNA   length = 369
FEATURE                    Location/Qualifiers
misc_feature               1..369
                           note = CAT26_VH
source                     1..369
                           mol_type = other DNA
                           organism = synthetic construct
SEQUENCE: 23
gaggtgcagc tgttggagtc tgggggaggc ttggtacagc ctgggggtc cctgagactc     60
tcctgtgcag cctctggatt cacctttagc agctatgccg tgagctgggt ccgccaggct   120
ccagggaagg ggctggagtg gtctcagct attagtggta gtggtggtag cacatactac    180
gcagactccg tgaagggccg gttcaccatc tccagagaca attccaagaa cacgctgtat   240
ctgcaaatga acagcctgag agccgaggac acggccgtgt attactgtgt gaaagacgca   300
tatggcagca gctggtactt ttactacttt gactactggg gccaagggac aatggtcacc    360
gtctcgagt                                                            369

SEQ ID NO: 24              moltype = DNA   length = 330
FEATURE                    Location/Qualifiers
misc_feature               1..330
                           note = CAT26_VL
source                     1..330
                           mol_type = other DNA
                           organism = synthetic construct
SEQUENCE: 24
cagtctgtgt tgacgcagcc gccttcagcg tctgggaccc ccgggcagag ggtcaccatc    60
tcttgttctg gaagcagctc aacatcgga atcaatcctg tgaactggta ccaacaactc    120
cccgaacgg ccccaaagt cctcatttat agtgataaat accggccctc aggggtcgct    180
gaccgcttct ctggctccaa gtctggaacc tcagcctccc tggccatcag tggcctccag   240
tctgaggatg aggctgatta cttctgtgca gcatgggatg acagcctgaa tggtcgcgtc   300
ttcggaactg ggaccaagct gaccgtccta                                    330

SEQ ID NO: 25              moltype = DNA   length = 378
FEATURE                    Location/Qualifiers
misc_feature               1..378
                           note = DYAX3_VH
source                     1..378
                           mol_type = other DNA
                           organism = synthetic construct
SEQUENCE: 25
gaagttcaat tgttagagtc tggtggcggt cttgttcagc ctggtggttc tttacgtctt    60
tcttgcgctg cttccggatt cacttttctc atgtacgaga tgtcgtgggt tcgccaagct   120
cctggtaaag gtttggagtg gtttctgtt atcccttctg gtggcaagac ttttatgct    180
gactccgtta aaggtcgctt cactatctct agagacaact ctaagaatac tctctacttg   240
cagatgaaca gcttaagggc tgaggacacg gccgtgtatt actgtgcgag atacagcaga   300
tggttcgggc agctagggtt ttactcccac tacgctatgg acgtctggag ccaagggacc   360
acggtcaccg tctcaagc                                                 378

SEQ ID NO: 26              moltype = DNA   length = 324
FEATURE                    Location/Qualifiers
misc_feature               1..324
                           note = DYAX3_VL
source                     1..324
                           mol_type = other DNA
                           organism = synthetic construct
SEQUENCE: 26
gacatccaga tgacccagtc tccatcctcc ctgtctgcat ctgtgggaga cagagtcgcc    60
atcacttgcc gcgcaagtca gagcatcgac acctatttaa attggtatca gcagaaacca   120
gggaaagccc ctaaactcct gatctatgct gcatccaagt tggaagacgg ggtcccatca   180
agattcagtg gcagtggaac tgggacagat ttcactctca ccatcagaag tctgcaacct   240
gaagatttg caagttattt ctgtcaacag agctactcta gtccagggat cactttcggc   300
cctgggacca aggtggagat caaa                                          324

SEQ ID NO: 27              moltype = DNA   length = 381
FEATURE                    Location/Qualifiers
misc_feature               1..381
                           note = DYAX5_VH
source                     1..381
                           mol_type = other DNA
                           organism = synthetic construct
SEQUENCE: 27
gaagttcaat tgttagagtc tggtggcggt cttgttcagc ctggtggttc tttacgtctt    60
tcttgcgctg cttccggatt cacttttctc tcttacatta tggtttgggt tcgccaagct   120
cctggtaaag gtttggagtg gtttcttctt atcattcttc tggtggctc tacttcttat    180
```

```
gctgactccg ttaaaggtcg cttcactatc tctagagaca actctaagaa tactctctac    240
ttgcagatga acagcttaag ggctgaggac acagccgtgt attactgtac gagatacagc    300
agatggttcg ggcagctagg gtttactcc cactacgcta tggacgtctg gagccaaggg    360
accacggtca ccgtctcaag c                                               381

SEQ ID NO: 28           moltype = DNA  length = 324
FEATURE                 Location/Qualifiers
misc_feature            1..324
                        note = DYAX5_VL
source                  1..324
                        mol_type = other DNA
                        organism = synthetic construct
SEQUENCE: 28
gacatccaga tgacccagtc tccatcctcc ctgtctgcat ctgtaggaga cagagtcacc     60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgtg gacgttcggc   300
caagggacca aggtggaaat caaa                                           324

SEQ ID NO: 29           moltype = AA  length = 5
FEATURE                 Location/Qualifiers
REGION                  1..5
                        note = AM40 and SC4017 and CAT5D9_HCDR1
source                  1..5
                        mol_type = protein
                        organism = synthetic construct
SEQUENCE: 29
SYALS                                                                  5

SEQ ID NO: 30           moltype = AA  length = 17
FEATURE                 Location/Qualifiers
REGION                  1..17
                        note = AM40 and SC4017_HCDR2
source                  1..17
                        mol_type = protein
                        organism = synthetic construct
SEQUENCE: 30
TRPPTSRTAS YAQKFQG                                                    17

SEQ ID NO: 31           moltype = AA  length = 10
FEATURE                 Location/Qualifiers
REGION                  1..10
                        note = AM40 and SC4017_HCDR3
source                  1..10
                        mol_type = protein
                        organism = synthetic construct
SEQUENCE: 31
NDFVYGSYRF                                                            10

SEQ ID NO: 32           moltype = AA  length = 13
FEATURE                 Location/Qualifiers
REGION                  1..13
                        note = AM40 and CAT5D9_LCDR1
source                  1..13
                        mol_type = protein
                        organism = synthetic construct
SEQUENCE: 32
TRTSGNIAGY FVQ                                                        13

SEQ ID NO: 33           moltype = AA  length = 7
FEATURE                 Location/Qualifiers
REGION                  1..7
                        note = AM40 and SC4017 and CAT5D9_LCDR2
source                  1..7
                        mol_type = protein
                        organism = synthetic construct
SEQUENCE: 33
EDYQRPS                                                                7

SEQ ID NO: 34           moltype = AA  length = 10
FEATURE                 Location/Qualifiers
REGION                  1..10
                        note = AM40 and SC4017_LCDR3
source                  1..10
                        mol_type = protein
                        organism = synthetic construct
SEQUENCE: 34
QSYDDYRRAA                                                            10
```

```
SEQ ID NO: 35            moltype = AA   length = 13
FEATURE                  Location/Qualifiers
REGION                   1..13
                         note = SC4017_LCDR1
source                   1..13
                         mol_type = protein
                         organism = synthetic construct
SEQUENCE: 35
TRTSGWIAGY FVQ                                                              13

SEQ ID NO: 36            moltype = AA   length = 17
FEATURE                  Location/Qualifiers
REGION                   1..17
                         note = CAT5D9_HCDR2
source                   1..17
                         mol_type = protein
                         organism = synthetic construct
SEQUENCE: 36
GIIPVFRTAS YAQKFQG                                                          17

SEQ ID NO: 37            moltype = AA   length = 10
FEATURE                  Location/Qualifiers
REGION                   1..10
                         note = CAT5D9_HCDR3
source                   1..10
                         mol_type = protein
                         organism = synthetic construct
SEQUENCE: 37
NNYVWGSYRF                                                                  10

SEQ ID NO: 38            moltype = AA   length = 10
FEATURE                  Location/Qualifiers
REGION                   1..10
                         note = CAT5D9_LCDR3
source                   1..10
                         mol_type = protein
                         organism = synthetic construct
SEQUENCE: 38
QSYDDTSQGV                                                                  10

SEQ ID NO: 39            moltype = AA   length = 5
FEATURE                  Location/Qualifiers
REGION                   1..5
                         note = CAT8_HCDR1
source                   1..5
                         mol_type = protein
                         organism = synthetic construct
SEQUENCE: 39
SYAMS                                                                        5

SEQ ID NO: 40            moltype = AA   length = 17
FEATURE                  Location/Qualifiers
REGION                   1..17
                         note = CAT8 and CAT26_HCDR2
source                   1..17
                         mol_type = protein
                         organism = synthetic construct
SEQUENCE: 40
AISGSGGSTY YADSVKG                                                          17

SEQ ID NO: 41            moltype = AA   length = 11
FEATURE                  Location/Qualifiers
REGION                   1..11
                         note = CAT8_HCDR3
source                   1..11
                         mol_type = protein
                         organism = synthetic construct
SEQUENCE: 41
SSGYYGANFD F                                                                11

SEQ ID NO: 42            moltype = AA   length = 13
FEATURE                  Location/Qualifiers
REGION                   1..13
                         note = CAT8_LCDR1
source                   1..13
                         mol_type = protein
                         organism = synthetic construct
SEQUENCE: 42
```

```
SGSSSNIGSG YVY                                                                   13

SEQ ID NO: 43          moltype = AA  length = 7
FEATURE                Location/Qualifiers
REGION                 1..7
                       note = CAT8_LCDR2
source                 1..7
                       mol_type = protein
                       organism = synthetic construct
SEQUENCE: 43
RNNQRPS                                                                           7

SEQ ID NO: 44          moltype = AA  length = 11
FEATURE                Location/Qualifiers
REGION                 1..11
                       note = CAT8_LCDR3
source                 1..11
                       mol_type = protein
                       organism = synthetic construct
SEQUENCE: 44
AAWDDSLSGY V                                                                     11

SEQ ID NO: 45          moltype = AA  length = 5
FEATURE                Location/Qualifiers
REGION                 1..5
                       note = CAT26_HCDR1
source                 1..5
                       mol_type = protein
                       organism = synthetic construct
SEQUENCE: 45
SYAVS                                                                             5

SEQ ID NO: 46          moltype = AA  length = 14
FEATURE                Location/Qualifiers
REGION                 1..14
                       note = CAT26_HCDR3
source                 1..14
                       mol_type = protein
                       organism = synthetic construct
SEQUENCE: 46
DAYGSSWYFY YFDY                                                                  14

SEQ ID NO: 47          moltype = AA  length = 13
FEATURE                Location/Qualifiers
REGION                 1..13
                       note = CAT26_LCDR1
source                 1..13
                       mol_type = protein
                       organism = synthetic construct
SEQUENCE: 47
SGSSSNIGIN PVN                                                                   13

SEQ ID NO: 48          moltype = AA  length = 7
FEATURE                Location/Qualifiers
REGION                 1..7
                       note = CAT26_LCDR2
source                 1..7
                       mol_type = protein
                       organism = synthetic construct
SEQUENCE: 48
SDKYRPS                                                                           7

SEQ ID NO: 49          moltype = AA  length = 11
FEATURE                Location/Qualifiers
REGION                 1..11
                       note = CAT26_LCDR3
source                 1..11
                       mol_type = protein
                       organism = synthetic construct
SEQUENCE: 49
AAWDDSLNGR V                                                                     11

SEQ ID NO: 50          moltype = AA  length = 5
FEATURE                Location/Qualifiers
REGION                 1..5
                       note = DYAX3_HCDR1
source                 1..5
                       mol_type = protein
                       organism = synthetic construct
```

```
SEQUENCE: 50
MYEMR                                                                      5

SEQ ID NO: 51           moltype = AA  length = 16
FEATURE                 Location/Qualifiers
REGION                  1..16
                        note = DYAX3_HCDR2
source                  1..16
                        mol_type = protein
                        organism = synthetic construct
SEQUENCE: 51
VIPSGGKTFY ADSVKG                                                         16

SEQ ID NO: 52           moltype = AA  length = 18
FEATURE                 Location/Qualifiers
REGION                  1..18
                        note = DYAX3 and DYAX5_HCDR3
source                  1..18
                        mol_type = protein
                        organism = synthetic construct
SEQUENCE: 52
YSRWFGQLGF YSHYAMDV                                                       18

SEQ ID NO: 53           moltype = AA  length = 11
FEATURE                 Location/Qualifiers
REGION                  1..11
                        note = DYAX3_LCDR1
source                  1..11
                        mol_type = protein
                        organism = synthetic construct
SEQUENCE: 53
RASQSIDTYL N                                                              11

SEQ ID NO: 54           moltype = AA  length = 7
FEATURE                 Location/Qualifiers
REGION                  1..7
                        note = DYAX3_LCDR2
source                  1..7
                        mol_type = protein
                        organism = synthetic construct
SEQUENCE: 54
AASKLED                                                                    7

SEQ ID NO: 55           moltype = AA  length = 10
FEATURE                 Location/Qualifiers
REGION                  1..10
                        note = DYAX3_LCDR3
source                  1..10
                        mol_type = protein
                        organism = synthetic construct
SEQUENCE: 55
QQSYSSPGIT                                                                10

SEQ ID NO: 56           moltype = AA  length = 5
FEATURE                 Location/Qualifiers
REGION                  1..5
                        note = DYAX5_HCDR1
source                  1..5
                        mol_type = protein
                        organism = synthetic construct
SEQUENCE: 56
SYIMV                                                                      5

SEQ ID NO: 57           moltype = AA  length = 17
FEATURE                 Location/Qualifiers
REGION                  1..17
                        note = DYAX5_HCDR2
source                  1..17
                        mol_type = protein
                        organism = synthetic construct
SEQUENCE: 57
SIYSSGGSTS YADSVKG                                                        17

SEQ ID NO: 58           moltype = AA  length = 11
FEATURE                 Location/Qualifiers
REGION                  1..11
                        note = DYAX5_LCDR1
source                  1..11
                        mol_type = protein
```

```
SEQUENCE: 58
RASQSISSYL N                                                                11

SEQ ID NO: 59           moltype = AA   length = 7
FEATURE                 Location/Qualifiers
REGION                  1..7
                        note = DYAX_LCDR2
source                  1..7
                        mol_type = protein
                        organism = synthetic construct
SEQUENCE: 59
AASSLQS                                                                     7

SEQ ID NO: 60           moltype = AA   length = 10
FEATURE                 Location/Qualifiers
REGION                  1..10
                        note = DYAX_LCDR3
source                  1..10
                        mol_type = protein
                        organism = synthetic construct
SEQUENCE: 60
QQSYSTPPWT                                                                 10

SEQ ID NO: 61           moltype = AA   length = 449
FEATURE                 Location/Qualifiers
REGION                  1..449
                        note = AM40_HC
source                  1..449
                        mol_type = protein
                        organism = synthetic construct
SEQUENCE: 61
QVQLVQSGAE  VKKPGSSVKV  SCKASGGTFS  SYALSWVRQA  PGQGLEWMGT  RPPTSRTASY   60
AQKFQGRVTI  TVDESTSTGY  MELSSLRSED  TAVYYCASND  FVYGSYRFWG  QGTTVTVSSA  120
STKGPSVFPL  APSSKSTSGG  TAALGCLVKD  YFPEPVTVSW  NSGALTSGVH  TFPAVLQSSG  180
LYSLSSVVTV  PSSSLGTQTY  ICNVNHKPSN  TKVDKRVEPK  SCDKTHTCPP  CPAPEFEGGP  240
SVFLFPPKPK  DTLMISRTPE  VTCVVVDVSH  EDPEVKFNWY  VDGVEVHNAK  TKPREEQYNS  300
TYRVVSVLTV  LHQDWLNGKE  YKCKVSNKAL  PASIEKTISK  AKGQPREPQV  YTLPPSREEM  360
TKNQVSLTCL  VKGFYPSDIA  VEWESNGQPE  NNYKTTPPVL  DSDGSFFLYS  KLTVDKSRWQ  420
QGNVFSCSVM  HEALHNHYTQ  KSLSLSPGK                                       449

SEQ ID NO: 62           moltype = AA   length = 217
FEATURE                 Location/Qualifiers
REGION                  1..217
                        note = AM40_LC
source                  1..217
                        mol_type = protein
                        organism = synthetic construct
SEQUENCE: 62
NFMLTQPHSV  SESPGKTVTI  SCTRTSGNIA  GYFVQWYQQR  PGSSPTTVIY  EDYQRPSGVP   60
DRFSGSIDSS  SNSASLTISG  LKTEDEADYY  CQSYDDYRRA  AFGGGTKLTV  LGQPKAAPSV  120
TLFPPSSEEL  QANKATLVCL  ISDFYPGAVT  VAWKADSSPV  KAGVETTTPS  KQSNNKYAAS  180
SYLSLTPEQW  KSHRSYSCQV  THEGSTVEKT  VAPTECS                             217

SEQ ID NO: 63           moltype = DNA   length = 1347
FEATURE                 Location/Qualifiers
misc_feature            1..1347
                        note = AM40_HC
source                  1..1347
                        mol_type = other DNA
                        organism = synthetic construct
SEQUENCE: 63
caggtgcagc tggtgcagtc tggggctgag gtgaagaagc ctgggtcctc ggtgaaggtc   60
tcctgcaagg cttctggagg caccttcagc agttatgctc ttagctgggt gcgacaggcc  120
cctggacaag gccttgagtg gatgggaacg cggccgccga cctcccggac agcaagtac   180
gcacagaaat tcagggcag agtcacgatt accgtggacg aatccacgag cacaggctac   240
atggagctga gcagcctgag atctgaggac acggccgtgt attactgtgc gtcaaacgac  300
ttcgtgtacg ggagttatcg tttctggggc caagggacca cggtcaccgt ctcctcagcg  360
tcgaccaagg gcccatccgt cttccccctg gcaccctcct ccaagagcac ctctgggggc  420
acagcggccc tgggctgcct ggtcaaggac tacttccccg aaccggtgac ggtgtcctgg  480
aactcaggcg ctctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaattcga ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagcctcca tcgagaaaac catctccaaa 1020
```

```
gccaaagggc agccccgaga accacaggtc tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcttaa gcctgtctcc gggtaaa                                       1347

SEQ ID NO: 64           moltype = DNA  length = 651
FEATURE                 Location/Qualifiers
misc_feature            1..651
                        note = AM40_LC
source                  1..651
                        mol_type = other DNA
                        organism = synthetic construct
SEQUENCE: 64
aattttatgc tgactcagcc ccactctgtg tcggagtctc cggggaagac ggtaaccatc    60
tcctgcaccc gcaccagtgg gaacattgcc ggctactttg tgcagtggta ccagcagcgc   120
ccgggcagtt cccccaccac tgtgatctat gaggattacc aacgaccctc tggggtccct   180
gatcggttct ctggctccat cgacagctcc tccaactctg cctccctcac catctctgga   240
ctgaagactg aggacgaggc tgactactat tgtcagtctt atgatgacta ccggcggggcg   300
gcgttcggcg gagggaccaa gctgaccgtc ctaggtcagc ccaaggcggc ccctcggtc    360
actctgttcc cgccctcctc tgaggagctt caagccacag gtgccacact ggtgtgtctc   420
ataagtgact tctacccggg agccgtgaca gtggcctgga aggcagatag cagccccgtc   480
aaggcgggag tggagaccac cacaccctcc aaacaaagca caacaagta cgcggccagc   540
agctacctga gcctgacgcc tgagcagtgg aagtcccaca gaagctacag ctgccaggtc   600
acgcatgaag ggagcaccgt ggagaagaca gtggccccta cagaatgttc a            651

SEQ ID NO: 65           moltype = AA  length = 449
FEATURE                 Location/Qualifiers
REGION                  1..449
                        note = SC4017_HC
source                  1..449
                        mol_type = protein
                        organism = synthetic construct
SEQUENCE: 65
QVQLVQSGAE VKKPGSSVKV SCKASGGTFS SYALSWVRQA PGQGLEWMGT RPPTSRTASY    60
AQKFQGRVTI TVDESTSTGY MELSSLRSED TAVYYCASND FVYGSYRFWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEFEGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PASIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 66           moltype = AA  length = 217
FEATURE                 Location/Qualifiers
REGION                  1..217
                        note = SC4017_LC
source                  1..217
                        mol_type = protein
                        organism = synthetic construct
SEQUENCE: 66
NFMLTQPHSV SESPGKTVTI SCTRTSGWIA GYFVQWYQQR PGSSPTTVIY EDYQRPSGVP    60
DRFSGSIDSS SNSASLTISG LKTEDEADYY CQSYDDYRRA AFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 67           moltype = DNA  length = 1486
FEATURE                 Location/Qualifiers
misc_feature            1..1486
                        note = SC4017_HC
source                  1..1486
                        mol_type = other DNA
                        organism = synthetic construct
SEQUENCE: 67
atgggatgga gctgtatcat cctcttcttg gtagcaacag ctacaggtaa ggggctcaca    60
gtagcaggct tgaggtctag acatatatat gggtgacaat gacatccact ttgcctttct   120
ctccacaggt gtacactccc aggtgcagct ggtgcagtct ggggctgagg tgaagaagcc   180
tggggtcctcg gtgaaggtct cctgcaaggc ttctggagga accttcagca gttatgctct   240
tagctgggtg cgacaggccc tggacaagg gcttgagtgg atgggaacgc ggccgccgac   300
ctcccggaca gcaagctacg cacagaaatt cagggcaga gtcacgatta ccgtggacga   360
atccacgagc acaggctaca tggagctgag cagcctgaga tctgaggaca cggccgtgta   420
ttactgtgcg tcaaacgact tcgtgtacgg gagttatcgt ttctgggccc aagggaccac   480
ggtcaccgtc tcctcagcta cgaccaaggg cccatccgtc ttcccctcg cacccctcc   540
caagagcacc tctgggggca gcggccctg ggctgcctg tcaaggact acttccccga   600
accggtgacg gtgtcctgga actcaggcgc tctgaccagc ggcgtgcaca ccttcccggc   660
tgtcctacag tcctcaggac tctactccct cagcagcgtg gtgaccgtgc cctcagcag   720
cttgggcacc cagacctaca tctgcaacgt gaatcacaag cccagcaaca ccaaggtgga   780
caagagagtt gagcccaaat cttgtgacaa aactcacaca tgcccaccgt gcccagcacc   840
```

```
tgaattcgag gggggaccgt cagtcttcct cttcccccca aaacccaagg acaccctcat   900
gatctcccgg accectgagg tcacatgcgt ggtggtggac gtgagccacg aagaccctga   960
ggtcaagttc aactggtacg tggacggcgt ggaggtgcat aatgccaaga caaagccgcg  1020
ggaggagcag tacaacagca cgtaccgtgt ggtcagcgtc ctcaccgtcc tgcaccagga  1080
ctggctgaat ggcaaggagt acaagtgcaa ggtctccaac aaagccctcc cagcctccat  1140
cgagaaaacc atctccaaag ccaaagggca gccccgagaa ccacaggtct acaccctgcc  1200
cccatcccgg gaggagatga ccaagaacca ggtcagcctg acctgcctgg tcaaaggctt  1260
ctatcccagc gacatcgccg tggagtggga gagcaatggg cagccggaga caactacaa   1320
gaccacgcct cccgtgctgg actccgacgg ctccttcttc ctctatagca agctcaccgt  1380
ggacaagagc aggtggcagc aggggaacgt cttctcatgc tccgtgatgc atgaggctct  1440
gcacaaccac tacacgcaga agagcttaag cctgtctccg ggtaaa                 1486

SEQ ID NO: 68           moltype = DNA  length = 651
FEATURE                 Location/Qualifiers
misc_feature            1..651
                        note = SC4017_LC
source                  1..651
                        mol_type = other DNA
                        organism = synthetic construct
SEQUENCE: 68
aattttatgc tgactcagcc ccactctgtg tcggagtctc cggggaagac ggtaaccatc    60
tcctgcaccc gcaccagtgg gtggattgcc ggctactttg tgcagtggta ccagcagcgc   120
ccgggcagtt cccccaccac tgtgatctat gaggattacc aacgaccctc tggggtcect   180
gatcggttct ctggctccat cgacagctcc tccaactctg cctccctcac catctctgga   240
ctgaagactg aggacgaggc tgactactat tgtcagtctt atgatgacta ccggcggcg    300
gcgttcggcg gagggaccaa gctgaccgtc ctaggtcagc ccaaggcggc cccctcggtc   360
actctgttcc cgccctcctc tgaggagctt caagccaaca aggccacact ggtgtgtctc   420
ataagtgact tctaccggg agccgtgaca gtggcctgga aggcagatag cagccccgtc    480
aaggcgggag tggagaccac cacaccctcc aaacaaagca caacaagta cgcggccagc    540
agctacctga gcctgacgcc tgagcagtgg aagtcccaca gaagctacag ctgccaggtc   600
acgcatgaag ggagcaccgt ggagaagaca gtggccccta cagaatgttc a            651

SEQ ID NO: 69           moltype = AA  length = 449
FEATURE                 Location/Qualifiers
REGION                  1..449
                        note = CAT5D9_HC
source                  1..449
                        mol_type = protein
                        organism = synthetic construct
SEQUENCE: 69
QVQLVQSGAE VKKPGSSVKV SCKISGGTFS SYALSWVRQA PGQGLEWMGG IIPVFRTASY    60
AQKFQGRVTI TVDESASTGY IELSSLKSED TATYYCASNN YVWGSYRFWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEFEGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PASIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 70           moltype = AA  length = 217
FEATURE                 Location/Qualifiers
REGION                  1..217
                        note = CAT5D9_LC
source                  1..217
                        mol_type = protein
                        organism = synthetic construct
SEQUENCE: 70
NFMLTQPHSV SESPGKTVTI SCTRTSGNIA GYFVQWYQQR PGSSPTTVIY EDYQRPSGVP    60
DRFSGSIDRS SNSASLTISG LKPDDEADYY CQSYDDTSQG VFGAGTKVTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 71           moltype = DNA  length = 1346
FEATURE                 Location/Qualifiers
misc_feature            1..1346
                        note = CAT5D9_HC
source                  1..1346
                        mol_type = other DNA
                        organism = synthetic construct
SEQUENCE: 71
aggtgcagct ggtgcagtct ggggctgagg tgaagaagcc tggtcctcg gtgaaggtct     60
cctgcaaggc ttctggaggc accttcagca gttatgctct tagctgggtg cgacaggccc   120
ctggacaagg gcttgagtgg atgggaacgc ggccgccgac ctcccggaca gcaagctacg   180
cacagaaatt tcagggcaga gtcacgatta ccgtggacga atccgccagc acaggctaca   240
tggagctgag cagcctgaga tctgaggaca cggccgtgta ttactgtgcg tcaaacgact   300
tcgtgtacgg gagttatcgt ttctggggcc aagggaccac ggtcaccgtc tcctcagcgt   360
cgaccaaggg cccatccgtc ttccccctgg caccctcctc caagagcacc tctggggca   420
cagcggccct gggctgcctg gtcaaggact acttccccga accggtgacg gtgtcctgga   480
actcaggcgc tctgaccagc ggcgtgcaca ccttcccggc tgtcctacag tcctcaggac   540
```

```
                                -continued
tctactccct cagcagcgtg gtgaccgtgc cctccagcag cttgggcacc cagacctaca   600
tctgcaacgt gaatcacaag cccagcaaca ccaaggtgga caagagagtt gagcccaaat   660
cttgtgacaa aactcacaca tgcccaccgt gcccagcacc tgaattcgag ggggaccgt   720
cagtcttcct cttcccccca aaacccaagg acaccctcat gatctcccgg acccctgagg   780
tcacatgcgt ggtggtggac gtgagccacg aagaccctga ggtcaagttc aactggtacg   840
tggacggcgt ggaggtgcat aatgccaaga caaagccgcg ggaggagcag tacaacagca   900
cgtaccgtgt ggtcagcgtc ctcaccgtcc tgcaccagga ctggctgaat ggcaaggagt   960
acaagtgcaa ggtctccaac aaagccctcc cagcctccat cgagaaaacc atctccaaag  1020
ccaaagggca gccccgagaa ccacaggtct acaccctgcc cccatcccgg gaggagatga  1080
ccaagaacca ggtcagcctg acctgcctgg tcaaaggctt ctatcccagc gacatcgccg  1140
tggagtggga gagcaatggg cagccggaga acaactacaa gaccacgcct cccgtgctgg  1200
actccgacgg ctccttcttc ctctatagca agctcaccgt ggacaagagc aggtggcagc  1260
aggggaacgt cttctcatgc tccgtgatgc atgaggctct gcacaaccac tacacgcaga  1320
agagcttaag cctgtctccg ggtaaa                                      1346

SEQ ID NO: 72         moltype = DNA  length = 651
FEATURE               Location/Qualifiers
misc_feature          1..651
                      note = CAT5D9_LC
source                1..651
                      mol_type = other DNA
                      organism = synthetic construct
SEQUENCE: 72
aattttatgc tgactcagcc ccactctgtg tcggagtctc cggggaagac ggtcaccatc    60
tcctgcaccc gcaccagtgg gaacattgcc ggctactttg tgcagtggta ccagcagcgc   120
ccgggcagtt cccccaccac tgtgatctat gaggattacc aacgaccctc tggggtccct   180
gatcggttct ctggctccat cgacaggtcc tccaactctg cctccctcac catctctgga   240
ctgaagcctg acgacgaggc tgactactat tgtcagtctt atgatgacac ctctcaaggt   300
gtgttcggcg cagggaccaa ggtcaccgtc ctaggtcagc ccaaggcggc cccctcggtc   360
actctgttcc cgccctcctc tgaggagctt caagccaaca aggccacact ggtgtgtctc   420
ataagtgact tctacccggg agccgtgaca gtggcctgga aggcagatag cagcccgtc   480
aaggcgggag tggagaccac cacaccctcc aaacaaagca acaacaagta cgcggccagc   540
agctacctga gcctgacgcc tgagcagtgg aagtcccaca gaagctacag ctgccaggtc   600
acgcatgaag ggagcaccgt ggagaagaca gtggccccta cagaatgttc a            651
```

ANTIBODIES TO FELINE MCDONOUGH SARCOMA (FMS)-LIKE TYROSINE KINASE 3 RECEPTOR LIGAND (FLT3L) AND USES THEREOF FOR TREATING AUTOIMMUNE AND INFLAMMATORY DISEASES

CROSS-REFERENCE

This application is the U.S. continuation of U.S. application Ser. No. 16/969,774, filed Aug. 13, 2020, which claims the benefit of priority to U.S. National Stage Application under 35 U.S.C. § 371 of International PCT US2019/017877, filed on Feb. 13, 2019, which claims priority to and benefit from U.S. Provisional Application No. 62/630,571, filed on Feb. 14, 2018, the entire contents of each of which are herein incorporated by reference.

REFERENCE TO AN ELECTRONIC SEQUENCE LISTING

The contents of the electronic sequence listing (HOPA_015_02US_SeqList_ST26.xml; Size: 104,706 bytes) is herein incorporated by reference in its entirety.

BACKGROUND

Autoimmune diseases, which occur when the body's immune system produces autoantibodies, are unfortunately common. For example, it is estimated that over 23 million Americans are affected by an autoimmune disease. There are currently more than 80 recognized autoimmune diseases. Specific examples of autoimmune diseases include systemic lupus erythematosus, myositis, primary Sjögren's Syndrome, multiple sclerosis, uveitis, psoriasis, and rheumatoid arthritis.

Systemic lupus erythematosus (SLE) is characterized by painful joints, swollen lymph nodes and a butterfly rash on the cheeks. In SLE, autoantibodies against healthy tissues attack a patient's immune system resulting in inflammation. At the cellular level, SLE patients have autoreactive T and B cells, driven by dendritic cells (Palucka A. K. et al. *Immunology and Cell Biology* (2002) 80: 484-488). Sjögren's Syndrome is characterized by systemic chronic inflammation of the exocrine organs resulting in organ dysfunction (Holdgate N. and St. Clair E. W., *F1000 Research*. 1412 10.12688/f1000research.8352.1).

Multiple sclerosis (MS) is characterized by demyelination of nerve cells in the brain and spinal cord and central nervous system (CNS) inflammation. Psoriasis is an autoimmune disease that presents as patches of red, itchy skin. Rheumatoid arthritis (RA) is an inflammatory disorder of joint synovial tissue characterized by persistent synovitis and destruction of the cartilage and bone in the joint. The damage can progress to impact numerous body systems. Lupus nephritis, is associated with systemic lupus erythematous and results in kidney inflammation. When inflamed the kidneys leak protein and can eventually fail. Uveitis is a group of inflammatory diseases that attack, and can destroy eye tissues leading to vision loss.

In addition, acute and chronic pro-inflammatory states have been associated with and may be causal in myriad diseases in individuals. Specific examples of diseases believed to be associated with chronic inflammation including Type 1 and Type 2 diabetes, chronic kidney disease (CKD), including, for example, CKD caused by diabetes, diabetic nephropathy, and high blood pressure; atherosclerosis, Alzheimer's disease, cancer, and associated complications of such diseases, including heart disease, hypertension, anemia, pericarditis, renal osteodystrophy, and others. Like autoimmune diseases, in diseases associated with chronic inflammation, the body appears to be mounting an excessive, continuous proinflammatory response, which can lead to debilitating and often lethal comorbidities.

The causes of autoimmune diseases are not well understood. Mechanistically, underlying every autoimmune disease is an ongoing autoimmune response that is promoted (and/or not inhibited) by complex regulatory systems that continuously replenish autoreactive immune cells. A similar mechanism appears to be at work in non-autoimmune chronic inflammatory diseases. For this reason, therapeutic interventions in autoimmune diseases and for chronic inflammation have targeted myriad regulatory systems, signaling cascades, and their constituent components.

One class of putative therapeutic targets includes tyrosine kinase receptors (TKRs), which are transmembrane receptors that bind distinct growth factors and proteins to regulate cellular homeostasis. Over fifty known human TKRs are divided into 20 distinct classes defined by their genetic phylogeny (Robins D. R., et al. *Oncogene*. (2000) 19: 5548-5557; Lemmon M. A., and Schlessinger J. *Cell*. (2010) 141: 1117-1134). TKR class III is characterized by the presence of five to seven immunoglobulin-like domains in the extracellular section containing 70 to 100 hydrophilic residues. Within class III TKRs, Feline McDonough Sarcoma (FMS)-like tyrosine kinase 3 receptor (FLT3) is a membrane bound receptor expressed on human stem cells, hematopoietic cell precursors, dendritic cells, activated T and B cells, monocytes, and microglia. FLT3 binds FLT3 ligand (FLT3L), a hematopoietic cytokine expressed by multiple cell types including activated T cells, activated endothelium, and bone marrow stromal cells. FLT3L is expressed as both a cell surface and secreted homodimer and signals through its cognate receptor, FLT3. FLT3 is expressed on the cell surface as a monomer and is activated upon ligation with FLT3L. Upon FLT3L ligation, FLT3 dimerizes, autophosphorylates, and activates signaling pathways including the RAS/extracellular signal-regulated kinase (ERK), phosphatidylinositide 3-kinase (PI3K) and signal transducer and activator of transcription (STAT) 3 and 5. Following auto-phosphorylation, dimerized FLT3 is internalized and degraded.

FLT3L is produced in response to inflammatory signals, particularly the D-chain cytokines: IL-2, IL-7 and IL-15, and its interaction with FLT3 drives the inflammatory process primarily through it role in the differentiation, proliferation, and survival of DCs. There is also a putative role for FLT3 signalling in T and B cell survival after activation, with both cell types reported to transiently upregulate the receptor (Astier A L et al., *J. Immunology*. 2010 v184: 685-93 and Tobon et al. *Arthritis & Rheumatism*. 2010; 62(11): 3447-56). In addition, NK cell survival is thought to be indirectly dependent on FLT3L via its requirement for IL-15 derived from DCs, although this observation is based on mouse data (Guimond M et al., *J. Immunology* 2010; 184: 2769-75) and has yet to be demonstrated in humans.

DCs are of particular interest in inflammation as they are the sentinels of the immune system, migrating from the site of inflammation to the lymph node and initiating the adaptive immune response that is ultimately required to generate autoimmune disease. Broadly, there are two subsets of DC: Myeloid/classical dendritic cells (cDCs) and plasmacytoid dendritic cells (pDCs). cDCs produce inflammatory cytokines (e.g., IFNI-III, IL-23, IL-12, IL-6, and IL-1 □), present antigen to T cells in the context of co-stimulation, and secret chemokines that recruit cells to the site of inflammation and ensure they co-localize as required for critical cell-cell interactions. Through these mechanisms cDCs stimulate neutrophils, B-cells, T-cells, and NK cells resulting in NETosis, autoantibody production, IL-17 production, and additional inflammatory cytokine production. pDCs are the primary source of type I IFN, a key cytokine in the innate response that enhances activation of all arms of the immune system.

Salivary glands from Sjögren's Syndrome patients exhibit FLT3 and FLT3L expression on infiltrating B-cells (Tobon et al. *Arthritis & Rheumatism*. (2010) 62(11): 3447-3456). In addition, Sjögren's Syndrome patients exhibit increased frequency of FLT3 expressing B-cells in the circulation and their survival is enhanced when co-cultured with FLT3L-expressing human salivary cells. Individuals with MS express FLT3 protein in chronic and active lesions as well as grey and white matter (DeBoy C. A. et al. *Exp Mol Pathol*. (2010); 89(2): 109-116). Further, FLT3 is co-localized with immature DCs in perivascular brain indicating infiltration of FLT3 positive DCs into the brains of individuals with MS (Deboy et al.). In RA, synovial fluid FLT3L levels are increased compared to healthy individuals. In addition, monocytes, NK cells, and DCs from RA patients express high levels of FLT3L (Ramos M. et al. *Arthritis Res Ther*. (2013) 15(6): R209).

Moreover, increased serum and inflammatory site FLT3L levels have been reported for SLE, myositis, primary Sjögren's Syndrome, MS, uveitis, and RA (Andersson et al. *PLoS One* (2012) 7: e47668; DeBoy et al. *Exp andMol Path* (2010) 89: 109-16).

Therefore, while FLT3-mediated pro-inflammatory survival (e.g., via pDCs and mDCs) is an advantageous physiological response in healthy individuals, it likely has deleterious effects in autoimmune diseases. Thus, disruption or attenuation of the FLT3/FLT3L signaling pathway could prove to be an important tool for combatting autoimmune diseases and other inflammatory diseases as well as for reducing inflammation.

SUMMARY OF THE INVENTION

Provided herein are novel FLT3L binding antibodies for controlling autoimmune diseases and other acute and/or chronic inflammatory diseases.

In a first aspect, the disclosure provides an isolated antibody or antigen-binding fragment thereof that specifically binds to FLT3L, comprising a set of Complementarity-Determining Regions (CDRs): HCDR1, HCDR2, HCDR3, LCDR1, LCDR2, and LCDR3 wherein the HCDR1, HCDR2, HCDR3, LCDR1, LCDR2, and LCDR3 comprise the amino acid sequences of: (a) SEQ ID NOs: 29, 30, 31, 32, 33, and 34, respectively; or (b) SEQ ID NOs: 29, 30, 31, 35, 33, and 34, respectively; or (c) SEQ ID Nos: 29, 36, 37, 32, 33, and 38, respectively.

In one embodiment of the first aspect, the isolated antibody or antigen-binding fragment thereof includes a heavy chain variable region (VH) and light chain variable region (VL) having at least 95%, 96%, 97%, 98%, or 99% sequence identity to: (a) SEQ ID NO: 1 and SEQ ID NO: 2, respectively; or (b) SEQ ID NO: 3 and SEQ ID NO: 4, respectively; or (c) SEQ ID NO: 5 and SEQ ID NO: 6, respectively. In another embodiment, the VH and VL include (a) SEQ ID NO: 1 and SEQ ID NO: 2, respectively; or (b) SEQ ID NO: 3 and SEQ ID NO: 4, respectively; or (c) SEQ ID NO: 5 and SEQ ID NO: 6, respectively. In a further embodiment, the isolated antibody or antigen-binding fragment include (a) a heavy chain region comprising SEQ ID NO: 61 and a light chain region comprising SEQ ID NO: 62; or (b) a heavy chain region comprising SEQ ID NO: 65 and a light chain region comprising SEQ ID NO: 66; or (c) a heavy chain region comprising SEQ ID NO: 69 and a light chain region comprising SEQ ID NO: 70. In one embodiment, the isolated antibody or antigen-binding fragment thereof inhibits FLT3L-mediated activation of FLT3. In another embodiment, the isolated antibody or antigen-binding fragment thereof does not cross-react with structurally similar TKR ligand molecules. In one embodiment, the isolated antibody or antigen-binding fragment thereof does not cross-react with at least one of huSCF and huCSF1. In a further embodiment, the isolated antibody or antigen-binding fragment thereof does not cross-react with either huSCF or huCSF1. In one embodiment, the isolated antibody or antigen-binding fragment thereof is a monoclonal antibody, a recombinant antibody, a human antibody, a humanized antibody, or a chimeric antibody. In one embodiment, the isolated antibody or antigen-binding fragment comprises a heavy chain immunoglobulin constant domain selected from the group consisting of: (a) an IgA constant domain; (b) an IgD constant domain; (c) an IgE constant domain; (d) an IgG1 constant domain; (e) an IgG2 constant domain; (f) an IgG3 constant domain; (g) an IgG4 constant domain; and (h) an IgM constant domain. In one embodiment, the isolated antibody or antigen-binding fragment comprises an IgG1 constant domain. In another embodiment, the isolated antibody or antigen-binding fragment comprises a light chain immunoglobulin constant domain selected from the group consisting of: (a) an Ig kappa constant domain; and (b) an Ig lambda constant domain. In one embodiment, the antigen binding protein comprises a human IgG1 constant domain and a human lambda constant domain. In one embodiment, the IgG1 constant domain comprises one or more amino acid substitutions selected from the group consisting of L234F, L235E and P33IS, numbered according to the EU numbering index of Kabat (Edelman et al., *Proc. Natl. Acad. Sci.*, 63:78-85 (1969)).

In a second aspect, the disclosure provides an isolated nucleic acid molecule encoding the isolated antibody or antigen-binding fragment thereof according to the first aspect and/or embodiments thereof. In one embodiment of the second aspect, the nucleic acid molecule is operably linked to a control sequence.

In a third aspect, the disclosure provides a vector comprising the nucleic acid molecule according to the second aspect and/or embodiments thereof.

In a fourth aspect, the disclosure provides a host cell transformed with the nucleic acid of molecule according to the second aspect and/or embodiments thereof or the vector according to the third aspect. In one embodiment, the host cell is a mammalian host cell. In another embodiment, the host cell is a HEK293 cell, an NS0 murine myeloma cell, or a Chinese hamster ovary (CHO) cell.

In a fifth aspect, the disclosure provides a hybridoma producing the antibody or antigen-binding fragment of any of the preceding aspects or embodiments thereof.

In a sixth aspect, the disclosure provides an isolated host cell producing the antibody or antigen-binding fragment of any of the preceding aspects or embodiments thereof.

In a seventh aspect, the disclosure provides a method of making the antibody or antigen-binding fragment thereof according to any of the preceding aspects or embodiments thereof, comprising (a) culturing a host cell expressing said antibody or antigen-binding fragment or culturing the host cell of the third aspect or embodiment thereof or the hybridoma according to the fourth aspect; and (b) isolating said antibody or antigen-binding fragment thereof from said cultured host cell.

In an eighth aspect, the disclosure provides an antibody or antigen-binding fragment thereof produced according to the method of the sixth aspect.

In a ninth aspect, the disclosure provides a pharmaceutical composition comprising an antibody or antigen-binding fragment thereof according to any of the preceding aspects or embodiments thereof, and a pharmaceutically acceptable excipient. In one embodiment, the pharmaceutical composition is provided for use as a medicament.

In a tenth aspect, the disclosure provides a method for treating an acute or chronic inflammatory disease, comprising administering to a subject in need thereof a pharmaceutically effective amount of the isolated antibody or fragment thereof according to any of the preceding aspects or embodiments thereof. In one embodiment, the inflammatory disease comprises chronic kidney disease (CKD) including, for example, CKD caused by diabetes, diabetic nephropathy, and high blood pressure.

In an eleventh aspect, the disclosure provides a method for treating an autoimmune disease, comprising: administering to a subject in need thereof a pharmaceutically effective amount of the isolated antibody or fragment thereof according to any of the preceding aspects or embodiments thereof. In one embodiment, the autoimmune disease comprises systemic lupus erythematosus, myositis, primary Sjögren's Syndrome, multiple sclerosis, uveitis, psoriasis, or rheumatoid arthritis.

These and other features and advantages of the present disclosure will be more fully understood from following detailed description of the disclosure taken together with the accompanying claims. It is noted that the scope of the claims is defined by the recitations therein and not by the specific discussion of features and advantages set forth in the present description.

BRIEF DESCRIPTION OF THE DRAWINGS

FIG. 1A depicts the alternating panning process with huFLT3L and muFLT3L and resultant enrichment of BMV, CS, DP47 and Dyax phage libraries. FIG. 1B depicts the process by which panning outputs were cloned into vectors for downstream competition HTRF. FIG. 1C depicts competition HTRF (homogeneous time-resolved fluorescence) results for lead candidates.

FIG. 2A demonstrates the increased expression of FLT3 in the RS4;11 cell line versus EOL-1, MOLM13, and MV4-11 cell lines. FIG. 2B confirms that recombinant FLT3L binds to FLT3 on RS4;11 cells in a dose-dependent manner.

FIG. 2C demonstrates that FLT3 downregulation on the surface of RS4;11 cells can be reliably detected with a commercially available anti-FLT3 antibody using flow cytometric analysis and this downregulation occurs in response to ligation with FLT3L in a dose-dependent manner.

FIG. 3A demonstrates the FLT3L titration curve used to derive the concentration at which 80% of cell surface FLT3 is downregulated on RS4;11 cells (EC80). FIG. 3B demonstrates the inhibition profile of a commercially available anti-FLT3 antibody and a recombinant construct of the FLT3 receptor (FLT3-Fc) against 96 pM of recombinant FLT3L that would otherwise result in downregulation of 80% of cell surface FLT3 on RS4;11 cells.

FIG. 4A demonstrates inhibition profiles of the five lead candidates against 96 pM human FLT3L.

FIG. 4B demonstrates inhibition profiles of the five lead candidates against 96 pM of cynomolgus FLT3L. FIG. 4C demonstrates inhibition profiles of the five lead candidates against murine FLT3L.

FIG. 5A demonstrates the ability of lead antibodies to bind human FLT3L expressed on the surface of transduced CHO cell lines. FIG. 5B demonstrates lead antibody binding cell surface cyno FLT3L.

FIG. 5C demonstrates lead antibody binding to cell surface mouse FLT3L.

FIGS. 6A-C. Lead candidate binding to endogenous human FLT3L. FIG. 6A demonstrates FLT3L expression on human primary T-cells following 7 days of stimulation with IL-2. FIG. 6B demonstrates the ability of all lead candidates to bind endogenous FLT3L on human primary T-cells, with the exception of clone 5D9. FIG. 6C demonstrates that improving the avidity of CAT5D9 by dimerization prior to incubation with primary T cells enabled detection of dose-dependent binding of the clone to endogenous FLT3L on the T cell surface.

FIG. 7A demonstrates the dose response curve of RS4;11 cells to FLT3L-expressing CHO cells, determining 1000 CHO per well as the optimal number to induce 80% downregulation of FLT3 on the RS4;11 cell surface. FIG. 7B demonstrates that all lead candidates possess the ability to inhibit cell-surface FLT3L on CHO cells to some extent.

FIG. 8A demonstrates a proof-of-concept study showing ERK signaling activation in RS4;11 cells by FLT3L. FIG. 8B demonstrates inhibition of FLT3L-induced ERK activation by a commercially available antibody.

FIG. 9A demonstrates functional activity of lead clone candidates against human FLT3L induced MEK 1/2 phosphorylation in primary CD133+ human stem cells. FIG. 9B provides additional confirmation of lead clone functional activity against FLT3L-induced signaling in primary CD133+ human stem cells, using ERK phosphorylation as a readout.

FIG. 10A shows Phase III binning of lead clone candidates and FLT3-Fc against clone 5D9. FIG. 10B shows Phase III binning of all lead clones and FLT3-Fc against CAT8, as representative of all clones other than CAT5D9.

FIG. 11A demonstrates that lead candidates do not bind to the structural homolog huSCF. FIG. 11B demonstrates that lead candidates do not bind to the structural homolog huCSF.

FIG. 12A demonstrates the results of a first round of clone optimization comparing parental CAT5D9 with clone 6 (C06) using the RS4;11 FLT3 downregulation assay as readout. FIG. 12B demonstrates the results of a second round of clone optimization comparing parental CAT5D9 with clone 6 (C06), and the final lead candidates: AM40 and SC4017.

FIG. 13A shows RS4:11 FLT3 downregulation in response to a serial dilution of FLT3L-expressing CD4+ T cells. FIG. 13B shows lead clones completely neutralize activity cell-surface FLT3L on CD4+ T cells.

FIG. 14. Study Outline of neutralizing FLT3L in healthy cynomolgus monkeys. Three groups of male cynomolgus monkeys (n=4 per group) were administered 0.03, 1, or 30 mg/kg AM40 (MEDI1116) in five weekly doses over a month, as indicated. An eight week follow-up period after the final dose was used to determine the persistence of the administered antibody and its effect on circulating DC populations.

FIGS. 15A and 15B. Serum FLT3L protein and circulating DC frequency following administration of anti-FLT3L antibody (AM40/MEDI1116). FIG. 15A Shows target engagement by MEDI1116, measuring free serum FLT3L levels following administration at 0.03, 1.0, and 30 mg/kg. Daily serum measurements were taken from Days 1-8, after which weekly measurements were taken until Day 85. FIG. 15B depicts reduction and recovery of circulating CD1c+(Classical DC) frequency (left) and plasmacytoid DC frequency (right), measured as a percentage of baseline, following treatment with MEDI1116.

FIG. 16A depicts FLT3L levels in serum of healthy donors (HD) and SLE patients. FIG. 16B depicts the correlation between serum FLT3L SLEDAI scores. FIG. 16C depicts circulating FLT3L+ T cell frequency in healthy donors (HD) and SLE patients. FIG. 16D depicts the correlation between FLT3L+ CD4+ T cells and SLEDAI scores.

FIG. 17A depicts the percent of CD4 $T_{naive}$ cells expressing FLT3L in HD and SLE patients. The bottom panel depicts the correlation of CD4 $T_{naive}$ cells expressing FLT3L in SLE patients versus SLEDAI score. FIG. 17B depicts the percent of CD4 $T_{MEM}$ cells expressing FLT3L in HD and SLE patients. The bottom panel depicts the correlation of CD4 $T_{MEM}$ cells expressing FLT3L in SLE patients versus SLEDAI score. FIG. 17C depicts the percent of CD4 $T_{CM}$ cells expressing FLT3L in HD and SLE patients. The bottom panel depicts the correlation of CD4 $T_{naive}$ cells expressing FLT3L in SLE patients versus SLEDAI score.

FIG. 18A depicts the percent of CD4 $T_{naive}$ cells expressing FLT3L in HD and myositis patients. FIG. 18B depicts the percent of CD4 $T_{MEM}$ cells expressing FLT3L in HD and myositis patients. FIG. 18C depicts the percent of CD4 $T_{CM}$ cells expressing FLT3L in HD and myositis patients.

FIG. 19A depicts reductions in proteinuria at 17 weeks post anti-FLT3L administration. FIG. 19B depicts nephritis scores at 18 weeks post anti-FLT3L administration.

FIG. 20A depicts changes in CD11+ siglec-H+pDC frequency after anti-FLT3L antibody administration. FIG. 20B depicts CD11c+CD11b+mDC frequency after anti-FLT3L antibody administration. FIG. 20C depicts CD11c+ CD8+mDC frequency after anti-FLT3L antibody administration.

FIG. 21A shows changes in salivary gland pathology in a NOD.H2h4 Sjögren's Syndrome mouse model after therapeutic dosing of anti-FLT3L antibody versus isotype control. FIG. 21B shows changes in salivary gland pathology in a NOD.H2h4 Sjögren's Syndrome mouse model after prophylactic dosing of anti-FLT3L antibody versus isotype control.

FIGS. 22A and 22B depict changes in plasmacytoid DC frequency (B220+ CD11c+ Siglec-H+) following anti-FLT3L antibody administration, shown by flow cytometry (A) and quantified (B). FIGS. 22C and 22D depict changes in classical DC frequency ($B220^{neg}CD11c^{HI}$) following anti-FLT3L antibody, shown by flow cytometry (C) and quantified (D).

FIG. 23A depicts anti-FLT3L antibody (MEDI1116) PK. FIG. 23B depicts soluble FLT3L levels at anti-FLT3L antibody (MEDI1116) doses of 0.03 mg/kg, 1.0 mg/kg, and 30 mg/kg. FIG. 23C depicts pDC frequency, measured as a percentage of baseline, at anti-FLT3L antibody (MEDI1116) doses of 0.03 mg/kg, 1.0 mg/kg, and 30 mg/kg.

FIGS. 24A-24C. Human dosing model for anti-FLT3L antibody (MEDI1116) projects Q4W dosing. FIG. 24A depicts anti-FLT3L antibody (MEDI1116) PK in cynomolgus monkeys. FIG. 24B depicts anti-FLT3L antibody (MEDI1116) PD in cynomolgus monkeys. FIG. 24C depicts predicted anti-FLT3L antibody (MEDI1116) PD in humans.

FIG. 25A depicts free serum FLT3L levels following administering the anti-FLT3L antibody and an isotype control antibody. Free FLT3L levels were measured using FT3L-IgG as capture and sulfo-tagged anti-mouse FLT3L polyclonal antibody as detection reagent. FIG. 25B depicts total (free and bound) serum FLT3L levels following administering the anti-FLT3L antibody and an isotype control antibody. Total FLT3L levels were measured using polyclonal anti-mouse FLT3L antibody for capture and detection.

FIG. 26A depicts $CD44^{HI}$ CD4+ T cell populations in spleen following administering the anti-FLT3L antibody and an isotype control antibody. FIG. 26B depicts $CD44^{HI}$ CD4+ T cell populations in LN following administering the anti-FLT3L antibody and an isotype control antibody. FIG. 26C depicts $CD44^{HI}$ CD8+ T cell populations in spleen following administering the anti-FLT3L antibody and an isotype control antibody. FIG. 26D depicts $CD44^{HI}$ CD8+ T cell populations in LN following administering the anti-FLT3L antibody and an isotype control antibody.

DETAILED DESCRIPTION OF THE INVENTION

Figure 1A:
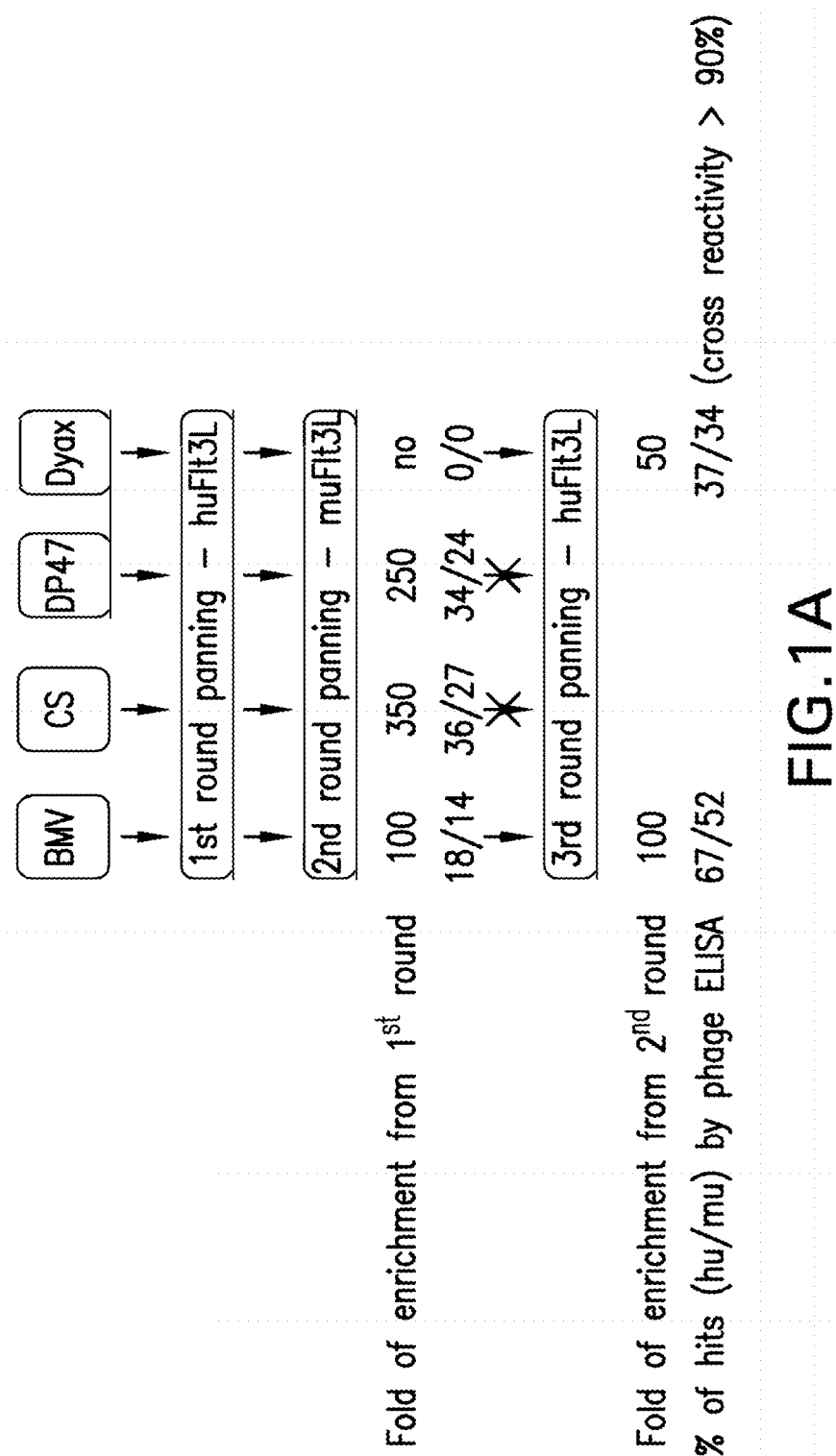
FIGS. 1A-1C. Lead antibody selection.

The present invention provides isolated antibodies or antigen-binding fragments thereof which specifically bind to FLT3L. In some aspects, such molecules are antibodies and antigen-binding fragments thereof that specifically bind to FLT3L. In one embodiment, the anti-FLT3L antibodies disclosed herein can be used to inhibit or decrease FLT3/FLT3L binding to inhibit the activation of inflammatory signaling pathways. Such an approach is advantageous as it attacks the inflammation at the signaling source allowing for a more robust anti-inflammatory treatment effect. Related polynucleotides, vectors, pharmaceutical compositions comprising the anti-FLT3L antibodies or antigen-binding fragments thereof, are also provided. Also contemplated are methods of making as well as methods of using the anti-FLT3L antibodies and antigen-binding fragments disclosed herein, for example, methods of treating autoimmune and/or chronic inflammatory diseases in a subject (as direct therapy, adjuvant therapy, or in combination therapy).

In order that the present disclosure can be more readily understood, certain terms are first defined. Additional definitions are set forth throughout the detailed description.

Definitions

Before describing the present invention in detail, it is to be understood that this invention is not limited to specific compositions or process steps, as such can vary. Unless defined otherwise, all technical and scientific terms used herein have the meanings commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "antibody," (or a fragment, variant, or derivative thereof) as used in this disclosure, refers to at least the minimal portion of an antibody which is capable of binding to antigen, e.g., at least the variable domain of a heavy chain (VH) and the variable domain of a light chain (VL) in the context of a typical antibody produced by a B cell. Basic antibody structures in vertebrate systems are relatively well understood. See, e.g., Harlow et al., Antibodies: A Laboratory Manual, (Cold Spring Harbor Laboratory Press, $2^{nd}$ ed., 1988). Antibodies or antigen-binding fragments, variants, or derivatives thereof include, but are not limited to, polyclonal, monoclonal, human, humanized, or chimeric, antibodies, epitope-binding fragments (e.g., Fab, F(ab')2, Fv, single-chain Fvs (scFv), single-chain antibodies, disulfide-linked Fvs (sdFv), fragments comprising either a VL or VH domain (Fd), fragments produced by a Fab expression library, and other antibody fragments and combinations thereof that retain antigen-binding function, i.e., the ability to bind, for example, FLT3L, specifically.

A typical antibody comprises at least two heavy (H) chains and two light (L) chains interconnected by disulfide bonds. Each heavy chain is comprised of a heavy chain variable region (abbreviated herein as VH or VH) and a heavy chain constant region. The heavy chain constant region is comprised of three domains, CHI, CH2, and CH3. Each light chain is comprised of a light chain variable region (abbreviated herein as VL or VL) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. Exemplary antibodies of the present disclosure include anti-FLT3L antibodies (original and germlined), affinity optimized clones, optimized antibodies lacking ADCC, conjugated antibodies (e.g., ADC), and other optimized antibodies (e.g., serum half-life-optimized antibodies including, for example, YTE mutations, see Dall'Acqua et al., J. Biol. Chem. 281:23514-24 (2006) and U.S. Pat. No. 7,083,784, which are hereby incorporated by reference in their entireties).

In certain embodiments, the CDRs of the VH (HCDR1, HCDR2, and HCDR3) and the CDRs of the VL (LCDR1, LCDR2, and LCDR3) consist of the amino acid sequences of: (a) SEQ ID NOs: 29, 30, 31, 32, 33, and 34, respectively; or (b) SEQ ID NOs: 29, 30, 31, 35, 33, and 34, respectively; or (c) SEQ ID Nos: 29, 36, 37, 32, 33, and 38, respectively.

An antibody can be of any the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. to form ADCs.

A "blocking" antibody or an "antagonist" antibody is one which inhibits or reduces biological activity of the antigen it binds, such as FLT3L. In a certain aspect, blocking antibodies or antagonist antibodies substantially or completely inhibit the biological activity of the antigen. For example, FLT3L-mediated activation of FLT3 can be reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or even 100%.

The terms "FLT3L antibody," "antibody that binds to FLT3L," or "anti-FLT3L antibody" refer to an antibody or antigen binding fragment thereof that is capable of binding FLT3L with sufficient affinity such that the molecule is useful as a therapeutic agent or diagnostic reagent in targeting FLT3L. The term "anti-FLT3L" also broadly encompasses molecules comprising, e.g., the CDRs of the antibodies disclosed herein incorporated into a scaffold.

The term "germlining" means that amino acids at specific positions in an antibody are mutated back to those in the germ line.

A "variable region" of an antibody refers to the variable region of the antibody light chain or the variable region of the antibody heavy chain, either alone or in combination.

The variable regions of the heavy and light chain each consist of four FW regions connected by three CDR regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Allazikani et al. (1997) J. Molec. Biol. 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The phrases "amino acid position numbering as in Kabat" or "Kabat position" and the like refer to the numbering system used for heavy chain variable domains or light chain variable domains of the compilation of antibodies in Kabat et al., 1991.

The terms "antigen-binding domain," "antigen-binding fragment," and "binding fragment" refer to a part of an antibody molecule that comprises amino acids responsible for the specific binding between the antibody and the antigen. The variable region allows the antibody or antigen-binding fragment to selectively recognize and specifically bind epitopes on antigens. That is, the VH and VL domain, or subset of the complementarity determining regions (CDRs), of an antibody combine to form the variable region that defines a three-dimensional antigen binding site. More specifically, the antigen-binding domain is defined by three CDRs on each of the VH and VL chains. As used herein, a portion of the antigen molecule that is responsible for specific interactions with the antigen-binding domain is referred to as an "epitope." An antigen-binding domain typically comprises an antibody light chain variable region and an antibody heavy chain variable region, however, it does not necessarily include both. For example, a so-called "Fd" antibody fragment consists only of a VH domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. Digestion of antibodies with the enzyme papain results in two identical antigen-binding fragments, known also as "Fab" fragments, and an "Fc" fragment, having no antigen-binding activity but having the ability to crystallize. Digestion of antibodies with the enzyme pepsin results in the F(ab')2 fragment in which the two arms of the antibody molecule remain linked and comprise two antigen-binding sites. The F(ab')2 fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CH1 domain of the heavy chain.

As used herein the Fc region includes the polypeptides comprising the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc can include the J chain. For IgG, Fc comprises immunoglobulin domains Cgamma2 and Cgamma3 (Cy2 and Cy3) and the hinge between Cgamma1 (Cy1) and Cgamma2 (Cy2). Although the boundaries of the Fc region can vary, the human IgG heavy chain Fc region is usually defined to comprise residues C226 or P230 to its carboxyl-terminus, wherein the numbering is according to the EU index as set forth in Kabat et al., 1991.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants.

The term "monoclonal antibody" encompasses both intact and full-length monoclonal antibodies as well as antibody fragments (such as Fab, Fab', F(ab')2, Fv), single chain variable fragments (scFv), fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals (e.g., expression of a human antibody in a transgenic mouse).

The term "humanized antibody" refers to an antibody derived from a non-human (e.g., murine) immunoglobulin, which has been engineered to increase similarity to antibody variants produced in humans.

The term "human antibody" refers to an antibody produced by a human or an antibody having an amino acid sequence corresponding to an antibody produced by a human made using any technique known in the art (e.g., recombinant expression in cultures cells, or expression in transgenic animals). Thus, the term human antibody also encompasses an antibody having an amino acid sequence corresponding to an antibody originally produced by a human (or an engineered variant or derivative thereof) but expressed in a non-human system (e.g., produced by chemical synthesis; recombinantly expressed in microbial, mammal, or insect cells; or expressed in an animal subject). Accordingly, an antibody obtained from a human subject or from human cells (e.g., hybridoma or cell line expressing a recombinant antibody or fragment thereof) and subsequently expressed in an animal, e.g., mice, is considered a human antibody. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more animal species. Typically, the variable region of both light and heavy chains corresponds to the variable region of antibodies derived from one species of mammals (e.g., mouse, rat, rabbit, etc.) with the desired specificity, and/or affinity, and/or capability while the constant regions are homologous to the sequences in antibodies derived from another specie (usually human) to avoid eliciting an immune response in that species.

The term "polynucleotide" is intended to encompass a singular nucleic acid as well as plural nucleic acids and refer to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association or linkage is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

In other embodiments, a polynucleotide can be RNA, for example, in the form of messenger RNA (mRNA).

A "vector" is a nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art.

A "transformed" cell, or a "host" cell, is a cell into which a nucleic acid molecule has been introduced by molecular biology techniques. As used herein, the term transformation encompasses all techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

As used herein, the term "FLT3L" refers to Feline McDonough Sarcoma (FMS)-like tyrosine kinase 3 ligand, a polypeptide which is a hematopoietic cytokine that binds to FMS-like tyrosine kinase 3 receptor (FLT3) receptor. FLT3L is initially expressed as a membrane-bound protein, before being enzymatically cleaved into a soluble form. Both membrane bound (mFLT3L) and secreted (sFLT3L) are included within the definition of FLT3L.

In this disclosure, "comprises," "comprising," "containing," and "having" and the like can have the meaning ascribed to them in U.S. patent law and can mean "includes," "including," and the like; "consisting essentially of" or "consists essentially of" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

As used herein, the terms "determining," "assessing," "assaying," "measuring," and "detecting" refer to both quantitative and qualitative determinations, and as such, the term "determining" can be used interchangeably herein with "assaying," "measuring," and the like. Where a quantitative determination is intended, the phrase "determining an amount" of an analyte and the like can be used. Where a qualitative and/or quantitative determination is intended, the phrase "determining a level" of an analyte or "detecting" an analyte is used.

The terms "identical" or "percent identity," in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences (see e.g., Karlin et al., 1990, *Proc. Nat. Acad. Sci.*, 87:2264-2268, as modified in Karlin et al., 1993, *Proc. Nat. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, California) or Megalign (DNASTAR).

The term "isolated" refers to a molecule that is not in its natural milieu. No particular level of purification is required. For example, an isolated antibody is an antibody that is not produced or situated in its native or natural environment. Recombinantly produced biological materials are considered isolated as disclosed herein, as are materials that are produced in a non-native cell, such as a hybridoma. A substance, e.g., an isolated protein, such as an antibody, is also considered "isolated" if it has been separated, fractionated, or partially or substantially purified by any suitable technique. For example, an antibody is considered "isolated" if it is substantially free of cellular material or other proteins from a cell or tissue source from which it is derived.

The term "specifically binds" refers to an agent (e.g., a ligand or antibody) that recognizes and binds a molecule (e.g., a receptor or an epitope), and that the binding entails some complementarity between the agent (e.g., antibody)

and the molecule (e.g., a ligand). By this definition, an antibody is said to "specifically bind" to a ligand when it binds to that ligand more readily than it would bind to a random, unrelated molecule. The term "specificity" is used herein to qualify the relative affinity by which a certain antibody binds to a certain ligand. For example, antibody "A" may be deemed to have a higher specificity for a given ligand (e.g., FLT3L) than antibody "B."

As used herein, the term "affinity" refers to a measure of the strength of the binding of an individual epitope with the CDR of an antibody. See, e.g., Harlow et al., Antibodies: A Laboratory Manual, (Cold Spring Harbor Laboratory Press), $2^{nd}$ ed. 1988) at pages 27-28. As used herein, the term "avidity" refers to the overall stability of the complex between a population of antibodies and an antigen, that is, the functional combining strength of an antibody mixture with the antigen. See e.g., Harlow at pages 39-34. Avidity is related to both the affinity of individual antibodies in the population with specific epitopes, and also the valency of the antibodies and the antigen.

The terms "inhibit" or "block" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity.

The term "effector function" refers to the activities of antibodies that result from the interactions of their Fc components with Fc receptors or components of complement. These activities include, for example, antibody-dependent cell-mediated cytotoxicity (ADCC), complement-dependent cytotoxicity (CDC), and antibody-dependent cell phagocytosis (ADCP). Thus an antigen binding protein (e.g., an antibody or antigen binding fragment thereof) with altered effector function refers to an antigen binding protein (e.g., an antibody or antigen binding fragment thereof) that contains an alteration in an Fc region (e.g., amino acid substitution, deletion, or addition or change in oligosaccharide) that changes the activity of at least one effector function (e.g., ADCC, CDC, and/or ADCP). An antigen binding protein (e.g., an antibody or antigen binding fragment thereof) with improved effector function refers to an antigen binding protein (e.g., an antibody or antigen binding fragment thereof) that contains an alteration in an Fc region (e.g., amino acid substitution, deletion, or addition or change in oligosaccharide) that increases the activity of at least one effector function (e.g., ADCC, CDC, and/or ADCP).

The term "subject" refers to any animal (e.g., a mammal), including, but not limited to humans, non-human primates, rodents, and the like, which is to be the recipient of a particular treatment. Typically, the terms "subject" and "patient" and "individual" are used interchangeably herein. Additional examples of subjects include non-human mammals, such as a bovine, equine, canine, ovine, or feline.

The term "pharmaceutical composition" refers to a preparation which is in such form as to permit the biological activity of the active ingredient (e.g., an anti-FLT3L antibody disclosed herein) to be effective, and which contains no additional components which are unacceptably toxic to a subject to which the composition would be administered. Such composition can be sterile.

An "effective amount" of an anti-FLT3L antibody as disclosed herein is an amount sufficient to carry out a specifically stated purpose. An "effective amount" can be determined empirically and in a routine manner, in relation to the stated purpose.

The terms "therapeutically effective amount" and "pharmaceutically effective amount" refer to an amount of an anti-FLT3L antibody disclosed herein or other drug effective to "treat" a disease or disorder in a subject.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for an autoimmune or inflammatory disease according to the methods of the present disclosure if the patient shows, e.g., total, partial, or transient reduction in symptoms associated with autoimmune or inflammatory disease.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like, refer to reducing and/or ameliorating a disorder and/or symptoms associated therewith. It will be appreciated that, although not precluded, treating a disorder or condition does not require that the disorder, condition, or symptoms associated therewith be completely eliminated. For example, as contemplated herein, treatment of a disorder includes preventing the exacerbation of symptoms of the disorder.

As used herein, the term "or" is understood to be inclusive unless specifically stated or obvious from context to the contrary. As used herein, the terms "a", "an", and "the" are understood to be singular or plural unless specifically stated or obvious from context to the contrary.

Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; and A (alone); B (alone); and C (alone).

Unless specifically stated or obvious from context, as used herein, the term "about" is understood as within a range of normal tolerance in the art, for example within 2 standard deviations of the mean. "About" can be understood as within greater or less than 10%, 9%, 8%, 7%, 6%, 5%, 4%, 3%, 2%, 1%, 0.5%, 0.1%, 0.05%, or 0.01% of a stated value. Unless indicated otherwise, all numerical values provided herein are considered to be implicitly modified by the term "about."

FLT3L is initially expressed as a membrane-bound protein, before being enzymatically cleaved into a soluble form. Both membrane bound (mFLT3L) and secreted (sFLT3L) are functionally active. The FLT3L binding region is highly conserved across species, so much so that that there is cross-species reactivity observed between human, rodent and cynomolgus ligand/receptor combinations. However, key mutations around the binding site are thought to explain a lack of cross-species reactivity of neutralizing antibodies generated to FLT3L. Neutralizing antibodies against FLT3L can affect classical and plasmacytoid DC populations, reducing the ability of the immune system to induce and sustain a prolonged inflammatory response. Secondary effects can include a decrease in circulating NK cells and reduced T and B-cell activation, leading to decreased survival of both cell types. Collectively, down-regulation of these pathways can reduce autoimmune inflammation.

In one embodiment, it is contemplated that a neutralizing anti-FLT3L antibody promotes immune homeostasis by inhibiting FLT3L from binding FLT3. The anti-FLT3L antibody strategy targets the ligand over the receptor to avoid risk of unexpected receptor dimerization or signaling. Unlike its receptor, there is no signaling domain associated with membrane-bound FLT3L.

Anti-FLT3L Antibodies

The present disclosure provides in a preferred embodiment isolated FLT3L binding molecules, e.g., antibodies and antigen-binding fragments thereof, that specifically bind FLT3L, for example, human FLT3L. The full-length amino acid and nucleotide sequences for FLT3L are known in the art (see, e.g., UniProt Acc. No. P36888 for human FLT3L, or UniProt Acc. No. Q00342 for mouse FLT3L). The anti-FLT3L antibodies of the present disclosure inhibit FLT3L-mediated activation of FLT3 and thereby decrease proinflammatory signaling and reduce inflammation in a subject.

In the preferred embodiment, the anti-FLT3L antibodies do not cross react with structural similar TKR homologues human stem cell factor (huSCF) or human colony stimulating factor (huCSF1). One skilled in the art will realize that SCF and CSF are ligands that also bind tyrosine kinase receptors. Non-specific FLT3 inhibitors that bind additional tyrosine kinase family members cause toxicity from global inhibition of tyrosine kinase signaling. Accordingly, it is critical that the anti-FLT3L antibodies only bind FLT3L, and not structurally similar homologues. Many anti-FLT3L antibodies and inhibitors lack specificity and bind a wide range of tyrosine kinase receptor. Thus, the anti-FLT3L antibody preferred embodiment must demonstrate high affinity for and specific binding of FLT3L.

In one embodiment, the anti-FLT3L antibodies of the present disclosure are monoclonal antibodies, recombinant antibodies, human antibodies, humanized antibodies, and/or chimeric antibodies.

In some aspects, FLT3L binding molecules comprise a Fab, a Fab', a F(ab')2, a Fd, a single chain Fv or scFv, a disulfide linked Fv, a V-NAR domain, an IgNar, an intrabody, an IgG CH2, a minibody, a F(ab')$_3$ a tetrabody, a triabody, a diabody, a single-domain antibody, DVD-Ig, Fcab, mAb$^2$, a (scFv)$_2$, or a scFv-Fc. In some aspects, the anti-FLT3L antibodies are of the IgG type, for example of the IgG1 type (includes an IgG1 heavy chain immunoglobulin constant domain). In other embodiments, the anti-FLT3L antibodies have an IgA, IgD, IgE, IgG2, IgG3, IgG4, or IgM heavy chain immunoglobulin constant domain.

In some embodiments, the IgG constant region can comprise a light chain constant region selected from the group consisting of an Ig kappa constant domain (region) and an Ig lambda constant domain. In one particular embodiment, the anti-FLT3L antibodies include a human IgG1 constant domain and a human lambda constant domain. In another particular embodiment, anti-FLT3L antibodies have an IgG1-TM format such that targeted mutations in the Fc region change leucine at 243 to phenylalanine (L243F), leucine at 235 to glutamic acid (L235E), and proline at 331 to serine (P331S); the amino acid numbering is according to the EU index. The targeted mutations reduce FcR binding and ADCC effector function (see Organesyan et al., *Acta Crystallogr D Biol Crystallogr.* 2008 Jun. 1; 64 (Pt 6): 700-4; and WO 2009100309 A2, which is incorporated by reference).

In some aspects, the anti-FLT3L antibodies are human antibodies (for example, CAT5D9, SC4017, AM40, CAT8, CAT26, DTAX3, and DYAX5 antibodies).

The CAT5D9 Antibody

In one embodiment, the CAT5D9 antibody refers to an antibody that specifically binds to FLT3L and includes Complementarity-Determining Regions (CDRs): HCDR1, HCDR2, HCDR3, LCDR1, LCDR2, and LCDR3. HCDR1, HCDR2, HCDR3, LCDR1, LCDR2, and LCDR3 include the amino acid sequences of SEQ ID NOs: 29, 36, 37, 32, 33, and 38, respectively.

In another embodiment, the CAT5D9 antibody refers to an antibody that specifically binds to FLT3L and includes two VL domains having at least 95%, 96%, 97%, 98%, or 99% sequence identity to the amino acid sequence of SEQ ID NO: 6 and two VH domains having at least 95%, 96%, 97%, 98%, or 99% sequence identity to the amino acid sequence of SEQ ID NO: 5.

In a further embodiment, the CAT5D9 antibody refers to an antibody that includes two VL domains having the amino acid sequence of SEQ ID NO: 6 and two VH domains having the amino acid sequence of SEQ ID NO: 5.

In another embodiment, the CAT5D9 antibody refers to an antibody that includes two VL domains encoded by the nucleic acid sequence of SEQ ID NO: 20 and two VH domains encoded by the nucleic acid sequence of SEQ ID NO: 19.

In one embodiment, the CAT5D9 antibody refers to an IgG1 antibody that specifically binds to FLT3L and includes a light chain having the amino acid sequence of SEQ ID NO: 70 and a heavy chain having the amino acid sequence of SEQ ID NO: 69.

In another embodiment, the CAT5D9 antibody refers to an antibody that includes a light chain encoded by the nucleic acid sequence of SEQ ID NO: 72 and a heavy chain encoded by the nucleic acid sequence of SEQ ID NO: 71.

The SC4017 Antibody

In one embodiment, the SC4017 antibody refers to an antibody that specifically binds to FLT3L and includes Complementarity-Determining Regions (CDRs): HCDR1, HCDR2, HCDR3, LCDR1, LCDR2, and LCDR3. HCDR1, HCDR2, HCDR3, LCDR1, LCDR2, and LCDR3 include the amino acid sequences of SEQ ID NOs: 29, 30, 31, 35, 33, and 34, respectively.

In another embodiment, the SC4017 antibody refers to an antibody that specifically binds to FLT3L and includes two VL domains having at least 95%, 96%, 97%, 98%, or 99% sequence identity to the amino acid sequence of SEQ ID NO: 4 and two VH domains having at least 95%, 96%, 97%, 98%, or 99% sequence identity to the amino acid sequence of SEQ ID NO: 3.

In a further embodiment, the SC4017 antibody refers to an antibody that includes two VL domains having the amino acid sequence of SEQ ID NO: 4 and two VH domains having the amino acid sequence of SEQ ID NO: 3.

In another embodiment, the SC4017 antibody refers to an antibody that includes two VL domains encoded by the nucleic acid sequence of SEQ ID NO: 18 and two VH domains encoded by the nucleic acid sequence of SEQ ID NO: 17.

In one embodiment, the SC4017 antibody refers to an IgG1 antibody that specifically binds to FLT3L and includes a light chain having the amino acid sequence of SEQ ID NO: 66 and a heavy chain having the amino acid sequence of SEQ ID NO: 65.

In another embodiment, the SC4017 antibody refers to an antibody that includes a light chain encoded by the nucleic acid sequence of SEQ ID NO: 68 and a heavy chain encoded by the nucleic acid sequence of SEQ ID NO: 67.

The AM40 (MEDI1116) Antibody

In one embodiment, the AM40 antibody refers to an antibody that specifically binds to FLT3L and includes Complementarity-Determining Regions (CDRs): HCDR1, HCDR2, HCDR3, LCDR1, LCDR2, and LCDR3. HCDR1, HCDR2, HCDR3, LCDR1, LCDR2, and LCDR3 include the amino acid sequences of SEQ ID NOs: 29, 30, 31, 32, 33, and 34, respectively.

In another embodiment, the AM40 antibody refers to an antibody that specifically binds to FLT3L and includes two VL domains having at least 95%, 96%, 97%, 98%, or 99% sequence identity to the amino acid sequence of SEQ ID NO: 2 and two VH domains having at least 95%, 96%, 97%, 98%, or 99% sequence identity to the amino acid sequence of SEQ ID NO: 1.

In a further embodiment, the AM40 antibody refers to an antibody that includes two VL domains having the amino acid sequence of SEQ ID NO: 2 and two VH domains having the amino acid sequence of SEQ ID NO: 1.

In another embodiment, the AM40 antibody refers to an antibody that includes two VL domains encoded by the nucleic acid sequence of SEQ ID NO: 16 and two VH domains encoded by the nucleic acid sequence of SEQ ID NO: 15.

In one embodiment, the AM40 antibody refers to an IgG1 antibody that specifically binds to FLT3L and includes a light chain having the amino acid sequence of SEQ ID NO: 62 and a heavy chain having the amino acid sequence of SEQ ID NO: 61.

In another embodiment, the AM40 antibody refers to an antibody that includes a light chain encoded by the nucleic acid sequence of SEQ ID NO: 64 and a heavy chain encoded by the nucleic acid sequence of SEQ ID NO: 63.

The CAT8 Antibody

In one embodiment, the CAT8 antibody refers to an antibody that specifically binds to FLT3L and includes Complementarity-Determining Regions (CDRs): HCDR1, HCDR2, HCDR3, LCDR1, LCDR2, and LCDR3. HCDR1, HCDR2, HCDR3, LCDR1, LCDR2, and LCDR3 include the amino acid sequences of SEQ ID NOs: 39, 40, 41, 42, 43, and 44, respectively.

In another embodiment, the CAT8 antibody refers to an antibody that specifically binds to FLT3L and includes two VL domains having at least 95%, 96%, 97%, 98%, or 99% sequence identity to the amino acid sequence of SEQ ID NO: 8 and two VH domains having at least 95%, 96%, 97%, 98%, or 99% sequence identity to the amino acid sequence of SEQ ID NO: 7.

In a further embodiment, the CAT8 antibody refers to an antibody that includes two VL domains having the amino acid sequence of SEQ ID NO: 8 and two VH domains having the amino acid sequence of SEQ ID NO: 7.

In another embodiment, the CAT8 antibody refers to an antibody that includes two VL domains encoded by the nucleic acid sequence of SEQ ID NO: 22 and two VH domains encoded by the nucleic acid sequence of SEQ ID NO: 21.

In one embodiment, the CAT8 antibody refers to an IgG1 antibody that specifically binds to FLT3L and includes a light chain having the amino acid sequence of SEQ ID NO: 74 and a heavy chain having the amino acid sequence of SEQ ID NO: 73.

In another embodiment, the CAT8 antibody refers to an antibody that includes a light chain encoded by the nucleic acid sequence of SEQ ID NO: 76 and a heavy chain encoded by the nucleic acid sequence of SEQ ID NO: 75.

The CAT26 Antibody

In one embodiment, the CAT26 antibody refers to an antibody that specifically binds to FLT3L and includes Complementarity-Determining Regions (CDRs): HCDR1, HCDR2, HCDR3, LCDR1, LCDR2, and LCDR3. HCDR1, HCDR2, HCDR3, LCDR1, LCDR2, and LCDR3 include the amino acid sequences of SEQ ID NOs: 45, 40, 46, 47, 48, and 49, respectively.

In another embodiment, the CAT26 antibody refers to an antibody that specifically binds to FLT3L and includes two VL domains having at least 95%, 96%, 97%, 98%, or 99% sequence identity to the amino acid sequence of SEQ ID NO: 10 and two VH domains having at least 95%, 96%, 97%, 98%, or 99% sequence identity to the amino acid sequence of SEQ ID NO: 9.

In a further embodiment, the CAT26 antibody refers to an antibody that includes two VL domains having the amino acid sequence of SEQ ID NO: 10 and two VH domains having the amino acid sequence of SEQ ID NO: 9.

In another embodiment, the CAT26 antibody refers to an antibody that includes two VL domains encoded by the nucleic acid sequence of SEQ ID NO: 24 and two VH domains encoded by the nucleic acid sequence of SEQ ID NO: 23.

In one embodiment, the CAT26 antibody refers to an IgG1 antibody that specifically binds to FLT3L and includes a light chain having the amino acid sequence of SEQ ID NO: 78 and a heavy chain having the amino acid sequence of SEQ ID NO: 77.

In another embodiment, the CAT26 antibody refers to an antibody that includes a light chain encoded by the nucleic acid sequence of SEQ ID NO: 80 and a heavy chain encoded by the nucleic acid sequence of SEQ ID NO: 79.

The DYAX3 Antibody

In one embodiment, the Dyax3 antibody refers to an antibody that specifically binds to FLT3L and includes Complementarity-Determining Regions (CDRs): HCDR1, HCDR2, HCDR3, LCDR1, LCDR2, and LCDR3. HCDR1, HCDR2, HCDR3, LCDR1, LCDR2, and LCDR3 include the amino acid sequences of SEQ ID NOs: 50, 51, 52, 53, 54, and 55, respectively.

In another embodiment, the Dyax3 antibody refers to an antibody that specifically binds to FLT3L and includes two VL domains having at least 95%, 96%, 97%, 98%, or 99% sequence identity to the amino acid sequence of SEQ ID NO: 82 and two VH domains having at least 95%, 96%, 97%, 98%, or 99% sequence identity to the amino acid sequence of SEQ ID NO: 81.

In a further embodiment, the Dyax3 antibody refers to an antibody that includes two VL domains having the amino acid sequence of SEQ ID NO: 12 and two VH domains having the amino acid sequence of SEQ ID NO: 11.

In another embodiment, the Dyax3 antibody refers to an antibody that includes two VL domains encoded by the nucleic acid sequence of SEQ ID NO: 26 and two VH domains encoded by the nucleic acid sequence of SEQ ID NO: 25.

In one embodiment, the Dyax3 antibody refers to an IgG1 antibody that specifically binds to FLT3L and includes a light chain having the amino acid sequence of SEQ ID NO: 82 and a heavy chain having the amino acid sequence of SEQ ID NO: 81.

In another embodiment, the Dyax3 antibody refers to an antibody that includes a light chain encoded by the nucleic acid sequence of SEQ ID NO: 84 and a heavy chain encoded by the nucleic acid sequence of SEQ ID NO: 83.

The DYAX5 Antibody

In one embodiment, the Dyax5 antibody refers to an antibody that specifically binds to FLT3L and includes Complementarity-Determining Regions (CDRs): HCDR1, HCDR2, HCDR3, LCDR1, LCDR2, and LCDR3. HCDR1, HCDR2, HCDR3, LCDR1, LCDR2, and LCDR3 include the amino acid sequences of SEQ ID NOs: 56, 57, 52, 58, 59, and 60, respectively.

In another embodiment, the Dyax5 antibody refers to an antibody that specifically binds to FLT3L and includes two VL domains having at least 95%, 96%, 97%, 98%, or 99% sequence identity to the amino acid sequence of SEQ ID NO: 86 and two VH domains having at least 95%, 96%, 97%, 98%, or 99% sequence identity to the amino acid sequence of SEQ ID NO: 85.

In a further embodiment, the Dyax5 antibody refers to an antibody that includes two VL domains having the amino acid sequence of SEQ ID NO: 14 and two VH domains having the amino acid sequence of SEQ ID NO: 13.

In another embodiment, the Dyax5 antibody refers to an antibody that includes two VL domains encoded by the nucleic acid sequence of SEQ ID NO: 28 and two VH domains encoded by the nucleic acid sequence of SEQ ID NO: 27.

In one embodiment, the Dyax5 antibody refers to an IgG1 antibody that specifically binds to FLT3L and includes a light chain having the amino acid sequence of SEQ ID NO: 86 and a heavy chain having the amino acid sequence of SEQ ID NO: 85.

In another embodiment, the Dyax5 antibody refers to an antibody that includes a light chain encoded by the nucleic acid sequence of SEQ ID NO: 88 and a heavy chain encoded by the nucleic acid sequence of SEQ ID NO: 87.

In certain embodiments is provided an antibody or antigen-binding fragment thereof that specifically binds to FLT3L, comprising a set of Complementarity-Determining Regions (CDRs): HCDR1, HCDR2, HCDR3, LCDR1, LCDR2, and LCDR3 wherein the HCDR1, HCDR2, HCDR3, LCDR1, LCDR2, and LCDR3 comprise the amino acid sequences of: (a) SEQ ID NOs: 29, 30, 31, 32, 33, and 34, respectively; or (b) SEQ ID NOs: 29, 30, 31, 35, 33, and 34, respectively; or (c) SEQ ID Nos: 29, 36, 37, 32, 33, and 38, respectively.

In certain embodiments, the antibody or antigen-binding fragment thereof comprises a heavy chain variable region (VH) and light chain variable region (VL), wherein each VH and VL comprises three CDRs and four framework regions (FWs), arranged from amino-terminus to carboxy-terminus in the following order: FW1, CDR1, FW2, CDR2, FW3, CDR3, and FW4.

In certain aspects, the VH and VL regions have and amino acid sequence having at least 95%, 96%, 97%, 98%, or 99% sequence identity to: (a) SEQ ID NO: 1 and SEQ ID NO: 2, respectively; or (b) SEQ ID NO: 3 and SEQ ID NO: 4, respectively; or (c) SEQ ID NO: 5 and SEQ ID NO: 6, respectively.

In certain aspects, the CDRs of the VH (HCDR1, HCDR2, and HCDR3) and the CDRs of the VL (LCDR1, LCDR2, and LCDR3) consist of the amino acid sequences of: (a) SEQ ID NOs: 29, 30, 31, 32, 33, and 34, respectively; or (b) SEQ ID NOs: 29, 30, 31, 35, 33, and 34, respectively; or (c) SEQ ID Nos: 29, 36, 37, 32, 33, and 38, respectively.

A summary table of anti-FLT3L antibody sequences is present below in Table 1.

TABLE 1

Anti-FLT3L Antibody Sequence Summary Table.

Table 1A

| Antibody Name | VH (amino acid) | VL (amino acid) |
| --- | --- | --- |
| AM40 | QVQLVQSGAEVKKPGSSVKVSCKAS GGTFSSYALSWVRQAPGQGLEWMG TRPPTSRTASYAQKFQGRVTITVDE STSTGYMELSSLRSEDTAVYYCASND FVYGSYRFWGQGTTVTVSSA (SEQ ID NO: 1) | NFMLTQPHSVSESPGKTVTISCTRTS GNIAGYFVQWYQQRPGSSPTTVIYE DYQRPSGVPDRFSGSIDSSSNSASLTI SGLKTEDEADYYCQSYDDYRRAAF GGGTKLTVL (SEQ ID NO: 2) |
| SC4017 | QVQLVQSGAEVKKPGSSVKVSCKAS GGTFSSYALSWVRQAPGQGLEWMG TRPPTSRTASYAQKFQGRVTITVDE STSTGYMELSSLRSEDTAVYYCASND FVYGSYRFWGQGTTVTVSS (SEQ ID NO: 3) | NFMLTQPHSVSESPGKTVTISCTRTS GWIAGYFVQWYQQRPGSSPTTVIYE DYQRPSGVPDRFSGSIDSSSNSASLTI SGLKTEDEADYYCQSYDDYRRAAF GGGTKLTVL (SEQ ID NO: 4) |
| CAT5D9 | QVQLVQSGAEVKKPGSSVKVSCKISG GTFSSYALSWVRQAPGQGLEWMGGI IPVFRTASYAQKFQGRVTITVDESAS TGYIELSSLKSEDTATYYCASNNYVW GSYRFWGQGTTVTVSS (SEQ ID NO: 5) | NFMLTQPHSVSESPGKTVTISCTRTS GNIAGYFVQWYQQRPGSSPTTVIYE DYQRPSGVPDRFSGSIDRSSNSASLTI SGLKPDDEADYYCQSYDDTSQGVFG AGTKVTVL (SEQ ID NO: 6) |
| CAT8 | EVQLLESGGGLVQPGGSLRLSCAASG FTFSSYAMSWVRQAPGKGLEWVSAI SGSGGSTYYADSVKGRFTISRDNSK NTLYLQMNSLRAEDTAVYYCARSSG YYGANFDFWGQGTTVTVSS (SEQ ID NO: 7) | QSVLTQPPSASGTPGQRVAISCSGSSS NIGSGYVYWYQQVPGTAPTLLIHRN NQRPSGVPDRFSGSKSGTSASLAISG LRSEDEADYYCAAWDDSLSGYVFG TGTKVTV (SEQ ID NO: 8) |

TABLE 1-continued

Anti-FLT3L Antibody Sequence Summary Table.

| | | |
|---|---|---|
| CAT26 | EVQLLESGGGLVQPGGSLRLSCAASG FTFSSYAVSWVRQAPGKGLEWVSAI SGSGGSTYYADSVKGRFTISRDNSK NTLYLQMNSLRAEDTAVYYCVKDA YGSSWYFYYFDYWGQGTMVTVSS (SEQ ID NO: 9) | QSVLTQPPSASGTPGQRVTISCSGSSS NIGINPVNWYQQLPGTAPKVLIYSD KYRPSGVADRFSGSKSGTSASLAISG LQSEDEADYFCAAWDDSLNGRVFG TGTKLTVL (SEQ ID NO: 10) |
| Dyax3 | EVQLLESGGGLVQPGGSLRLSCAASG FTFSMYEMRWVRQAPGKGLEWVSV IPSGGKTFYADSVKGRFTISRDNSKN TLYLQMNSLRAEDTAVYYCARYSRW FGQLGFYSHYAMDVWSQGTTVTVSS (SEQ ID NO: 11) | DIQMTQSPSSLSASVGDRVAITCRAS QSIDTYLNWYQQKPGKAPKLLIYAA SKLEDGVPSRFSGSGTGTDFTLTIRSL QPEDFASYFCQQSYSSPGITFGPGTK VEIK (SEQ ID NO: 12) |
| Dyax5 | EVQLLESGGGLVQPGGSLRLSCAASG FTFSSYIMVWVRQAPGKGLEWVSSI YSSGGSTSYADSVKGRFTISRDNSKN TLYLQMNSLRAEDTAVYYCTRYSRW FGQLGFYSHYAMDVWSQGTTVTVSS (SEQ ID NO: 13) | DIQMTQSPSSLSASVGDRVTITCRAS QSISSYLNWYQQKPGKAPKLLIYAAS SLQSGVPSRFSGSGSGTDFTLTISSLQ PEDFATYYCQQSYSTPPWTFGQGTK VEIK (SEQ ID NO: 14) |

TABLE 1B

| Antibody Name | VH (DNA) | VL (DNA) |
|---|---|---|
| AM40 | CAGGTGCAGCTGGTGCAGTCTGGG GCTGAGGTGAAGAAGCCTGGGTCC TCGGTGAAGGTCTCCTGCAAGGCTT CTGGAGGCACCTTCAGCAGTTATGC TCTTAGCTGGGTGCGACAGGCCCCT GGACAAGGGCTTGAGTGGATGGGA ACGCGGCCGCCGACCTCCCGGACA GCAAGCTACGCACAGAAATTTCAG GGCAGAGTCACGATTACCGTGGAC GAATCCACGAGCACAGGCTACATG GAGCTGAGCAGCCTGAGATCTGAG GACACGGCCGTGTATTACTGTGCGT CAAACGACTTCGTGTACGGGAGTT ATCGTTTCTGGGGCCAAGGGACCA CGGTCACCGTCTCCTCAGCG (SEQ ID NO: 15) | AATTTTATGCTGACTCAGCCCCACT CTGTGTCGGAGTCTCCGGGGAAGA CGGTAACCATCTCCTGCACCCGCAC CAGTGGGAACATTGCCGGCTACTTT GTGCAGTGGTACCAGCAGCGCCCG GGCAGTTCCCCCACCACTGTGATCT ATGAGGATTACCAACGACCCTCTGG GGTCCCTGATCGGTTCTCTGGCTCC ATCGACAGCTCCTCCAACTCTGCCT CCCTCACCATCTCTGGACTGAAGAC TGAGGACGAGGCTGACTACTATTGT CAGTCTTATGATGACTACCGGCGGG CGGCGTTCGGCGGAGGGACCAAGC TGACCGTCCTA (SEQ ID NO: 16) |
| SC4017 | CAGGTGCAGCTGGTGCAGTCTGGG GCTGAGGTGAAGAAGCCTGGGTCC TCGGTGAAGGTCTCCTGCAAGGCTT CTGGAGGCACCTTCAGCAGTTATGC TCTTAGCTGGGTGCGACAGGCCCCT GGACAAGGGCTTGAGTGGATGGGA ACGCGGCCGCCGACCTCCCGGACA GCAAGCTACGCACAGAAATTTCAG GGCAGAGTCACGATTACCGTGGAC GAATCCACGAGCACAGGCTACATG GAGCTGAGCAGCCTGAGATCTGAG GACACGGCCGTGTATTACTGTGCGT CAAACGACTTCGTGTACGGGAGTT ATCGTTTCTGGGGCCAAGGGACCA CGGTCACCGTCTCCTCA (SEQ ID NO: 17) | AATTTTATGCTGACTCAGCCCCACT CTGTGTCGGAGTCTCCGGGGAAGA CGGTAACCATCTCCTGCACCCGCAC CAGTGGGTGGATTGCCGGCTACTTT GTGCAGTGGTACCAGCAGCGCCCG GGCAGTTCCCCCACCACTGTGATCT ATGAGGATTACCAACGACCCTCTG GGGTCCCTGATCGGTTCTCTGGCTC CATCGACAGCTCCTCCAACTCTGCC TCCCTCACCATCTCTGGACTGAAGA CTGAGGACGAGGCTGACTACTATT GTCAGTCTTATGATGACTACCGGCG GGCGGCGTTCGGCGGAGGGACCAA GCTGACCGTCCTA (SEQ ID NO: 18) |
| CAT5D9 | CAGGTGCAGCTGGTGCAGTCTGGG GCTGAGGTGAAGAAGCCTGGGTCC TCGGTGAAGGTCTCCTGCAAGGATT CTGGAGGCACCTTCAGCAGTTATGC TCTTAGCTGGGTGCGACAGGCCCCT GGACAAGGGCTTGAGTGGATGGGA GGGATCATCCCTGTCTTTCGGACAG CAAGCTACGCACAGAAATTTCAGG GCAGAGTCACGATTACCGTGGACG AATCCGCGAGCACAGGCTACATAG AACTGAGCAGCCTGAAATCTGAGG ACACGGCCACATATTACTGTGCGTC AAATAATTACGTTTGGGGGAGTTAT CGTTTCTGGGGCCAGGGGACCACG GTCACCGTCTCCTCA (SEQ ID NO: 19) | AATTTTATGCTGACTCAGCCCCACT CTGTGTCGGAGTCTCCGGGGAAGA CGGTCACCATCTCCTGCACCCGCAC CAGTGGGAACATTGCCGGCTACTTT GTGCAGTGGTACCAGCAGCGCCCG GGCAGTTCCCCCACCACTGTGATCT ATGAGGATTACCAACGACCCTCTG GGGTCCCTGATCGGTTCTCTGGCTC CATCGACAGGTCCTCCAACTCTGCC TCCCTCACCATCTCTGGACTGAAGC CTGACGACGAGGCTGACTATTG TCAGTCTTATGATGACACCTCTCAA GGTGTGTTCGGCGCAGGGACCAAG GTCACCGTCCTA (SEQ ID NO: 20) |

TABLE 1-continued

Anti-FLT3L Antibody Sequence Summary Table.

CAT8
GAGGTGCAGCTGTTGGAGTCTGGG
GGAGGCTTGGTACAGCCTGGGGGG
TCCCTGAGACTCTCCTGTGCAGCCT
CTGGATTCACCTTTAGCAGCTATGC
CATGAGCTGGGTCCGCCAGGCTCC
AGGGAAGGGGCTGGAGTGGGTCTC
AGCTATTAGTGGTAGTGGTGGTAGC
ACATACTACGCAGACTCCGTGAAG
GGCCGGTTCACCATCTCCAGAGAC
AATTCCAAGAACACGCTGTATCTGC
AAATGAACAGCCTGAGAGCCGAGG
ACACGGCCGTGTATTACTGTGCGAG
AAGCAGCGGCTACTACGGGGCCAA
TTTTGACTTCTGGGGCCAGGGGACC
ACGGTCACCGTCTCGAGT
(SEQ ID NO: 21)

CAGTCTGTGCTGACGCAGCCGCCCT
CAGCGTCCGGGACCCCCGGGCAGA
GGGTCGCCATCTCTTGTTCTGGAAG
CAGCTCCAACATCGGAAGTGGTTAT
GTATACTGGTATCAGCAGGTCCCAG
GAACGGCCCCCACACTCCTCATCCA
TAGGAATAATCAGCGGCCCTCAGG
GGTCCCTGACCGATTCTCTGGCTCC
AAGTCTGGCACCTCAGCCTCCCTGG
CCATCAGTGGGCTCCGGTCCGAGG
ATGAGGCTGATTATTACTGTGCAGC
GTGGGATGACAGCCTGAGTGGTTA
TGTCTTCGGAACTGGGACCAAGGTC
ACCGTC
(SEQ ID NO: 22)

CAT26
GAGGTGCAGCTGTTGGAGTCTGGG
GGAGGCTTGGTACAGCCTGGGGGG
TCCCTGAGACTCTCCTGTGCAGCCT
CTGGATTCACCTTTAGCAGCTATGC
CGTGAGCTGGGTCCGCCAGGCTCC
AGGGAAGGGGCTGGAGTGGGTCTC
AGCTATTAGTGGTAGTGGTGGTAGC
ACATACTACGCAGACTCCGTGAAG
GGCCGGTTCACCATCTCCAGAGAC
AATTCCAAGAACACGCTGTATCTGC
AAATGAACAGCCTGAGAGCCGAGG
ACACGGCCGTGTATTACTGTGTGAA
AGACGCATATGGCAGCAGCTGGTA
CTTTTACTACTTTGACTACTGGGGC
CAAGGGACAATGGTCACCGTCTCG
AGT
(SEQ ID NO: 23)

CAGTCTGTGTTGACGCAGCCGCCTT
CAGCGTCTGGGACCCCCGGGCAGA
GGGTCACCATCTCTTGTTCTGGAAG
CAGCTCCAACATCGGAATCAATCCT
GTGAACTGGTACCAACAACTCCCC
GGAACGGCCCCCAAAGTCCTCATTT
ATAGTGATAAATACCGGCCCTCAG
GGGTCGCTGACCGCTTCTCTGGCTC
CAAGTCTGGAACCTCAGCCTCCCTG
GCCATCAGTGGCCTCCAGTCTGAGG
ATGAGGCTGATTACTTCTGTGCAGC
ATGGGATGACAGCCTGAATGGTCG
CGTCTTCGGAACTGGGACCAAGCT
GACCGTCCTA
(SEQ ID NO: 24)

Dyax3
GAAGTTCAATTGTTAGAGTCTGGTG
GCGGTCTTGTTCAGCCTGGTGGTTC
TTTACGTCTTTCTTGCGCTGCTTCCG
GATTCACTTTCTCTATGTACGAGAT
GCGTTGGGTTCGCCAAGCTCCTGGT
AAAGGTTTGGAGTGGGTTTCTGTTA
TCCCTTCTGGTGGCAAGACTTTTTA
TGCTGACTCCGTTAAAGGTCGCTTC
ACTATCTCTAGAGACAACTCTAAGA
ATACTCTCTACTTGCAGATGAACAG
CTTAAGGGCTGAGGACACGGCCGT
GTATTACTGTGCGAGATACAGCAG
ATGGTTCGGGCAGCTAGGGTTTTAC
TCCCACTACGCTATGGACGTCTGGA
GCCAAGGGACCACGGTCACCGTCT
CAAGC
(SEQ ID NO: 25)

GACATCCAGATGACCCAGTCTCCAT
CCTCCCTGTCTGCATCTGTGGGAGA
CAGAGTCGCCATCACTTGCCGCGCA
AGTCAGAGCATCGACACCTATTTAA
ATTGGTATCAGCAGAAACCAGGGA
AAGCCCCTAAACTCCTGATCTATGC
TGCATCCAAGTTGGAAGACGGGGT
CCCATCAAGATTCAGTGGCAGTGG
AACTGGGACAGATTTCACTCTCACC
ATCAGAAGTCTGCAACCTGAAGAT
TTTGCAAGTTATTTCTGTCAACAGA
GCTACTCTAGTCCAGGGATCACTTT
CGGCCCTGGGACCAAGGTGGAGAT
CAAA
(SEQ ID NO: 26)

Dyax5
GAAGTTCAATTGTTAGAGTCTGGTG
GCGGTCTTGTTCAGCCTGGTGGTTC
TTTACGTCTTTCTTGCGCTGCTTCCG
GATTCACTTTCTCTTCTTACATTATG
GTTTGGGTTCGCCAAGCTCCTGGTA
AAGGTTTGGAGTGGGTTTCTTCTAT
CTATTCTTCTGGTGGCTCTACTTCTT
ATGCTGACTCCGTTAAAGGTCGCTT
CACTATCTCTAGAGACAACTCTAAG
AATACTCTCTACTTGCAGATGAACA
GCTTAAGGGCTGAGGACACAGCCG
TGTATTACTGTACGAGATACAGCAG
ATGGTTCGGGCAGCTAGGGTTTTAC
TCCCACTACGCTATGGACGTCTGGA
GCCAAGGGACCACGGTCACCGTCT
CAAGC
(SEQ ID NO: 27)

GACATCCAGATGACCCAGTCTCCAT
CCTCCCTGTCTGCATCTGTAGGAGA
CAGAGTCACCATCACTTGCCGGGC
AAGTCAGAGCATTAGCAGCTATTTA
AATTGGTATCAGCAGAAACCAGGG
AAAGCCCCTAAGCTCCTGATCTATG
CTGCATCCAGTTTGCAAAGTGGGGT
CCCATCAAGGTTCAGTGGCAGTGG
ATCTGGGACAGATTTCACTCTCACC
ATCAGCAGTCTGCAACCTGAAGATT
TTGCAACTTACTACTGTCAACAGAG
TTACAGTACCCCTCCGTGGACGTTC
GGCCAAGGGACCAAGGTGGAAATC
AAA
(SEQ ID NO: 28)

TABLE 1-continued

Anti-FLT3L Antibody Sequence Summary Table.

TABLE 1C

| Antibody Name | HCDR1 | HCDR2 | HCDR3 | LCDR1 | LCDR2 | LCDR3 |
|---|---|---|---|---|---|---|
| AM40 | SYALS (SEQ ID NO: 29) | TRPPTSRTAS YAQKFQG (SEQ ID NO: 30) | NDFVY GSYRF (SEQ ID NO: 31) | TRTSGNIA GYFVQ (SEQ ID NO: 32) | EDYQRPS (SEQ ID NO: 33) | QSYDDYRR AA (SEQ ID NO: 34) |
| SC4017 | SYALS (SEQ ID NO: 29) | TRPPTSRTAS YAQKFQG (SEQ ID NO: 30) | NDFVY GSYRF (SEQ ID NO: 31) | TRTSGWI AGYFVQ (SEQ ID NO: 35) | EDYQRPS (SEQ ID NO: 33) | QSYDDYRR AA (SEQ ID NO: 34) |
| CAT5D9 | SYALS (SEQ ID NO: 29) | GIIPVFRTAS YAQKFQG (SEQ ID NO: 36) | NNYVW GSYRF (SEQ ID NO: 37) | TRTSGNIA GYFVQ (SEQ ID NO: 32) | EDYQRPS (SEQ ID NO: 33) | QSYDDTSQG V (SEQ ID NO: 38) |
| CAT8 | SYAMS (SEQ ID NO: 39) | AISGSGGSTY YADSVKG (SEQ ID NO: 40) | SSGYYG ANFDF (SEQ ID NO: 41) | SGSSSNIG SGYVY (SEQ ID NO: 42) | RNNQRPS (SEQ ID NO: 43) | AAWDDSLSG YV (SEQ ID NO: 44) |
| CAT26 | SYAVS (SEQ ID NO: 45) | AISGSGGSTY YADSVKG (SEQ ID NO: 40) | DAYGSS WYFYY FDY (SEQ ID NO: 46) | SGSSSNIGI NPVN (SEQ ID NO: 47) | SDKYRPS (SEQ ID NO: 48) | AAWDDSLN GRV (SEQ ID NO: 49) |
| DYAX3 | MYEMR (SEQ ID NO: 50) | VIPSGGKTFY ADSVKG (SEQ ID NO: 51) | YSRWF GQLGFYS HYAMDV (SEQ ID NO: 52) | RASQSIDT YLN (SEQ ID NO: 53) | AASKLED (SEQ ID NO: 54) | QQSYSSPGIT (SEQ ID NO: 55) |
| DYAX5 | SYIMV (SEQ ID NO: 56) | SIYSSGGSTS YADSVKG (SEQ ID NO: 57) | YSRWFGQ LGFYSHY AMDV (SEQ ID NO: 52) | RASQSISS YLN (SEQ ID NO: 58) | AASSLQS (SEQ ID NO: 59) | QQSYSTPPW T (SEQ ID NO: 60) |

TABLE 1D

| Antibody Name | HC | LC |
|---|---|---|
| AM40 (amino acid) | QVQLVQSGAEVKKPGSSVKVSCK ASGGTFSSYALSWVRQAPGQGLE WMGTRPPTSRTASYAQKFQGRV TITVDESTSTGYMELSSLRSEDTA VYYCASNDFVYGSYRFWGQGTT VTVSSASTKGPSVFPLAPSSKSTS GGTAALGCLVKDYFPEPVTVSWN SGALTSGVHTFPAVLQSSGLYSLSS VVTVPSSSLGTQTYICNVNHKPSN TKVDKRVEPKSCDKTHTCPPCPAP EFEGGPSVFLFPPKPKDTLMISRTP EVTCVVVDVSHEDPEVKFNWYV DGVEVHNAKTKPREEQYNSTYRV VSVLTVLHQDWLNGKEYKCKVS NKALPASIEKTISKAKGQPREPQV YTLPPSREEMTKNQVSLTCLVKGF YPSDIAVEWESNGQPENNYKTTPP VLDSDGSFFLYSKLTVDKSRWQQ GNVFSCSVMHEALHNHYTQKSLS LSPGK (SEQ ID NO: 61) | NFMLTQPHSVSESPGKTVTISCTRTSGN IAGYFVQWYQQRPGSSPTTVIYEDYQR PSGVPDRFSGSIDSSSNSASLTISGLKTE DEADYYCQSYDDYRRAAFGGGTKLTV LGQPKAAPSVTLFPPSSEELQANKATLV CLISDFYPGAVTVAWKADSSPVKAGVE TTTPSKQSNNKYAASSYLSLTPEQWKS HRSYSCQVTHEGSTVEKTVAPTECS (SEQ ID NO: 62) |
| AM40 (DNA) | CAGGTGCAGCTGGTGCAGTCTG GGGCTGAGGTGAAGAAGCCTGG GTCCTCGGTGAAGGTCTCCTGCA AGGCTTCTGGAGGCACCTTCAG CAGTTATGCTCTTAGCTGGGTGC GACAGGCCCCTGGACAAGGGCT | AATTTTATGCTGACTCAGCCCCACTCT GTGTCGGAGTCTCCGGGGAAGACGGT AACCATCTCCTGCACCCGCACCAGTG GGAACATTGCCGGCTACTTTGTGCAGT GGTACCAGCAGCGCCCGGGCAGTTCC CCCACCACTGTGATCTATGAGGATTAC |

TABLE 1-continued

Anti-FLT3L Antibody Sequence Summary Table.

|  |  |
|---|---|
| TGAGTGGATGGGAACGCGGCCG | CAACGACCCTCTGGGGTCCCTGATCG |
| CCGACCTCCCGGACAGCAAGCT | GTTCTCTGGCTCCATCGACAGCTCCTC |
| ACGCACAGAAATTTCAGGGCAG | CAACTCTGCCTCCCTCACCATCTCTGG |
| AGTCACGATTACCGTGGACGAA | ACTGAAGACTGAGGACGAGGCTGACT |
| TCCACGAGCACAGGCTACATGG | ACTATTGTCAGTCTTATGATGACTACCG |
| AGCTGAGCAGCCTGAGATCTGA | GCGGGCGGCGTTCGGCGGAGGGACCA |
| GGACACGGCCGTGTATTACTGT | AGCTGACCGTCCTAGGTCAGCCCAAG |
| GCGTCAAACGACTTCGTGTACG | GCGGCGCCCTCGGTCACTCTGTTCCCG |
| GGAGTTATCGTTTCTGGGGCCA | CCCTCCTCTGAGGAGCTTCAAGCCAA |
| AGGGACCACGGTCACCGTCTCC | CAAGGCCACACTGGTGTGTCTCATAA |
| TCAGCGTCGACCAAGGGCCCAT | GTGACTTCTACCCGGGAGCCGTGACA |
| CCGTCTTCCCCCTGGCACCCTCC | GTGGCCTGGAAGGCAGATAGCAGCCC |
| TCCAAGAGCACCTCTGGGGGCA | CGTCAAGGCGGGAGTGGAGACCACCA |
| CAGCGGCCCTGGGCTGCCTGGT | CACCCTCCAAACAAAGCAACAACAAG |
| CAAGGACTACTTCCCCGAACCG | TACGCGGCCAGCAGCTACCTGAGCCT |
| GTGACGGTGTCCTGGAACTCAG | GACGCCTGAGCAGTGGAAGTCCCACA |
| GCGCTCTGACCAGCGGCGTGCA | GAAGCTACAGCTGCCAGGTCACGCAT |
| CACCTTCCCGGCTGTCCTACAGT | GAAGGGAGCACCGTGGAGAAGACAG |
| CCTCAGGACTCTACTCCCTCAGC | TGGCCCCTACAGAATGTTCA |
| AGCGTGGTGACCGTGCCCTCCA | (SEQ ID NO: 64) |
| GCAGCTTGGGCACCCAGACCTA |  |
| CATCTGCAACGTGAATCACAAG |  |
| CCCAGCAACACCAAGGTGGACA |  |
| AGAGAGTTGAGCCCAAATCTTG |  |
| TGACAAAACTCACACATGCCCA |  |
| CCGTGCCCAGCACCTGAATTCG |  |
| AGGGGGGACCGTCAGTCTTCCT |  |
| CTTCCCCCCAAAACCCAAGGAC |  |
| ACCCTCATGATCTCCCGGACCCC |  |
| TGAGGTCACATGCGTGGTGGTG |  |
| GACGTGAGCCACGAAGACCCTG |  |
| AGGTCAAGTTCAACTGGTACGT |  |
| GGACGGCGTGGAGGTGCATAAT |  |
| GCCAAGACAAAGCCGCGGGAGG |  |
| AGCAGTACAACAGCACGTACCG |  |
| TGTGGTCAGCGTCCTCACCGTCC |  |
| TGCACCAGGACTGGCTGAATGG |  |
| CAAGGAGTACAAGTGCAAGGTC |  |
| TCCAACAAAGCCCTCCCAGCCT |  |
| CCATCGAGAAAACCATCTCCAA |  |
| AGCCAAAGGGCAGCCCCGAGAA |  |
| CCACAGGTCTACACCCTGCCCCC |  |
| ATCCCGGGAGGAGATGACCAAG |  |
| AACCAGGTCAGCCTGACCTGCC |  |
| TGGTCAAAGGCTTCTATCCCAGC |  |
| GACATCGCCGTGGAGTGGGAGA |  |
| GCAATGGGCAGCCGGAGAACAA |  |
| CTACAAGACCACGCCTCCCGTG |  |
| CTGGACTCCGACGGCTCCTTCTT |  |
| CCTCTATAGCAAGCTCACCGTG |  |
| GACAAGAGCAGGTGGCAGCAGG |  |
| GGAACGTCTTCTCATGCTCCGTG |  |
| ATGCATGAGGCTCTGCACAACC |  |
| ACTACACGCAGAAGAGCTTAAG |  |
| CCTGTCTCCGGGTAAA |  |
| (SEQ ID NO: 63) |  |
| SC4017 (amino acid) | QVQLVQSGAEVKKPGSSVKVSCK ASGGTFSSYALSWVRQAPGQGLE WMGTRPPTSRTASYAQKFQGR VTITVDESTSTGYMELSSLRSEDT AVYYCASNDFVYGSYRFWGQGT TVTVSSASTKGPSVFPLAPSSKSTS GGTAALGCLVKDYFPEPVTVSWN SGALTSGVHTFPAVLQSSGLYSLS SVVTVPSSSLGTQTYICNVNHKPS NTKVDKRVEPKSCDKTHTCPPCP APEFEGGPSVFLFPPKPKDTLMISR TPEVTCVVVDVSHEDPEVKFNWY VDGVEVHNAKTKPREEQYNSTY RVVSVLTVLHQDWLNGKEYKCK VSNKALPASIEKTISKAKGQPREP QVYTLPPSREEMTKNQVSLTCLV KGFYPSDIAVEWESNGQPENNYK TTPPVLDSDGSFFLYSKLTVDKSR WQQGNVFSCSVMHEALHNHYTQ KSLSLSPGK (SEQ ID NO: 65) | NFMLTQPHSVSESPGKTVTISCTRTSG WIAGYFVQWYQQRPGSSPTTVIYEDY QRPSGVPDRFSGSIDSSSNSASLTISGLK TEDEADYYCQSYDDYRRAAFGGGTKL TVLGQPKAAPSVTLFPPSSEELQANKAT LVCLISDFYPGAVTVAWKADSSPVKAG VETTTPSKQSNNKYAASSYLSLTPEQW KSHRSYSCQVTHEGSTVEKTVAPTECS (SEQ ID NO: 66) |

TABLE 1-continued

Anti-FLT3L Antibody Sequence Summary Table.

| | | |
|---|---|---|
| SC4017 (DNA) | ATGGGATGGAGCTGTATCATCC TCTTCTTGGTAGCAACAGCTACA GGTAAGGGGCTCACAGTAGCAG GCTTGAGGTCTAGACATATATAT GGGTGACAATGACATCCACTTT GCCTTTCTCTCCACAGGTGTACA CTCCCAGGTGCAGCTGGTGCAG TCTGGGGCTGAGGTGAAGAAGC CTGGGTCCTCGGTGAAGGTCTCC TGCAAGGCTTCTGGAGGCACCT TCAGCAGTTATGCTCTTAGCTGG GTGCGACAGGCCCCTGGACAAG GGCTTGAGTGGATGGGAACGCG GCCGCCGACCTCCCGGACAGCA AGCTACGCACAGAAATTTCAGG GCAGAGTCACGATTACCGTGGA CGAATCCACGAGCACAGGCTAC ATGGAGCTGAGCAGCCTGAGAT CTGAGGACACGGCCGTGTATTA CTGTGCGTCAAACGACTTCGTGT ACGGGAGTTATCGTTTCTGGGG CCAAGGGACCACGGTCACCGTC TCCTCAGCGTCGACCAAGGGCC CATCCGTCTTCCCCCTGGCACCC TCCTCCAAGAGCACCTCTGGGG GCACAGCGGCCCTGGGCTGCCT GGTCAAGGACTACTTCCCCGAA CCGGTGACGGTGTCCTGGAACT CAGGCGCTCTGACCAGCGGCGT GCACACCTTCCCGGCTGTCCTAC AGTCCTCAGGACTCTACTCCCTC AGCAGCGTGGTGACCGTGCCCT CCAGCAGCTTGGGCACCCAGAC CTACATCTGCAACGTGAATCAC AAGCCCAGCAACACCAAGGTGG ACAAGAGAGTTGAGCCCAAATC TTGTGACAAAACTCACACATGC CCACCGTGCCCAGCACCTGAAT TCGAGGGGGGACCGTCAGTCTT CCTCTTCCCCCCAAAACCCAAG GACACCCTCATGATCTCCCGGA CCCCTGAGGTCACATGCGTGGT GGTGGACGTGAGCCACGAAGAC CCTGAGGTCAAGTTCAACTGGT ACGTGGACGGCGTGGAGGTGCA TAATGCCAAGACAAAGCCGCGG GAGGAGCAGTACAACAGCACGT ACCGTGTGGTCAGCGTCCTCACC GTCCTGCACCAGGACTGGCTGA ATGGCAAGGAGTACAAGTGCAA GGTCTCCAACAAAGCCCTCCCA GCCTCCATCGAGAAAACCATCT CCAAAGCCAAAGGGCAGCCCCG AGAACCACAGGTCTACACCCTG CCCCCATCCCGGGAGGAGATGA CCAAGAACCAGGTCAGCCTGAC CTGCCTGGTCAAAGGCTTCTATC CCAGCGACATCGCCGTGGAGTG GGAGAGCAATGGGCAGCCGGAG AACAACTACAAGACCACGCCTC CCGTGCTGGACTCCGACGGCTC CTTCTTCCTCTATAGCAAGCTCA CCGTGGACAAGAGCAGGTGGCA GCAGGGGAACGTCTTCTCATGC TCCGTGATGCATGAGGCTCTGC ACAACCACTACACGCAGAAGAG CTTAAGCCTGTCTCCGGGTAAA (SEQ ID NO: 67) | AATTTTATGCTGACTCAGCCCCACTCT GTGTCGGAGTCTCCGGGGAAGACGGT AACCATCTCCTGCACCCGCACCAGTG GGTGGATTGCCGGCTACTTTGTGCAG TGGTACCAGCAGCGCCCGGGCAGTTC CCCCACCACTGTGATCTATGAGGATT ACCAACGACCCTCTGGGGTCCCTGAT CGGTTCTCTGGCTCCATCGACAGCTCC TCCAACTCTGCCTCCCTCACCATCTCT GGACTGAAGACTGAGGACGAGGCTG ACTACTATTGTCAGTCTTATGATGACT ACCGGCGGGCGGCGTTCGGCGGAGGG ACCAAGCTGACCGTCCTAGGTCAGCC CAAGGCGGCGCCCTCGGTCACTCTGT TCCCGCCCTCCTCTGAGGAGCTTCAA GCCAACAAGGCCACACTGGTGTGTCT CATAAGTGACTTCTACCCGGGAGCCG TGACAGTGGCCTGGAAGGCAGATAGC AGCCCCGTCAAGGCGGGAGTGGAGAC CACCACACCCTCCAAACAAAGCAACA ACAAGTACGCGGCCAGCAGCTACCTG AGCCTGACGCCTGAGCAGTGGAAGTC CCACAGAAGCTACAGCTGCCAGGTCA CGCATGAAGGGAGCACCGTGGAGAA GACAGTGGCCCCTACAGAATGTTCA (SEQ ID NO: 68) |
| CAT5D9 (amino acid) | QVQLVQSGAEVKKPGSSVKVSCK ISGGTFSSYALSWVRQAPGQGLE WMGGIIPVFRTASYAQKFQGRV TITVDESASTGYIELSSLKSEDTAT YYCASNNYVWGSYRFWGQTT VTVSSASTKGPSVFPLAPSSKSTS GGTAALGCLVKDYFPEPVTVSWN SGALTSGVHTFPAVLQSSGLYSLS | NFMLTQPHSVSESPGKTVTISCTRTSGN IAGYFVQWYQQRPGSSPTTVIYEDYQR PSGVPDRFSGSIDRSSNSASLTISGLKPD DEADYYCQSYDDTSQGVFGAGTKVTVL (SEQ ID NO: 70) |

TABLE 1-continued

Anti-FLT3L Antibody Sequence Summary Table.

|  |  |  |
|---|---|---|
|  | SWTVPSSSLGTQTYICNVNHKPS | |
|  | NTKVDKRVEPKSCDKTHTCPPCP | |
|  | APEFEGGPSVFLFPPKPKDTLMISR | |
|  | TPEVTCVVVDVSHEDPEVKFNWY | |
|  | VDGVEVHNAKTKPREEQYNSTY | |
|  | RVVSVLTVLHQDWLNGKEYKCK | |
|  | VSNKALPASIEKTISKAKGQPREP | |
|  | QVYTLPPSREEMTKNQVSLTCLV | |
|  | KGFYPSDIAVEWESNGQPENNYK | |
|  | TTPPVLDSDGSFFLYSKLTVDKSR | |
|  | WQQGNVFSCSVMHEALHNHYTQ | |
|  | KSLSLSPGK | |
|  | (SEQ ID NO: 69) | |
| CAT5D9 (DNA) | AGGTGCAGCTGGTGCAGTCTGG | AATTTTATGCTGACTCAGCCCCACTCT |
|  | GGCTGAGGTGAAGAAGCCTGGG | GTGTCGGAGTCTCCGGGGAAGACGGT |
|  | TCCTCGGTGAAGGTCTCCTGCAA | CACCATCTCCTGCACCCGCACCAGTG |
|  | GGCTTCTGGAGGCACCTTCAGC | GGAACATTGCCGGCTACTTTGTGCAG |
|  | AGTTATGCTCTTAGCTGGGTGCG | TGGTACCAGCAGCGCCCGGGCAGTTC |
|  | ACAGGCCCCTGGACAAGGGCTT | CCCCACCACTGTGATCTATGAGGATT |
|  | GAGTGGATGGGAACGCGGCCGC | ACCAACGACCCTCTGGGGTCCCTGAT |
|  | CGACCTCCCGGACAGCAAGCTA | CGGTTCTCTGGCTCCATCGACAGGTCC |
|  | CGCACAGAAATTTCAGGGCAGA | TCCAACTCTGCCTCCCTCACCATCTCT |
|  | GTCACGATTACCGTGGACGAAT | GGACTGAAGCCTGACGACGAGGCTGA |
|  | CCACGAGCACAGGCTACATGGA | CTACTATTGTCAGTCTTATGATGACAC |
|  | GCTGAGCAGCCTGAGATCTGAG | CTCTCAAGGTGTGTTCGGCGCAGGGA |
|  | GACACGGCCGTGTATTACTGTG | CCAAGGTCACCGTCCTAGGTCAGCCC |
|  | CGTCAAACGACTTCGTGTACGG | AAGGCGGCGCCCTCGGTCACTCTGTT |
|  | GAGTTATCGTTTCTGGGGCCAA | CCCGCCCTCCTCTGAGGAGCTTCAAG |
|  | GGGACCACGGTCACCGTCTCCT | CCAACAAGGCCACACTGGTGTGTCTC |
|  | CAGCGTCGACCAAGGGCCCATC | ATAAGTGACTTCTACCCGGGAGCCGT |
|  | CGTCTTCCCCCTGGCACCCTCCT | GACAGTGGCCTGGAAGGCAGATAGCA |
|  | CCAAGAGCACCTCTGGGGGCAC | GCCCCGTCAAGGCGGGAGTGGAGACC |
|  | AGCGGCCCTGGGCTGCCTGGTC | ACCACACCCTCCAAACAAAGCAACAA |
|  | AAGGACTACTTCCCCGAACCGG | CAAGTACGCGGCCAGCAGCTACCTGA |
|  | TGACGGTGTCCTGGAACTCAGG | GCCTGACGCCTGAGCAGTGGAAGTCC |
|  | CGCTCTGACCAGCGGCGTGCAC | CACAGAAGCTACAGCTGCCAGGTCAC |
|  | ACCTTCCCGGCTGTCCTACAGTC | GCATGAAGGGAGCACCGTGGAGAAG |
|  | CTCAGGACTCTACTCCCTCAGCA | ACAGTGGCCCCTACAGAATGTTCA |
|  | GCGTGGTGACCGTGCCCTCCAG | (SEQ ID NO: 72) |
|  | CAGCTTGGGCACCCAGACCTAC | |
|  | ATCTGCAACGTGAATCACAAGC | |
|  | CCAGCAACACCAAGGTGGACAA | |
|  | GAGAGTTGAGCCCAAATCTTGT | |
|  | GACAAAACTCACACATGCCCAC | |
|  | CGTGCCCAGCACCTGAATTCGA | |
|  | GGGGGGACCGTCAGTCTTCCTCT | |
|  | TCCCCCCAAAACCCAAGGACAC | |
|  | CCTCATGATCTCCCGGACCCCTG | |
|  | AGGTCACATGCGTGGTGGTGGA | |
|  | CGTGAGCCACGAAGACCCTGAG | |
|  | GTCAAGTTCAACTGGTACGTGG | |
|  | ACGGCGTGGAGGTGCATAATGC | |
|  | CAAGACAAAGCCGCGGGAGGA | |
|  | GCAGTACAACAGCACGTACCGT | |
|  | GTGGTCAGCGTCCTCACCGTCCT | |
|  | GCACCAGGACTGGCTGAATGGC | |
|  | AAGGAGTACAAGTGCAAGGTCT | |
|  | CCAACAAAGCCCTCCCAGCCTC | |
|  | CATCGAGAAAACCATCTCCAAA | |
|  | GCCAAAGGGCAGCCCCGAGAAC | |
|  | CACAGGTCTACACCCTGCCCCC | |
|  | ATCCCGGGAGGAGATGACCAAG | |
|  | AACCAGGTCAGCCTGACCTGCC | |
|  | TGGTCAAAGGCTTCTATCCCAGC | |
|  | GACATCGCCGTGGAGTGGGAGA | |
|  | GCAATGGGCAGCCGGAGAACAA | |
|  | CTACAAGACCACGCCTCCCGTG | |
|  | CTGGACTCCGACGGCTCCTTCTT | |
|  | CCTCTATAGCAAGCTCACCGTG | |
|  | GACAAGAGCAGGTGGCAGCAGG | |
|  | GGAACGTCTTCTCATGCTCCGTG | |
|  | ATGCATGAGGCTCTGCACAACC | |
|  | ACTACACGCAGAAGAGCTTAAG | |
|  | CCTGTCTCCGGGTAAA | |
|  | (SEQ ID NO: 71) | |

Derivatives

Anti-FLT3L antibodies of the disclosure can include variants of the sequences provided that retain the ability to specifically bind FLT3L. Such variants can be derived from the sequences of the antibodies by a skilled artisan using techniques well known in the art. For example, amino acid substitutions, deletions, or additions, can be made in the FR regions and/or in the CDRs of the anti-FLT3L antibodies that do prevent binding of the antibodies to their epitopes. While changes in the FRs are usually designed to improve stability and immunogenicity of the antigen binding domain, changes in the CDRs are typically designed to increase affinity of the antigen binding domain for its target. Variants of FRs also include naturally occurring immunoglobulin allotypes. Such affinity-increasing changes may be determined empirically by routine techniques that involve altering the CDR and testing the affinity of the antigen binding domain for its target. For example, conservative amino acid substitutions can be made within any one of the disclosed CDRs. Various alterations can be made according to the methods described in Antibody Engineering, 2nd ed., Oxford University Press, ed. Borrebaeck, 1995. These alterations include but are not limited to nucleotide sequences that are altered by the substitution of different codons that encode a functionally equivalent amino acid residue within the sequence, thus producing a "silent" change. For example, the nonpolar amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid.

Derivatives and analogs of antibodies of the disclosure can be produced by various techniques well known in the art, including recombinant and synthetic methods (Maniatis (1990) Molecular Cloning, A Laboratory Manual, 2nd ed., Cold Spring Harbor Laboratory, Cold Spring Harbor, N.Y., and Bodansky et al. (1995) The Practice of Peptide Synthesis, 2nd ed., Spring Verlag, Berlin, Germany).

In one embodiment, a method for making a VH domain which is an amino acid sequence variant of a VH domain of the disclosure comprises a step of adding, deleting, substituting, or inserting one or more amino acids in the amino acid sequence of the presently disclosed VH domain, optionally combining the VH domain thus provided with one or more VL domains, and testing the VH domain or VH/VL combination or combinations for specific binding to the antigen. An analogous method can be employed in which one or more sequence variants of a VL domain disclosed herein are combined with one or more VH domains.

Analogous shuffling or combinatorial techniques are also disclosed by Stemmer (Nature (1994) 370: 389-391), who describes the technique in relation to a β-lactamase gene but observes that the approach may be used for the generation of antibodies.

In further embodiments, one may generate novel VH or VL regions carrying one or more sequences derived from the sequences disclosed herein using random mutagenesis of one or more selected VH and/or VL genes. One such technique, error-prone PCR, is described by Gram et al. (Proc. Nat. Acad. Sci. U.S.A. (1992) 89: 3576-3580).

Another method that may be used is to direct mutagenesis to CDRs of VH or VL genes. Such techniques are disclosed by Barbas et al. (Proc. Nat. Acad. Sci. U.S.A. (1994) 91: 3809-3813) and Schier et al. (J. Mol. Biol. (1996) 263: 551-567).

Similarly, one, two, or all three CDRs of an antigen binding domain may be grafted into a repertoire of VH or VL domains, which are then screened for an antigen-binding fragment specific for FLT3L.

A portion of an immunoglobulin variable domain useful herein can comprise at least one of the CDRs substantially as set out herein and, optionally, intervening framework regions from the scFv fragments as set out herein. The portion may include at least about 50% of either or both of FR1 and FR4, the 50% being the C-terminal 50% of FR1 and the N-terminal 50% of FR4. Additional residues at the N-terminal or C-terminal end of the substantial part of the variable domain can be those not normally associated with naturally occurring variable domain regions. For example, construction of antibodies by recombinant DNA techniques can result in the introduction of N- or C-terminal residues encoded by linkers introduced to facilitate cloning or other manipulation steps. Other manipulation steps include the introduction of linkers to join variable domains to further protein sequences including immunoglobulin heavy chain constant regions, other variable domains (for example, in the production of diabodies), or proteinaceous labels as discussed in further detail below.

Antigen binding domains of the disclosure described herein can be linked to another functional molecule, e.g., another peptide or protein (albumin, another antibody, etc.). For example, the antigen binding domains can be linked by chemical cross-linking or by recombinant methods. The antigen binding domains can also be linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337. The antigen binding domains can be chemically modified by covalent conjugation to a polymer, for example, to increase their circulating half-life. Exemplary polymers and methods to attach them are also shown in U.S. Pat. Nos. 4,766,106; 4,179,337; 4,495,285, and 4,609,546.

The disclosed antibodies can also be altered to have a glycosylation pattern that differs from the native pattern. For example, one or more carbohydrate moieties can be deleted and/or one or more glycosylation sites added. Addition of glycosylation sites to the presently disclosed antibody fragments can be accomplished by altering the amino acid sequence to contain glycosylation site consensus sequences known in the art. Another means of increasing the number of carbohydrate moieties on the antibody fragments is by chemical or enzymatic coupling of glycosides to the amino acid residues of the antibody. Such methods are described in WO 87/05330, and in Aplin et al. (1981) CRC Crit. Rev. Biochem., 22: 259-306. Removal of any carbohydrate moieties from the antibodies may be accomplished chemically or enzymatically, for example, as described by Hakimuddin et al. (1987) Arch. Biochem. Biophys., 259: 52; and Edge et al. (1981) Anal. Biochem., 118: 131 and by Thotakura et al. (1987) Meth. Enzymol., 138: 350. The antibody fragments may also be tagged with a detectable, or functional, label. Detectable labels include radiolabels such as 131I or 99Tc, which may also be attached to antibody fragments using conventional chemistry. Detectable labels also include enzyme labels such as horseradish peroxidase or alkaline phosphatase. Detectable labels further include chemical moieties such as biotin, which may be detected via binding to a specific cognate detectable moiety, e.g., labeled avidin.

Antigen binding domains, in which CDR sequences differ only insubstantially from those set forth herein are encompassed within the scope of this disclosure. Typically, an amino acid is substituted by a related amino acid having similar charge, hydrophobic, or stereochemical characteristics. Such substitutions would be within the ordinary skills of an artisan. Unlike in CDRs, more substantial changes can be made in FRs without adversely affecting the binding properties of an antibody. Changes to FRs include, but are not limited to, humanizing a non-human derived or engineering certain framework residues that are important for antigen contact or for stabilizing the binding site, e.g., changing the class or subclass of the constant region, changing specific amino acid residues which might alter the effector function such as Fc receptor binding, e.g., as described in U.S. Pat. Nos. 5,624,821 and 5,648,260 and Lund et al. (1991) J. Immun. 147: 2657-2662 and Morgan et al. (1995) Immunology 86: 319-324, or changing the species from which the constant region is derived.

One of skill in the art will appreciate that the modifications described above are not all-exhaustive, can be applied to the protein subunits described herein, and that many other modifications would be possible for a skilled artisan in light of the teachings of the present disclosure.

Anti-FLT3L Antibody Affinity and Specificity

One of skill in the art will recognize that anti-FLT3L antibodies for use in autoimmune disease require high affinity binding, yet must lack toxicity that prevents their use in humans. Structurally similar homologues of FLT3L include stem-cell factor (SCF, also known as KIT-ligand) and colony stimulating factor 1 (CSF1, also known as macrophage colony-stimulating factor "M-CSF"). A non-specific anti-FLT3L antibody that binds FLT3L and also binds SCF and CSF1 can result in off-target toxicity. Thus the anti-FLT3L antibodies of the present disclosure retain binding specificity to only FLT3L, but not structurally similar cytokines such as SCF and CSF1. One skilled in art would know to use, but not be limited to, binding kinetics, including $K_{on}$, $K_{off}$ and $K_D$ as measures of binding specificity.

Serum FLT3L and circulating pDC are biomarkers that can be used as an indicator of toxicity associated with anti-FLT3L antibody lead clones. A rapid drop in pDC when FLT3L is neutralized indicates suppression of FLT3L-mediated cell signaling that enhances the immune response. A rapid recovery of pDC frequency in the presence of free FLT3L can reflect a lack of toxicity in the anti-FLT3L antibody. In a preferred embodiment, the anti-FLT3L antibody neutralizes FLT3L and allows reversible depletion of cDC and pDC when free FLT3L returns. One skilled in the art will recognize that a drop in dendritic cells upon neutralization of FLT3L, followed by return to baseline is indicative of low toxicity of the lead clone.

Anti-FLT3L Antibody Production

The practice of the present disclosure employs, unless otherwise indicated, techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polypeptides of the disclosure, and, as such, may be considered in making and practicing the disclosure. Particularly useful techniques for particular embodiments will be discussed in the Examples.

In one embodiment, an isolated nucleic acid molecule encoding an anti-FLT3L antibody or antigen-binding fragment thereof is operably linked to one or more control sequences for expression in a host cell. The isolated nucleic acid can be recombinantly incorporated into a vector, which in turn is transfected into the host cell using known techniques.

In one embodiment, host cells transformed with an isolated nucleic acid molecule encoding an anti-FLT3L antibody or antigen-binding fragment thereof that is operably linked to one or more control sequences are contemplated herein. Examples of contemplated host cells include mammalian cells, such as a HEK293 cell, an NS0 murine myeloma cell, or a Chinese hamster ovary (CHO) cell.

In one embodiment, monoclonal anti-FLT3L antibodies (e.g., CAT5D9, SC4017, or AM40) and antigen-binding fragments thereof can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen.

In another embodiment, lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (RIA); enzyme-linked immunosorbent assay (ELISA)) can then be propagated either in in vitro culture using standard methods (Coding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively anti-FLT3L monoclonal antibodies (e.g., CAT5D9, SC4017, or AM40) and antigen-binding fragments thereof can also be made using recombinant DNA methods as described, for example, in U.S. Pat. No. 4,816,567. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant anti-FLT3L monoclonal antibodies or antigen-binding fragments thereof of the desired species can be isolated from phage display libraries expressing CDRs of the desired species as described (McCafferty et al., 1990, Nature, 348:552-554; Clarkson et al., 1991, Nature, 352:624-628; and Marks et al., 1991, J. Mol. Biol., 222:581-597).

The polynucleotide(s) encoding an anti-FLT3L antibody or antigen-binding fragment thereof can further be modified in a number of different manners using recombinant DNA technology to generate alternative antibodies. In some aspects, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some aspects, the constant regions are truncated or removed to generate the desired antibody fragment of a monoclonal antibody. Site-directed or high-density mutagenesis of the variable region can be used to optimize specificity, affinity, etc. of a monoclonal antibody.

In certain aspects, the anti-FLT3L antibody or antigen-binding fragment thereof is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373).

Also, the anti-FLT3L human antibody or antigen-binding fragment thereof can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227: 381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety).

Affinity maturation strategies and chain shuffling strategies (Marks et al., 1992, Bio/Technology 10:779-783, incorporated by reference in its entirety) are known in the art and can be employed to generate high affinity human antibodies or antigen-binding fragments thereof.

In some aspects, the anti-FLT3L monoclonal antibody can be a humanized antibody. Methods for engineering, humanizing, or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate, or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing FLT3L binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the FLT3L antigen and other favorable biological properties. To achieve this goal, humanized (or human) or engineered anti-FLT3L antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as FLT3L. In this way, framework (FW) residues can be selected and combined from the consensus and import sequences so that the desired antibody characteristic, such as increased affinity for the target antigen(s), is achieved.

Humanization, resurfacing or engineering of anti-FLT3L antibodies or antigen-binding fragments thereof can be performed using any known method, such as but not limited to those described in, Jones et al., Nature 321:522 (1986); Riechmann et al., Nature 332:323 (1988); Verhoeyen et al., Science 239: 1534 (1988)), Sims et al, J. Immunol. 151: 2296 (1993); Chothia and Lesk, J. Mol. Biol. 196:901 (1987), Carter et al, Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817, 483; 5,814,476; 5,763,192; 5,723,323; 5,766,886; 5,714, 352; 5,9,55,358; 6,204,023; 6,180,370; 6,331,431; 5,693, 762; 5,530,101; 5,585,089; 5,225,539; 4,816,567; 5,969, 108; 7,635,666; 7,723,270; 7,557,189; 7,538,195; and 7,342,110; International Application Nos. PCT/US98/16280; PCT/US91/05939; PCT/US94/01234; PCT/GB92/01755; International Patent Application Publication Nos. WO90/14443; WO90/14424; WO90/14430; and European Patent Publication No. EP 229246; each of which is entirely incorporated herein by reference, including the references cited therein.

Anti-FLT3L humanized antibodies and antigen-binding fragments thereof can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633, 425; and 5,661,016.

In certain aspects an anti-FLT3L antibody fragment is provided. Various techniques are known for the production of antibody fragments. Traditionally, these fragments are derived via proteolytic digestion of intact antibodies (for example Morimoto et al, 1993, Journal of Biochemical and Biophysical Methods 24: 107-117; Brennan et al, 1985, Science, 229:81). In certain aspects, anti-FLT3L antibody fragments are produced recombinantly. Fab, Fv, and scFv antibody fragments can all be expressed in and secreted from E. coli or other host cells, thus allowing the production of large amounts of these fragments. Such anti-FLT3L antibody fragments can also be isolated from the antibody phage libraries discussed above. The anti-FLT3L antibody fragments can also be linear antibodies as described in U.S. Pat. No. 5,641,870. Other techniques for the production of antibody fragments, e.g., chemical synthesis, will be apparent to the skilled practitioner.

According to the present disclosure, techniques can be adapted for the production of single-chain antibodies specific to FLT3L (see, e.g., U.S. Pat. No. 4,946,778). In addition, methods can be adapted for the construction of Fab expression libraries (see, e.g., Huse et al., *Science* 246: 1275-1281 (1989)) to allow rapid and effective identification of monoclonal Fab fragments with the desired specificity for FLT3L, or derivatives, fragments, analogs or homologs thereof. Antibody fragments can be produced by techniques in the art including, but not limited to: (a) a F(ab')$_2$ fragment produced by pepsin digestion of an antibody molecule; (b) a Fab fragment generated by reducing the disulfide bridges of an F(ab')$_2$ fragment, (c) a Fab fragment generated by the treatment of the antibody molecule with papain and a reducing agent, and (d) Fv fragments.

An anti-FLT3L antibody or an antigen-binding fragment thereof disclosed herein can be modified in order to increase its serum half-life. This can be achieved, for example, by incorporation of a salvage receptor binding epitope into the antibody or antibody fragment by mutation of the appropriate region in the antibody or antibody fragment or by incorporating the epitope into a peptide tag that is then fused to the antibody or antibody fragment at either end or in the middle (e.g., by DNA or peptide synthesis), or by YTE mutation. Other methods to increase the serum half-life of an antibody or antigen-binding fragment thereof, e.g., conjugation to a heterologous molecule such as PEG are known in the art.

Pharmaceutical Compositions

The present invention is also directed to pharmaceutical compositions comprising the anti-FLT3L antibodies or antigen-binding fragment thereof disclosed herein. In certain embodiments, the present disclosure provides for the use of an anti-FLT3L antibody or an antigen-binding fragment thereof disclosed herein in the manufacture of a medicament for treating a subject.

An effective amount of the pharmaceutical composition of the disclosure should be administered, in which "effective amount" is defined as an amount that is sufficient to produce a desired prophylactic, therapeutic or ameliorative response in a subject. The effective amount will vary depending upon the species and weight of the subject to be administered, but may be ascertained using standard techniques.

In certain aspects, the present disclosure provides therapeutic and prophylactic compositions for use in subjects in need thereof in the treatment or prevention (reducing the likelihood) of autoimmune diseases including, without limitation, systemic lupus erythematosus, myositis, primary Sjögren's Syndrome, multiple sclerosis, uveitis, psoriasis, or rheumatoid arthritis.

In some embodiments, a pharmaceutical composition of the disclosure comprises an anti-FLT3L antibody or an antigen-binding fragment thereof disclosed herein and one or more pharmaceutically acceptable carriers, diluents, or excipients. In this regard, "pharmaceutically acceptable carriers, diluents, or excipients" include but are not limited to any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that may or may not have been approved by the United States Food and Drug Administration as being acceptable for use in humans or domestic animals. For example, appropriate carriers are known to those skilled in the art and include stabilizers, diluents, and buffers. Suitable stabilizers include carbohydrates, such as sorbitol, lactose, mannitol, starch, sucrose, dextran, and glucose, and proteins, such as albumin or casein. Suitable diluents include saline, Hanks Balanced Salts, and Ringers solution. Suitable buffers include an alkali metal phosphate, an alkali metal carbonate, or an alkaline earth metal carbonate.

In certain aspects, the pharmaceutical compositions of the disclosure may further contain one or more auxiliary substance, such one or more lipids, phospholipids, carbohydrates, and lipopolysaccharides. In some embodiments, pharmaceutical compositions of the disclosure optionally comprise one or more additional active substances.

In certain cases, the pharmaceutical compositions of the present disclosure can be prepared by techniques known to those skilled in the art. General considerations in the formulation and/or manufacture of pharmaceutical compositions may be found, for example, in Remington: The Science and Practice of Pharmacy 21st ed., Lippincott Williams & Wilkins, 2005 (incorporated herein by reference in its entirety). Generally, an anti-FLT3L antibody or antigen-binding fragment thereof of the disclosure is mixed with a carrier to form a solution, suspension, or emulsion. One or more of the additives discussed herein may be added in the carrier or may be added subsequently. The pharmaceutical compositions of the disclosure may be an aqueous solution, emulsion or suspension or may be a dried preparation. In certain aspects, the pharmaceutical compositions of the disclosure may be desiccated or lyophilized, for example, by freeze drying or spray drying for storage or formulations purposes. They may be subsequently reconstituted into liquid compositions by the addition of an appropriate liquid carrier or administered in dry formulation using methods known to those skilled in the art.

The pharmaceutical compositions of the disclosure may be administered to a subject via a variety of routes known in the art. Exemplary routes of administering of such pharmaceutical compositions include oral, mucosal, topical, transdermal, inhalation, parenteral, sublingual, buccal, rectal, vaginal, and intranasal. Thus, in certain embodiments, a pharmaceutical composition of the disclosure is formulated to be administered by routes selected from the group consisting of oral, topical, transdermal, inhalation, parenteral, sublingual, buccal, rectal, vaginal, and intranasal routes. The term parenteral, as used herein, includes subcutaneous injections, intravenous, intramuscular, intrasternal injection or infusion techniques. In certain aspects, pharmaceutical compositions of the disclosure are formulated to allow an anti-FLT3L antibody or antigen-binding fragment thereof of the disclosure contained therein to be bioavailable upon administration to a subject.

The choice of administration of the pharmaceutical composition will depend on the formulation that is selected. The pharmaceutical compositions of the disclosure are administered in a manner compatible with the dosage formulation, and in such amount as will be therapeutically effective. In certain aspects, a pharmaceutical composition of the disclosure is formulated into preparations in solid, semi-solid, liquid or gaseous forms, including, but not limited to, tablets, capsules, powders, granules, ointments, solutions, suppositories, injections, inhalants, gels, microspheres, and aerosols.

In certain instances, a pharmaceutical composition comprising an anti-FLT3L antibody or an antigen-binding fragment thereof disclosed herein may be in the form of a solid or liquid. In some aspects, the carrier(s) are particulate so that the compositions are, for example, in tablet or powder form. In other aspects, the carrier(s) are liquid, with a composition being, for example, an oral syrup, injectable liquid or an aerosol, which is useful in, for example, inhalatory administration. When intended for oral administration, a pharmaceutical composition comprising an anti-FLT3L antibody or an antigen-binding fragment thereof disclosed herein is in either solid or liquid form, where semi-solid, semi-liquid, suspension and gel forms are included within the forms considered herein as either solid or liquid.

In certain aspects, as a solid composition for oral administration, a pharmaceutical composition comprising an anti-FLT3L antibody or an antigen-binding fragment thereof of disclosed herein may be formulated into a powder, granule, compressed tablet, pill, capsule, chewing gum, wafer or the like form. In some instances, such a solid composition will typically contain one or more inert diluents or edible carriers. In certain embodiments, one or more of the following may be additionally present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

These compositions can take the form of microspheres, solutions, suspensions, tablets, pills, capsules, sustained release formulations or powders and contain about 0.001 to 95% of an anti-FLT3L antibody or an antigen-binding fragment thereof disclosed herein. Some dosage forms may contain 50 µg to 250 µg of the anti-FLT3L antibody or antigen-binding fragment thereof.

In some aspects, when a pharmaceutical composition of the disclosure is in the form of a capsule, for example, a gelatin capsule, it may contain, in addition to materials disclosed herein, a liquid carrier such as polyethylene glycol or oil. Oral formulations may also include normally employed excipients such as, for example, pharmaceutical grades of saccharine, cellulose and magnesium carbonate.

In other aspects, a pharmaceutical composition of the disclosure is in the form of a liquid, for example, an elixir, syrup, solution, emulsion or suspension. In certain embodiments, the liquid may be for oral administration or for delivery by injection. In certain embodiments, when intended for oral administration, the pharmaceutical compositions of the disclosure contain, in addition to an anti-FLT3L antibody or an antigen-binding fragment thereof disclosed herein, one or more of a sweetening agent, preservatives, dye/colorant and flavor enhancer. In certain aspects, in a pharmaceutical composition intended to be administered by injection, one or more of a surfactant, preservative, wetting agent, dispersing agent, suspending agent, buffer, stabilizer and isotonic agent may be included.

In certain cases, liquid pharmaceutical compositions comprising an anti-FLT3L antibody or an antigen-binding fragment thereof disclosed herein, whether they be solutions, suspensions or other like form, may include one or more of the following components: sterile diluents such as water for injection, saline solution, e.g., physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. In some cases, the preparation can be enclosed in ampoules, disposable syringes or multiple dose vials made of glass or plastic. In some embodiments, an injectable pharmaceutical composition is preferably sterile.

In other embodiments, a pharmaceutical composition comprising an anti-FLT3L antibody or an antigen-binding fragment thereof disclosed herein may be intended for topical administration, in which case the carrier may suitably comprise a solution, emulsion, ointment or gel base. In certain aspects, the base, for example, may comprise one or more of the following: petrolatum, lanolin, polyethylene glycols, bee wax, mineral oil, diluents such as water and alcohol, and emulsifiers and stabilizers. In other aspects, thickening agents may be present in a pharmaceutical composition for topical administration. In certain embodiments, if intended for transdermal administration, a pharmaceutical composition of an anti-FLT3L antibody or an antigen-binding fragment thereof disclosed herein may be included with a transdermal patch or iontophoresis device.

In yet other embodiments, the pharmaceutical composition comprising an anti-FLT3L antibody or an antigen-binding fragment thereof disclosed herein is intended for rectal administration, in the form, for example, of a suppository. For suppositories, binders and carriers may include, for example, polyalkalene glycols or triglycerides. In certain instances, a composition for rectal administration contains an oleaginous base as a suitable nonirritating excipient. Such bases include, without limitation, lanolin, cocoa butter or polyethylene glycol.

In other aspects, a pharmaceutical composition comprising an anti-FLT3L antibody or an antigen-binding fragment thereof disclosed herein comprises dosage units that can be administered as an aerosol. The term aerosol is used to denote a variety of systems ranging from those of colloidal nature to systems consisting of pressurized packages. In certain embodiments, delivery is accomplished by a liquefied or compressed gas or by a suitable pump system that dispenses the active ingredients. In some embodiments, aerosols of an anti-FLT3L antibody or an antigen-binding fragment thereof disclosed herein may be delivered in single phase, bi-phasic, or tri-phasic systems in order to deliver the active ingredient(s). In other embodiments, delivery of the aerosol includes the necessary container, activators, valves, subcontainers, and the like, which together may form a kit. One skilled in the art can readily determine specific aerosol formulations and delivery modes.

Pharmaceutical compositions of the disclosure may be administered in a suitable, nontoxic pharmaceutical carrier, may be comprised in microcapsules, microbeads, and/or may be comprised in a sustained release implant.

In other aspects, a pharmaceutical composition of the disclosure includes materials that form a coating shell around the active ingredients. In some instances, the materials that form the coating shell are typically inert, and may be selected from, for example, sugar, shellac, and other enteric coating agents.

In yet other aspects, the pharmaceutical compositions of the disclosure in solid or liquid form include an agent that binds to an anti-FLT3L antibody or an antigen-binding fragment thereof disclosed herein and thereby assist in the delivery of the anti-FLT3L antibody or an antigen-binding fragment thereof. In certain cases, suitable agents that act in this capacity include a protein or a liposome.

In certain aspects, pharmaceutical compositions that will be administered to a subject take the form of one or more dosage units, where, for example, a tablet may be a single dosage unit, and a container of an anti-FLT3L antibody or an antigen-binding fragment thereof disclosed herein in aerosol form may hold a plurality of dosage units. Actual methods of preparing such dosage forms are known, or will be apparent to those skilled in this art; for example, see Remington: The Science and Practice of Pharmacy, 20th Edition (Philadelphia College of Pharmacy and Science, 2000). A composition to be administered will, in any event, contain a therapeutically effective amount of an anti-FLT3L antibody or an antigen-binding fragment thereof disclosed herein, or a pharmaceutically acceptable salt thereof, to aid in treatment of a disease or condition of interest in accordance with the teachings herein.

In certain embodiments, the pharmaceutical compositions of the disclosure comprise one or more additional therapeutically active substances. In other embodiments, a therapeutically effective dose of the pharmaceutical compositions of the disclosure is administered to a subject in need thereof in combination with one or more additional therapeutically active substances. As used herein, a "combination" refers to a combination comprising an anti-FLT3L antibody or an antigen-binding fragment thereof disclosed herein and one or more additional therapeutically active substances, each of which may be administered serially (sequentially), concurrently or simultaneously.

Pharmaceutical compositions of the disclosure may desirably be administered at several intervals in order to sustain therapeutic levels. Pharmaceutical compositions of the disclosure may be used in conjunction with other bactericidal or bacteriostatic methods.

Although the descriptions of pharmaceutical compositions provided herein are principally directed to pharmaceutical compositions which are suitable for administration to humans, it will be understood by the skilled artisan that such compositions are generally suitable for administration to subjects of all sorts. In certain aspects, the subject is a mammal. In certain aspects, a mammal includes primates, such as humans, monkeys and apes, and non-primates such as domestic animals, including laboratory animals and household pets and farm animals (e.g., cats, dogs, swine, cattle, sheep, goats, horses, rabbits), and non-domestic animals, such as wildlife, birds, or the like.

Autoimmune/Anti-Inflammatory Therapy

The present disclosure also features compositions and methods that are useful for treating autoimmune and/or other inflammatory diseases (i.e., diseases involving over-reactive and/or malfunctioning immune systems) comprising anti-FLT3L antibodies, such as those described above. In various embodiments, the anti-FLT3L antibodies can be administered in combination with other immunoregulatory drugs designed to inhibit or attenuate a subject's immune system or a specific immune response to a particular antigen or set of antigens and thereby reduce or prevent an autoimmune or other inflammatory disease.

Further provided herein are methods for treating autoimmune and/or other inflammatory diseases including administration of one or more anti-FLT3L antibodies. As shown herein, administration of anti-FLT3L antibodies can result in at least one of a reduction in an immune response, the expression of one or more immunological signaling cascades, or the reduction in immune cell populations. In certain aspects, a patient or subject presenting with an autoimmune disease or other inflammatory disease is administered an anti-FLT3L antibody.

Treatment with an autoimmune and/or other inflammatory disease therapy including an anti-FLT3L antibody causes, for example, a reduction in the rate of progression of the autoimmune disease or inflammatory disease, a retardation or stabilization of immune cell proliferation, lesion shrinkage (e.g., such as in MS patients), and/or disease regression. In some aspects, metrics measuring the reduction or retardation of autoimmune disease or inflammatory disease (e.g., reduced inflammation, levels of inflammatory cytokines, immune cell populations, and/or associated damage, such as tissue lesions) can be statistically significant. A reduction in metrics of autoimmune disease or inflammatory disease can be measured by comparison to the level of patient's metrics at baseline (pre-treatment) against an expected level of the individual's disease progression, against an expected level of disease progression based on a large patient population, or against the expected level of disease progression of a control population.

In one embodiment, a method of treatment as contemplated herein includes the application or administration of an anti-FLT3L binding molecule, antibody, or antigen binding fragment, variant, or derivative thereof of the current disclosure to a subject or patient, or application or administration of the anti-FLT3L binding molecule to an isolated tissue or cell line from a subject or patient, where the subject or patient has a disease, a symptom of a disease, or a predisposition toward a disease.

Contemplated diseases include acute or chronic inflammatory diseases including Type 1 and Type 2 diabetes, CKD, including, for example, CKD caused by diabetes, diabetic nephropathy, and high blood pressure, atherosclerosis, Alzheimer's disease, cancer, and associated complications of such diseases, including heart disease, hypertension, anemia, pericarditis, renal osteodystrophy, and others. Additional contemplated diseases include autoimmune diseases, including, without limitation, systemic lupus erythematosus, myositis, primary Sjögren's Syndrome, multiple sclerosis, uveitis, psoriasis, and rheumatoid arthritis.

In another embodiment, treatment is also intended to include the application or administration of a pharmaceutical composition including the anti-FLT3L binding molecule, e.g., an antibody or antigen binding fragment, variant, or derivative thereof of the current disclosure to a subject or patient, or application or administration of a pharmaceutical composition comprising the anti-FLT3L binding molecule to an isolated tissue or cell line from a subject or patient, who has a disease, a symptom of a disease, or a predisposition toward a disease.

In accordance with the methods of the present disclosure, at least one anti-FLT3L an antibody as defined elsewhere herein is used to promote a positive therapeutic response with respect to an autoimmune or inflammatory disease. The term "positive therapeutic response" refers to a reduction in symptoms associated with an autoimmune or inflammatory disease. Thus, for example, an improvement in the disease can be characterized as a complete response. By "complete response" is intended an absence of clinically detectable disease with normalization of any previously test results. Alternatively, an improvement in the disease can be categorized as being a partial response. A "positive therapeutic response" encompasses a reduction or inhibition of the progression and/or duration of autoimmune or inflammatory disease, the reduction or amelioration of the severity of an autoimmune or inflammatory disease, and/or the amelioration of one or more symptoms thereof resulting from the administration of an anti-FLT3L binding molecule disclosed herein.

In certain embodiments is provided a method for treating primary Sjögren's Syndrome, comprising: administering to a subject in need thereof a pharmaceutically effective amount of an antibody or antigen-binding fragment thereof disclosed herein.

In other embodiments is provided a method for treating myositis, comprising: administering to a subject in need thereof a pharmaceutically effective amount of an antibody or antigen-binding fragment thereof disclosed herein.

In certain embodiments is provided a method for treating systemic lupus erythematosus (SLE), comprising: administering to a subject in need thereof a pharmaceutically effective amount of an antibody or antigen-binding fragment thereof disclosed herein. In some aspects, the subject has increased serum levels FLT3L, as measured by frequency of FLT3L-expressing CD4+ T cells, compared to a healthy subject.

In some embodiments is provided a method for diagnosing systemic lupus erythematosus (SLE) in a subject, comprising (a) measuring serum levels of FLT3L, or (b) measuring frequency of FLT3L-expressing CD4+ T cells, wherein increased serum levels of FLT3L or increased frequency of FLT3L-expressing CD4+ T cells in the subject compared to a healthy donor indicates that the subject has SLE. In certain aspects, the CD4+ T cells are effector memory cells ($T_{EM}$).

In some embodiments is provided a method of neutralizing membrane bound FLT3L in a subject in need thereof, the method comprising administering to the subject a pharmaceutically effective amount of an antibody or antigen-binding fragment thereof disclosed herein. In certain aspects, the FLT3L is reversibly neutralized such that the activity of membrane-bound FLT3L can return to "pre-administration" levels.

In other embodiments is provided a method of neutralizing soluble FLT3L in a subject in need thereof, the method comprising administering to the subject a pharmaceutically effective amount of an anti-FLT3L antibody or antigen-binding fragment thereof disclosed herein. In certain aspects, the FLT3L is reversibly neutralized such that the levels of soluble FLT3L can return to pre-administration levels.

In specific embodiments, the method of neutralizing soluble FLT3L further comprises administering to the subject an anti-FLT3L antibody or antigen-binding fragment thereof subcutaneously, once a week, at a range of between about 0.03 mg/kg and about 30 mg/kg. In other embodiments, the method further comprises administering to the subject an anti-FLT3L antibody or antigen-binding fragment thereof subcutaneously, once every four weeks, at a dose of about 150 mg/kg.

In other embodiments is provided a method of reducing populations of circulating classical dendritic cells (cDCs) and plasmacytoid dendritic cells (pDCs) in a subject in need thereof, the method comprising administering to the subject a pharmaceutically effective amount of an antibody or antigen-binding fragment thereof disclosed herein. In certain aspects, the populations of cDCs and pDCs are reversibly reduced such that the populations of cDC and pDC are capable of returning to pre-administration levels.

In certain embodiments is provided a method of reducing FLT3L expression on CD4+ T cells, comprising administering to a subject in need thereof a pharmaceutically effective amount of an antibody or antigen-binding fragment thereof disclosed herein.

In other embodiments is provided a method of reducing the percentage of CD4+ T cells expressing FLT3L, comprising administering to a subject in need thereof a pharmaceutically effective amount of an antibody or antigen-binding fragment thereof disclosed herein.

In other embodiments is provided a method of reducing ERK signaling in a lymphoblast, comprising contacting the lymphoblast with an antibody or antigen-binding fragment thereof disclosed herein.

In certain embodiments is provided a method of reducing MEK 1/2 phosphorylation in primary CD133+ human stem cells, comprising contacting the stem cells with an antibody or antigen-binding fragment thereof disclosed herein.

The following examples are put forth so as to provide those of ordinary skill in the art with a complete disclosure and description of how to make and use the assay, screening, and therapeutic methods of the disclosure, and are not intended to limit the scope of what the inventors regard as their disclosure.

EXAMPLES

The current disclosure is described with reference to the following examples. The examples are illustrative only, and the disclosure should in no way be construed as being limited to these examples but rather should be construed to encompass any and all variations which become evident as a result of the teachings provided herein.

Example No. 1. Anti-FLT3L Antibody Generation

Overview:

FLT3L is a 65 kDa non-disulphide-linked homodimeric glycoprotein. Ligand and receptor sequence homology for humans, non-human primates, and mouse are shown below in Table 2.

TABLE 2

| Identity to human FLT3 and FLT3L | | |
|---|---|---|
| | FLT3 | FLT3-L ECD |
| Cyno | 96% | 95% |
| Rhesus | 97% | 96% |
| Mouse | 85% | 73% |

Though homology of complete mouse FLT3L protein is only 73%, its binding site with FLT3 is highly conserved amongst species. Indeed, human FLT3L binds and activates mouse FLT3 and vice versa. FLT3L has structural homology to stem cell factor (SCF or KIT-ligand) and colony stimulating factor 1 (CSF1), but no significant sequence homology to other human cytokines. The receptors for these two ligands, c-KIT and CSF1R, respectively, are also class III TKRs that commonly interact with inhibitors of FLT3, leading to undesired off-target toxicity in clinical use. With these considerations, antibodies were sought for FLT3L that would not cross-react with SCF or CSF1, providing highly specific inhibition of the FLT3/FLT3L pathway.

Lead antibodies were selected and tested using alternating selections on soluble human and mouse FLT3-L. Primary biochemical high throughput screens were performed using Human FLT3/FLT3L competition completion Homogenous Time Resolved Fluorescence (HTRF) assays. All single-chain variable fragment-fragment crystalline region (scFv-Fc) hits were converted to an IgG1 TM format and a functional screening assay using FLT3 downregulation on the target cell surface was then used to confirm inhibitory activity of the lead antibodies. Mouse and cynomolgus monkey cross-reactivity and selectivity for FLT3L and exclusion of other family members, such as stem cell factor (scf), was confirmed using ELISA and functional assays.

Lead compounds were further assessed using FLT3 signaling assays in RS4;11 cell lines and primary human CD133+ stem cells. Binding to endogenous FLT3L was confirmed using primary human T cells. The specific binding site and binding affinities were determined via Octet and BIAcore, respectively. The resultant lead antibody clone was selected for further optimization, as described below.

Lead Antibody Candidate Identification Campaign (C5, B10-11)

Lead antibodies for anti-FLT3L binding studies were generated by first screening phage libraries as shown in FIG. 1. The phage display libraries Bone Marrow Vaughan (BMV), combined spleen (CS), DP47 library (DP47), and the Dyax human antibody library were panned (alternative panning or competition panning) against human FLT3L (huFLT3L) and/or mouse FLT3L (muFLT3L). Briefly, in-house produced FLT3L was labeled with biotin using EZ-Link Sulfo-NHS-LC-Biotin labelling kit (Thermo Scientific) as the panning antigen. Panning was carried out for two to three rounds with in-house scFv libraries as described (Xiao X et al., 2017 mAbs 542 9, 996-1006 (2017)). To enhance human/cyno cross reactivity, human and cyno recombinant FLT3L was used as the panning antigen in alternating fashion in some selection processes. To select for antibodies inhibiting FLT3L/FLT3 interactions, competition panning was used for some experiments. For competition panning, human FLT3L was used as the panning antigen, while FLT3-Fc in excess (>100×) was used as the phage elution agent instead of the conventional trypsin (Xiao X et al. mAbs 542 9, 996-1006 (2017)).

The BMV library was enriched 100-fold, the CS library 350-fold and the DP47 library 250-fold; the Dyax library was not enriched. Only the BMV and Dyax phage libraries were panned a third time resulting in 100-fold enrichment of the BMV phage library and 50-fold enrichment of the Dyax library compared to the second round of panning (FIG. 1A).

Monoclonal phage ELISA was performed to estimate the percentage of antigen specific phages after each round of selection. Only selections that achieved at least a 20% positive rate were processed for high throughput screening. With this set of criteria, the third output BMV panning, along with second output CS and DP47 panning were cloned into pSplice V4 and pdLG or pmLG vectors and converted to either scFv-Fc (Xiao X, et al., PLoS One, 2015 Oct. 15;10 (10): e0140691. doi: 10.1371/journal.pone.0140691) or IgG format (Xiao X, et al. mAbs 542 9, 996-1006 (2017)) for functional screenings by competition HTRF.

For functional screening, 293 freestyle cells (Thermo Scientific) were first transfected with either scFv-Fc or IgG constructs converted from the panning outputs. The resulting supernatant was used directly in HTRF based FLT3L/FLT3 interaction inhibition assays. For HTRF assay, 10 nM biotin-labeled FLT3L, 20 nM streptavidin-europium cryptate (Cisbio), 10 nM FLT3-mFc, and 20 nM anti-mFc-A647 (Cisbio) were mixed with 10 µL of transfection supernatant in a total volume of 20 µL/well in a 384-well Greiner plate. The 665 nm and 620 nm readings were taken five minutes after mixing and then at one hour intervals until readings became stable. The 665 nm/620 nm ratios were then calculated. A reduction in the ratio indicated inhibition of FLT3L/FLT3 interaction.

Figure 1B:
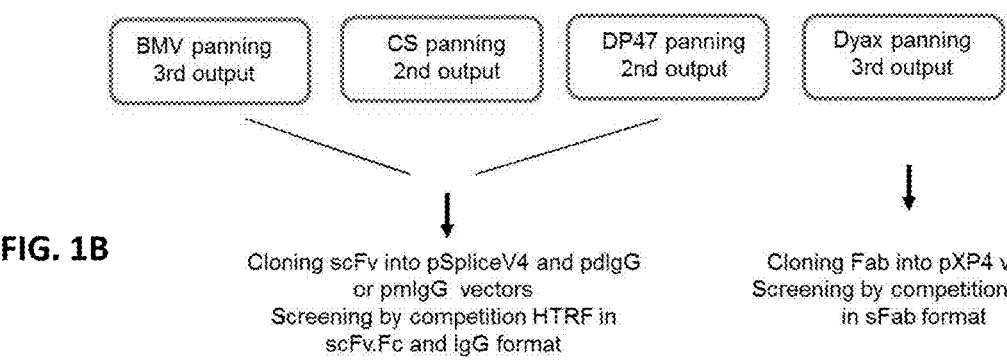
Figure 1C:
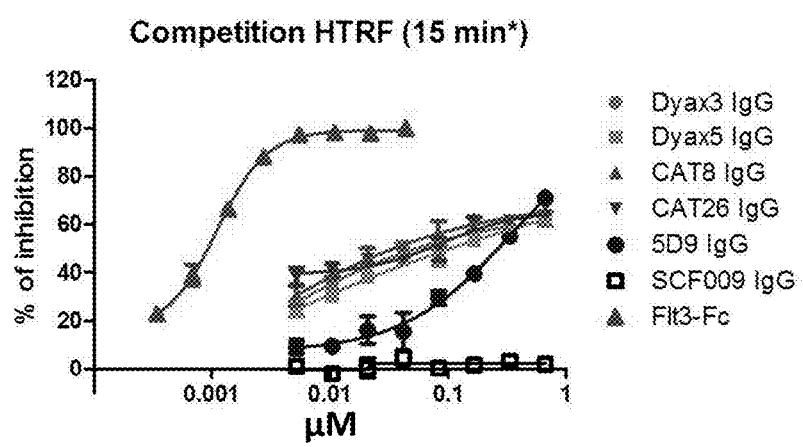

Panning output from direct or alternating antigen panning was converted to scFv-Fc and more than >4,000 colonies were selected for high throughput screening (HTS) in a HTRF FLT3L/FLT3-Fc interaction inhibition assay. Ten lead antibodies were identified, IgG TM converted, and expressed. The antibodies were retested in a second HTRF interaction inhibition assay and ten leads identified. In parallel, over seven hundred hits from competition panning were PmIgG converted and expressed in mammalian cells. The converted clones underwent the same HTRF FLT3L/FLT3-Fc interaction inhibition assay and two leads were identified (FIG. 1B).

The ten leads from alternate antigen panning and two leads from competition panning were expressed and purified in milligram amounts for further testing. The additional testing included HTRF FLT3L/FLT3-Fc interaction inhibition, receptor down-modulation, and signal transduction inhibition assays. The leads also underwent epitope binning and affinity determination. The screening campaign identified five lead antibodies that were further studied: Dyax3, Dyax5, CAT8, CAT26 and CAT5D9. Results from competition HTRF analysis are shown for the lead antibodies in FIG. 1C.

Example No. 2. FLT3 Down-Regulation Screening Assay

Upon FLT3L ligation, the FLT3 receptor dimerizes, auto-phosphorylates, and activates downstream signaling pathways. In the process, surface FLT3 is internalized and degraded. This internalization characteristic was exploited to develop an assay for screening lead anti-FLT3L candidate clones. Cell surface FLT3 expression can be measured by flow cytometry and inhibition of receptor-ligand binding can be determined by quantifying changes to cell surface FLT3 expression levels.

The cell lines RS4;11, EOL-1, MOLM13, and MV4-11 constitutively express FLT3. The cells were cultured under normal conditions and screened for relative expression of FLT3 after 2-24 hours of culture. Flow cytometry was used to measure FLT3 expression. Briefly, commercially available anti-CD135 (anti-FLT3) clone BV10A4H2 (Biolegend) was used in flow cytometry experiments, and mean fluorescence intensity (MFI) was reported as a measure of FLT3 expression. In all assays, a commercially available mouse anti-human FLT3L monoclonal antibody (R&D) or an in-house huFLT3-Fc construct was used as a positive control for effective neutralization of FLT3L activity.

Figure 2A:
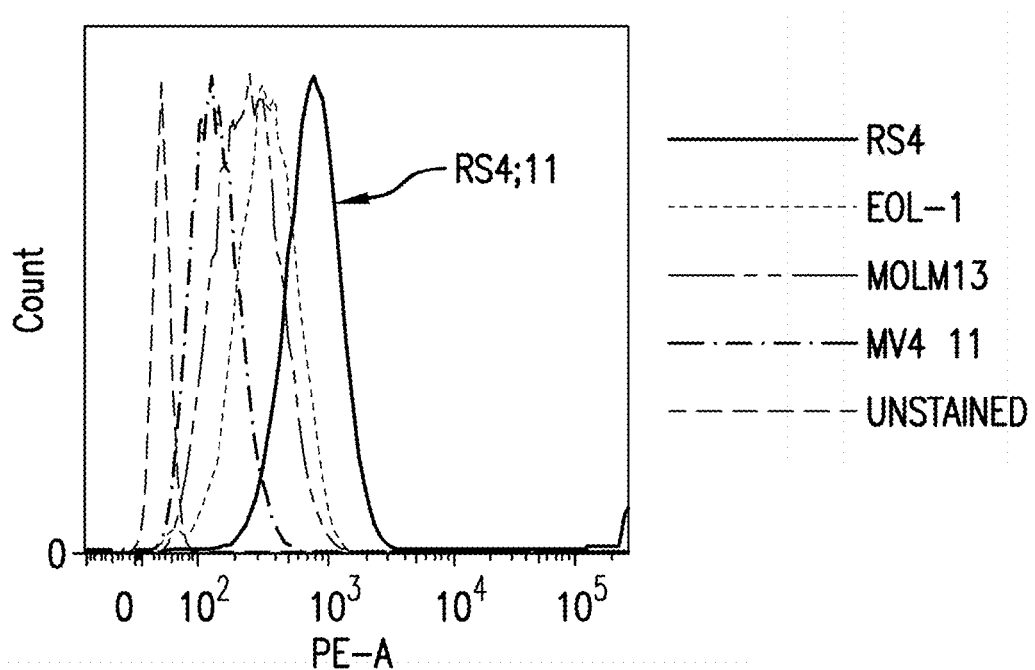
FIGS. 2A-2C. FLT3L expression in cell lines.
Figure 2B:
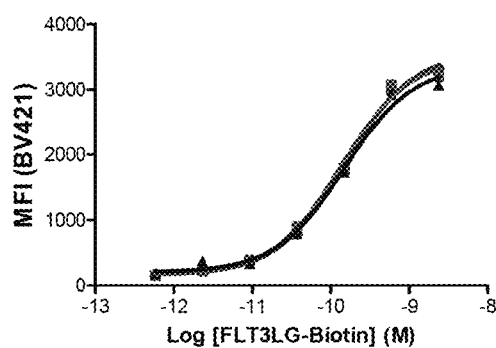

RS4;11, an acute leukemia (pro-B) line, exhibited consistent and high expression of FLT3 in culture compared to other commercially available lines reported to express FLT3 (FIG. 2A). Direct binding of FLT3L to cell surface FLT3 was confirmed using a serial dilution of biotinylated recombinant huFLT3L (rhuFLT3L) which, after 30 min incubation with RS4;11 cells at 4° C., could be detected physically bound to the cell surface using BV421-streptavidin, followed by flow cytometric analysis to determine mean fluorescence intensity (FIG. 2B).

Figure 2C:
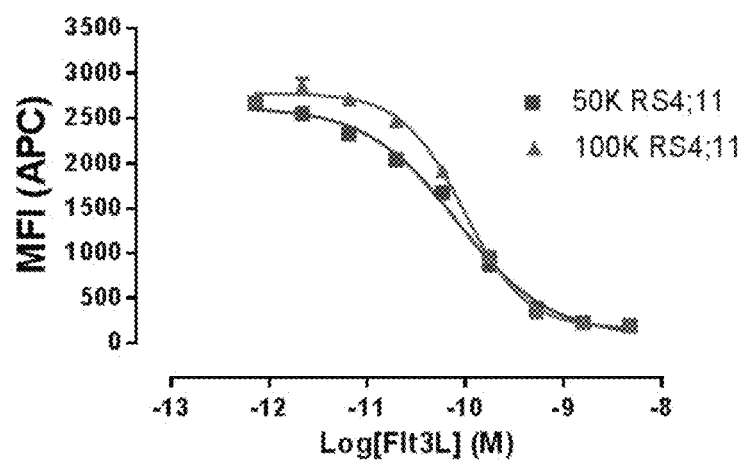

Finally, the ability of rhuFLT3L to induce detectable downregulation of cell-surface FLT3 on RS4;11 cells was confirmed by incubation of RS4;11 cells with serial dilutions of FLT3L at 37° C. for 2 hours. Stability of the conditions was evaluated by using 2 different concentrations of RS4;11 cells (50,000 (50K) and 100,000 (100K) cells). Downregulation of cell-surface FLT3 was determined using a fluorescently-labeled anti-CD135 antibody (clone BV10A4H2). Both cell densities exhibited a dose-dependent downregulation of cell-surface FLT3 2 hours after incubation with huFLT3L. Allophycocyanin (APC) MFI, an indicator of FLT3 expression, was reduced 25-fold over the range of huFLT3L used in the assay (FIG. 2C). These results showed the screening assay was effective in measuring a dose-depended response of bio-available FLT3L and would be suitable for testing the ability of candidate clones to functionally neutralize FLT3L. The response was not significantly different whether 50 or 100 thousand cells were used per well.

Optimization of Screening Assay

Figure 3A:
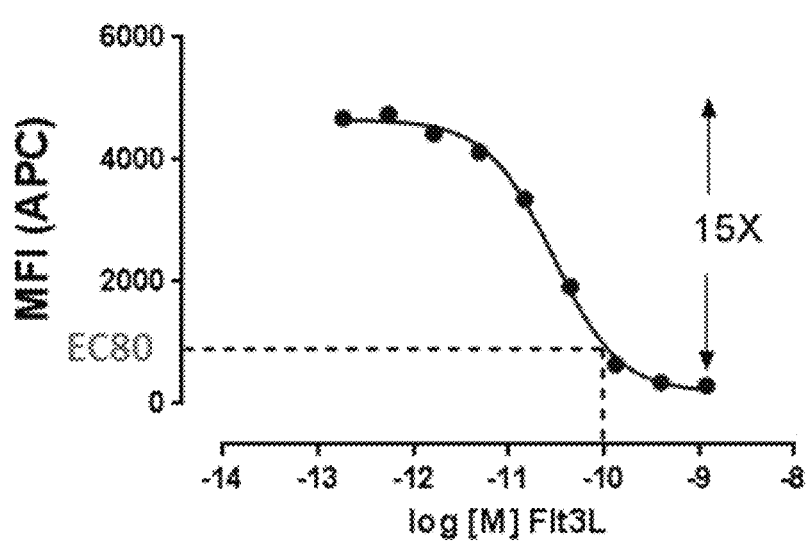
FIGS. 3A and 3B. Derivation of the EC80 and subsequent testing.
Figure 3B:
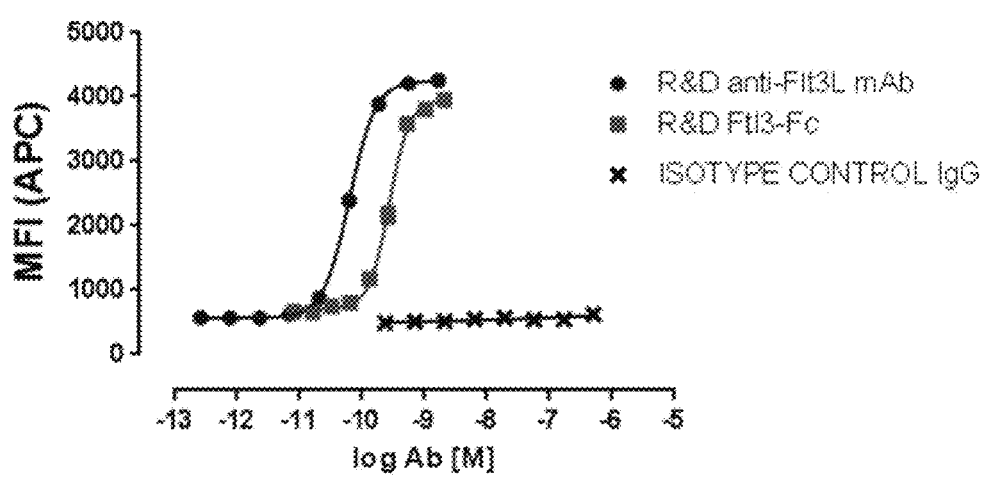

Screening assay conditions were further refined to determine ideal cell culture conditions for evaluating anti-FLT3L candidate clones. Final conditions were: 50,000 RS4;11 cells per well incubated with 96 pM rhuFLT3L with or without anti-FLT3L mAb candidate clones in complete Roswell Park Memorial Institute (RPMI) media with one percent bovine serum albumin (BSA) for 2 hours in an humidified incubator set at 37° C., 5% CO2. Subsequent downregulation of FLT3 expression was determined by flow cytometry as measured either as raw MFI or % downregulation. 96 pM rhuFLT3L (EC80) was chosen as it is the point at which the exponential phase of the dose response curve commenced and as such ensured any functional inhibition of rhuFLT3L would be immediately reflected by changes to the level of FLT3 downregulation on the cell RS4;11 cell surface. (FIG. 3A). Assay efficacy was confirmed using a commercially available mouse anti-huFLT3L antibody control (MAB608, R&D Systems) (FIG. 3B). Due to the cross-species reactivity of FLT3 with its ligand, this assay was effective for testing clones against human, cyno, and rodent FLT3L, despite being a human cell line. For mouse FLT3L, the EC80 was 36 pM.

Example No. 3. Neutralizing Activity of Lead Antibody Candidates Against Soluble FLT3L Upon ligation of FLT3L to FLT3, the receptor dimerizes, autophosphorylates, and propagates a signaling cascade once internalized. This process, measured by FLT3 downregulation, can be inhibited by antibodies that bind FLT3L. Thus, lead candidates were tested for their ability to inhibit FLT3 downregulation on RS4;11 cells by binding human, mouse, or cynomolgus monkey (cyno) soluble FLT3L (sFLT3L). The optimized screening assay was used to test the neutralizing ability of lead candidates. As described, RS4;11 cells (50,000 cells per well) were incubated for two hours in complete RPMI with one percent BSA in the presence of either human or cyno FLT3L (96 pM), or mouse sFLT3L (36 pM). Serial dilutions of each clone were added and either soluble FLT3-Fc construct or commercially available human anti-FLT3L antibody were used as positive controls. FLT3 expression on RS4;11 cells was determined using flow cytometry and reported as MFI.

Figure 4A:
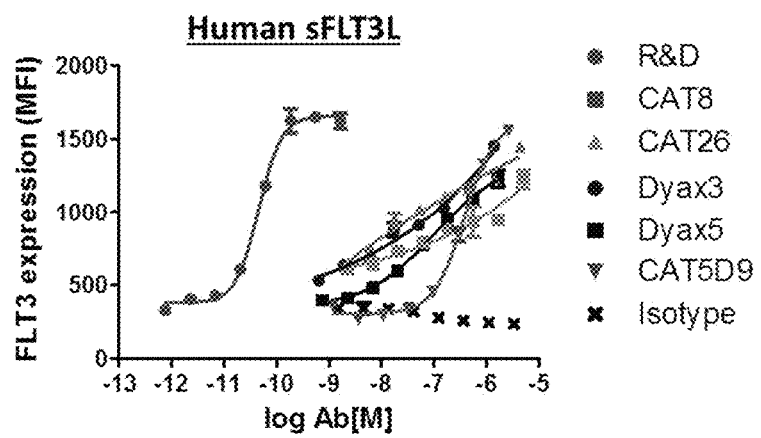
FIGS. 4A-4C. Lead antibody candidate inhibition of human and cyno sFLT3.
Figure 4B:
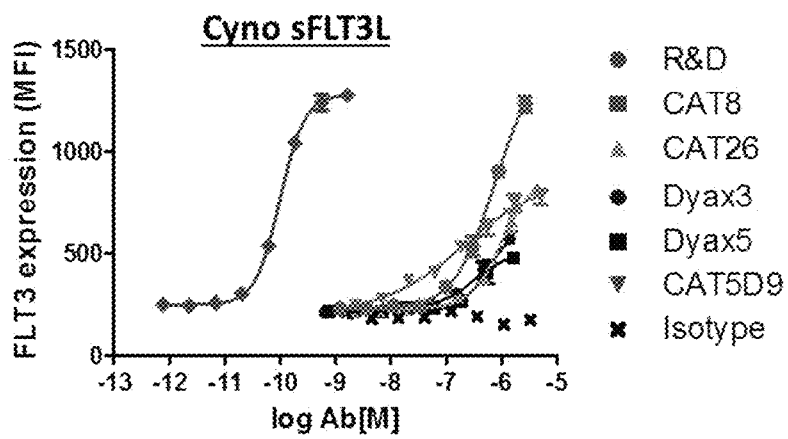

As shown in FIGS. 4A and 4B, all lead clone antibodies demonstrated the ability to inhibit both human and cyno sFLT3L to some extent. CAT8, CAT26, Dyax3, and Dyax5 all displayed similar inhibition of human sFLT3L and cyno sFLT3L. Although shown in Table 3 below, the IC50 values for CAT8, CAT26, Dyax3, and Dyax5 lack validity as $IC_{MAX}$ was never reached.

Figure 4C:
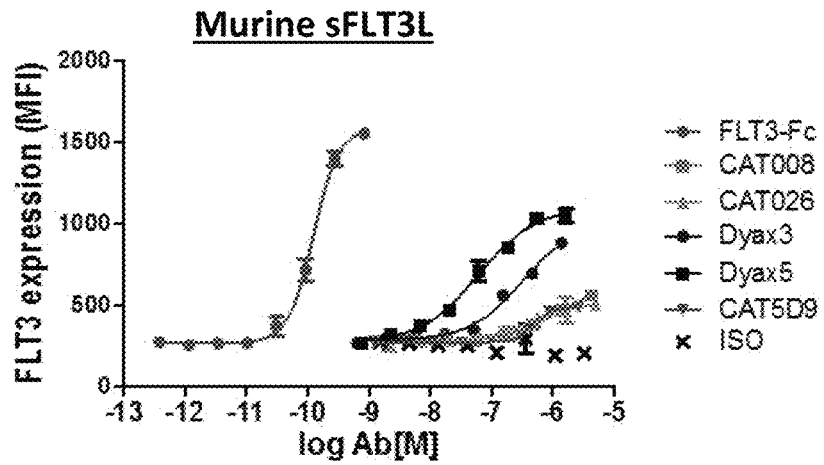

In contrast, CAT5D9 achieved $IC_{MAX}$ and produced the S-shaped curve expected from FLT3L inhibition (FIGS. 4A and 4B). IC50 values for CAT5D9 presented in Table 3 indicate cross reactivity with human and cyno, but not murine FLT3L (FIG. 4C).

TABLE 3

IC50 (nM) of Lead antibody candidates against 96 pM human, cyno or mouse sFLT3L.

|  | Human | Cyno | Mouse |
| --- | --- | --- | --- |
| R&D | 0.04 | 0.10 | 0.12 |
| CAT8 | 43.5 | 3001 | N/A |
| CAT26 | 618 | 2584 | N/A |
| DYAX3 | 54.8 | 3066 | 1489 |
| DYAX5 | 245 | 6015 | 354 |
| CAT5D9 | 385 | 564 | N/A |

Example No. 4. Binding Activity of Lead Antibody Candidates Against Cell Surface FLT3L FLT3L is expressed as a cell-membrane protein and circulates as a soluble protein when cleaved. Both membrane-bound and soluble forms are biologically active. In order to effectively block FLT3-mediated signaling pathways, lead antibody candidates should bind both the soluble and membrane bound forms of FLT3L.

Consistent with this, cell surface binding to human, cyno, and mouse FLT3L was evaluated by transfecting Chinese hamster ovary (CHO) cells with the respective full-length protein for each species. Candidate clones were incubated with FLT3L-expressing cell lines for 1 hour at 4° C. before being washed twice to remove unbound antibody. Cells were then incubated with PE-labeled goat anti-hu IgG secondary detection pAb to quantitate bound antibody which was measured by flow cytometric analysis of PE signal. The huFLT3-Fc construct, on a hu IgG backbone, was used as a positive control reagent for FLT3L expression as it cross reacts with cyno and mouse, in addition to human ligand.

Figure 5A:
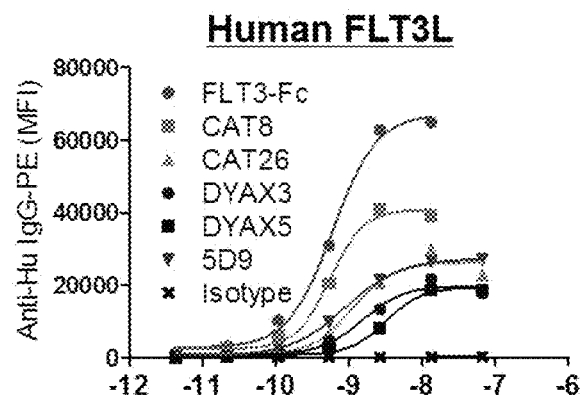
FIGS. 5A-C. Lead candidate inhibition of cell surface FLT3.
Figure 5B:
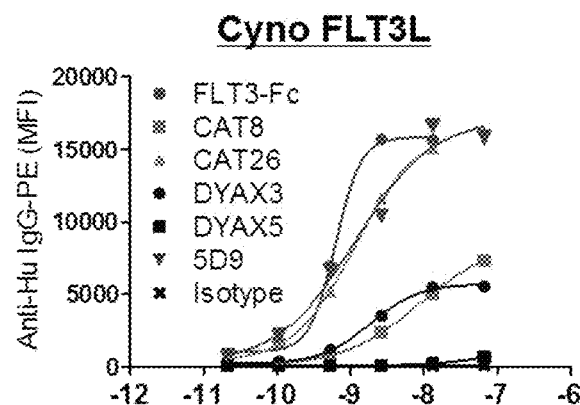
Figure 5C:
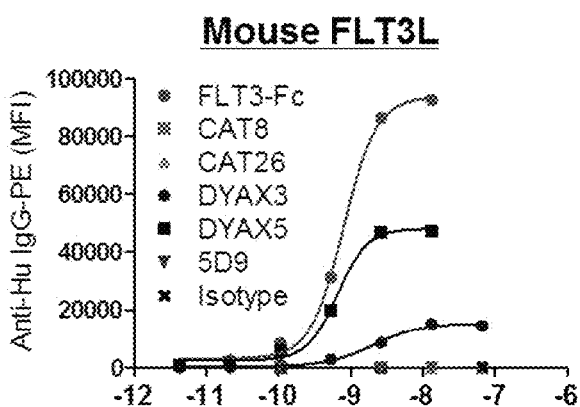

All lead candidates bound human FLT3L (FIG. 5A), and all except DYAX5 bound to cyno FLT3L (FIG. 5B). In contrast, only Dyax5, and to a lesser extent Dyax3, displayed cross reactivity with mouse FLT3L (FIG. 5C).

Thus, all lead candidates displayed an ability to bind cross species FLT3L, albeit with differing efficacy. As differences were apparent in the degree of receptor occupancy for each clone, both EC50 and max occupancy were noted (expressed as percent relative to FLT3-Fc) and taken into account in the final evaluation. Results are shown in Table 4 for human, cyno, and mouse FLT3L expressed in CHO cells.

TABLE 4

EC50 (nM) and maximum occupancy (% relative to FLT3-Fc)

|  | Human | | Cyno | | Mouse | |
| --- | --- | --- | --- | --- | --- | --- |
|  | EC50 | % Ocp | EC50 | % Ocp | EC50 | % Ocp |
| FLT3-Fc | 0.09 | 100 | 0.6 | 100 | 0.14 | 100 |
| CAT8 | 0.08 | 60 | 9.0 | 32 | N/A | N/A |
| CAT26 | 0.19 | 46 | 1.1 | 96 | N/A | N/A |
| DYAX 3 | 0.27 | 33 | 1.8 | 35 | 0.39 | 16 |
| DYAX 5 | 0.66 | 28 | N/A | N/A | 0.11 | 51 |
| CAT 5D9 | 0.157 | 40 | 1.1 | 100 | N/A | N/A |

Example No. 5. Binding of Lead Antibody Candidates to Endogenous Human FLT3L

FLT3L is expressed on the surface of primary T-cells upon stimulation by □-chain cytokines, namely IL-2, IL-7, or IL-15, independently of TCR engagement. In Example No. 4, lead antibody candidates demonstrated the ability to bind to CHO cells transfected with human FLT3L protein. The next step was to ensure that they could bind endogenous FLT3L from a primary human cell line. Thus, the lead antibody candidates were tested for their ability to bind huFLT3L on IL-2 stimulated primary T-cells acquired from human donors.

Figure 6A:
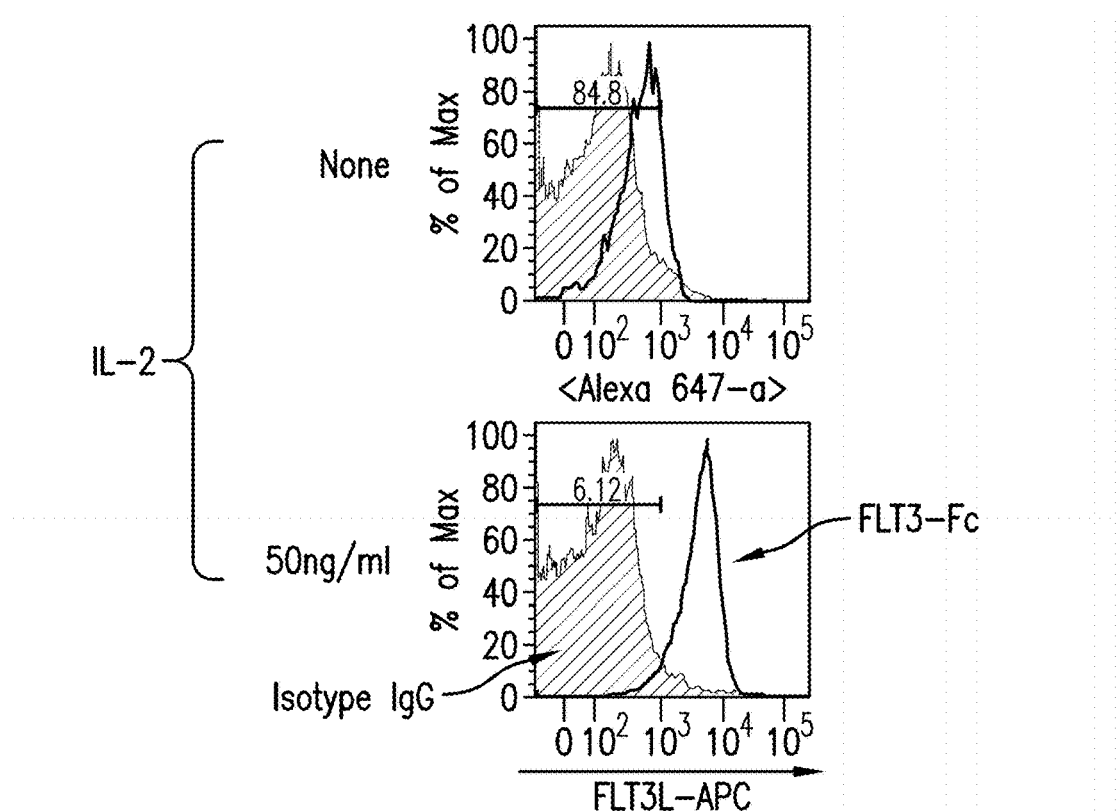
Figure 6B:
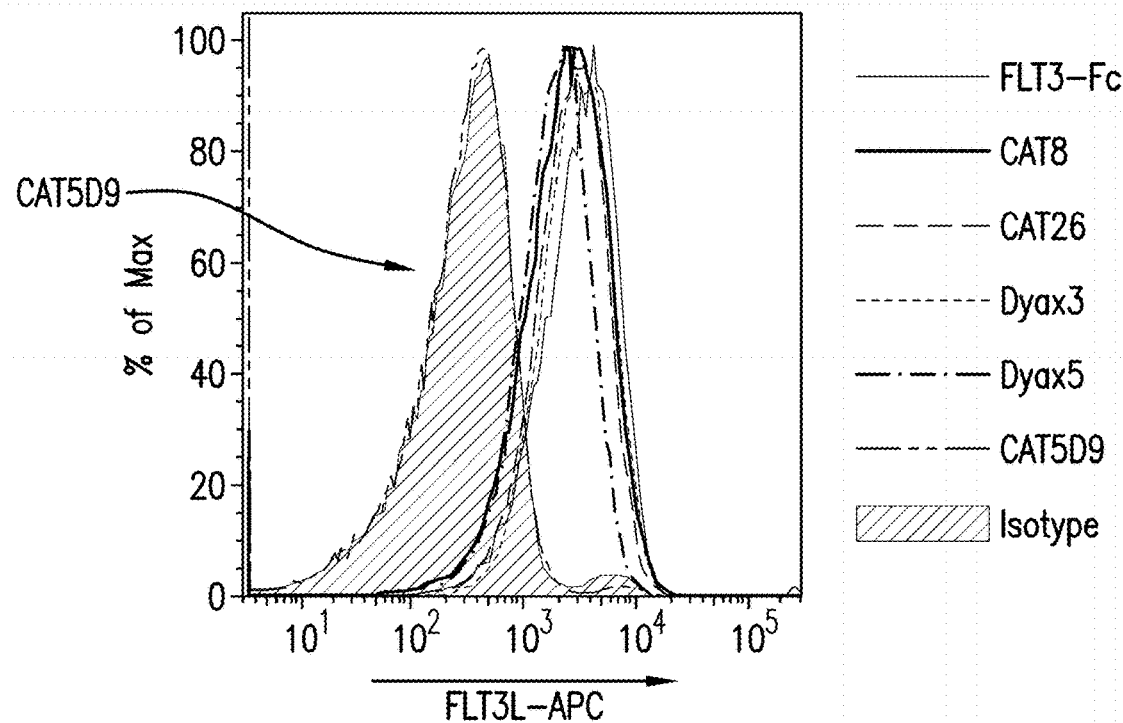

To induce FLT3L expression on the cell surface, freshly isolated human T cells were stimulated with 50 ng/mL IL-2 in the absence of anti-CD3 (activation of T cells with anti-CD3 would lead to shedding of FLT3L from the cell surface) for 5 days. After this time, expression on T-cells was confirmed using the human FLT3-Fc construct (FIG. 6A). Serial dilutions of each clone were then incubated with IL-2 stimulated T cells (100K/well) for 30 min at 4° C. Excess antibody was removed by washing with buffer and surface-bound antibody was detected with APC-labeled anti-human IgG. All lead clones, except CAT5D9, bound endogenous FLT3L on human primary T-cells (FIG. 6B). CAT5D9 binding to endogenous FLT3L was initially not detectable due to its low binding affinity. However, when CAT5D9 was dimerized with anti-IgG (APC-labeled) prior to incubation with T cells, its avidity was sufficiently enhanced to confirm dose-dependent binding to endogenous FLT3L (FIG. 6C).

Example No. 6. Lead Antibody Candidate Inhibition of Cell-Surface FLT3L

The ability of lead candidates to bind cell-surface FLT3L provided limited insights regarding functional inhibition of the ligand. Ideally, binding of the lead candidates to cell-surface FLT3L should decrease signaling activity of the ligand-receptor complex.

To test this, 1,000 huFLT3L-expressing CHO cells/well were plated overnight to adhere. The next day, CHO culture media was removed, the cells were washed gently with RPMI and serial dilutions of antibodies were added for 30 min, prior to the addition of FLT3+RS4;11 (100K/well). After 2 hr incubation at 36° C., RS4;11 cells were transferred into a fresh 96-well plate on ice for staining to detect FLT3 downregulation. In addition to the stain used for our standard RS4;11 FLT3 downregulation assays, anti-CD19 was included to exclude any contaminating CHO cells. FLT3 downregulation was measure by flow cytometry.

Figure 7A:
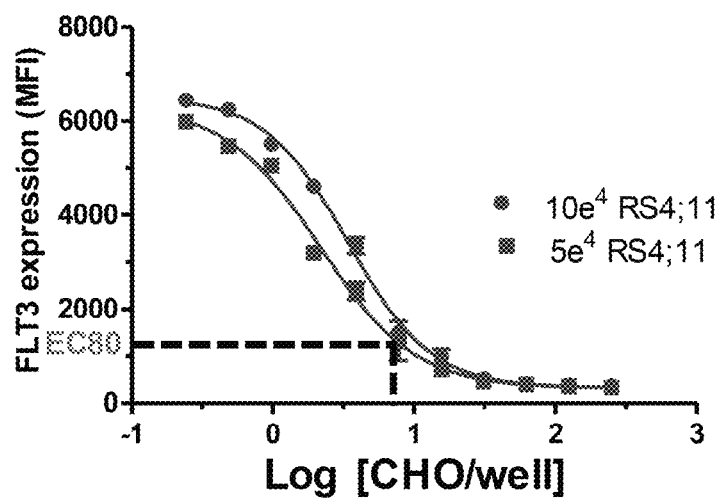
FIGS. 7A and 7B. Inhibition of cell surface signaling by lead candidates.
Figure 7B:
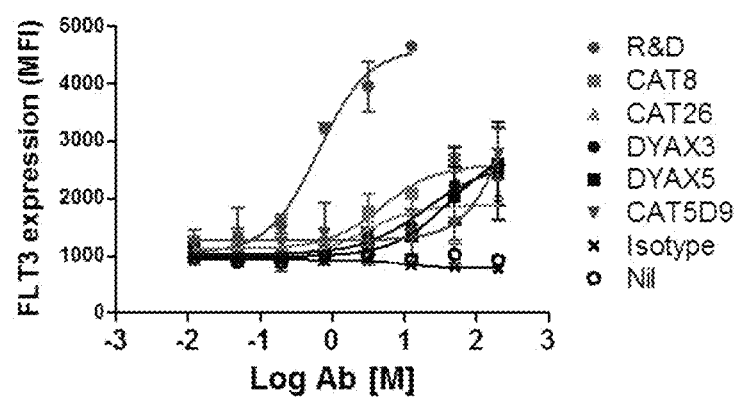

The lead antibody candidate block assay demonstrated that all lead candidates had the ability to inhibit cell-surface FLT3L to some extent, though all candidates exhibited relatively low activity compared to the commercial control antibody, a reflection of low affinity (FIG. 7).

Example No. 7. Lead Clone Inhibition of FLT3L-Induced FLT3 Signaling

Autophosphorylation of FLT3 leads to the activation of signal transduction networks mainly through PI3K and the RAS cascade which in turn activates AKT (protein kinase B, PKB), MEK, and ERK. The signaling cascade ultimately leading to the transcription of genes that promote cell survival and proliferation. To confirm lead antibody candidates were blocking downstream signaling of FLT3 by FLT3L in primary human cells, phosphorylation of ERK and MEK in CD133+ stem cells was measured with Mesoscale MSD Phospho-ERK1/2 and phosphor MEK1/2 whole cell lysate.

Figure 8A:
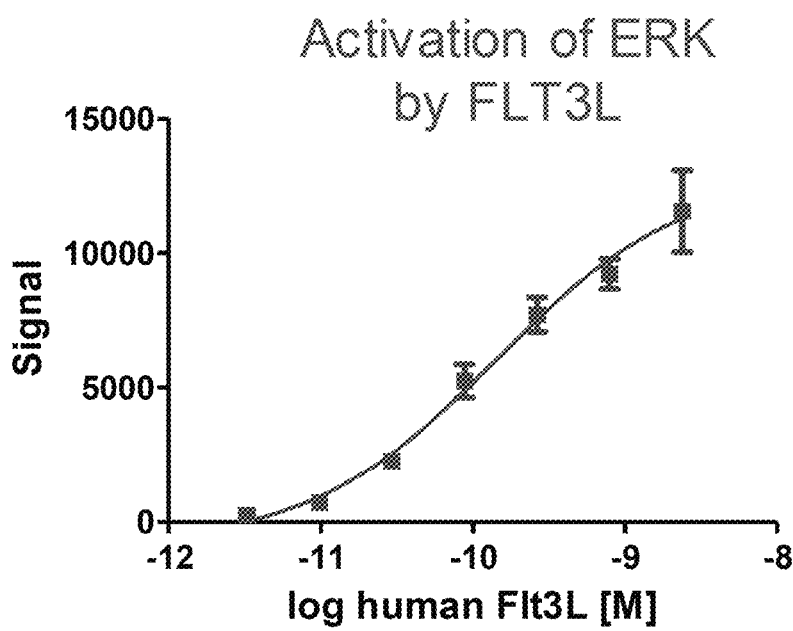
FIGS. 8A and 8B. Activation and neutralization of ERK signaling pathways.
Figure 8B:
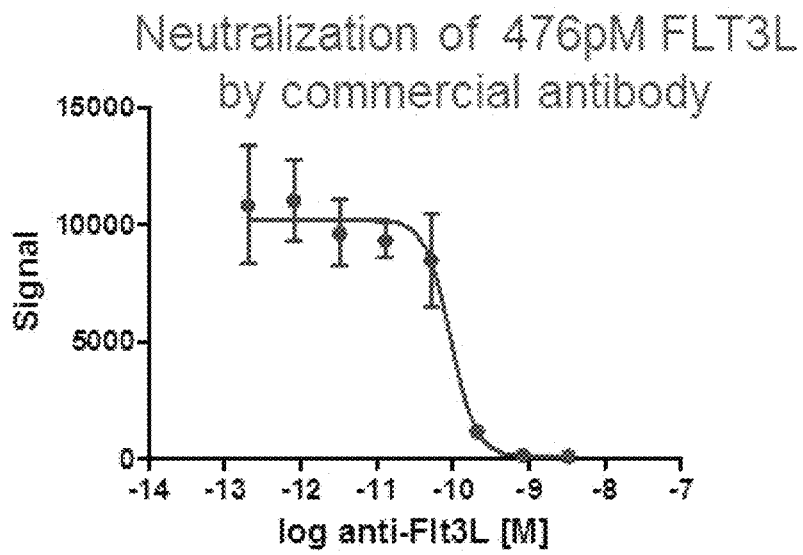

Assay validation was established using the RS4;11 cell line, with activation of ERK induced by FLT3L in a dose-dependent manner. (FIG. 8A). Serial dilutions of FLT3L were incubated with 300,000 RS4;11 cells per well for 8 mins at 36° C. Cells were then harvested, lysed, and assayed for phosphorylated ERK as per manufacturer's instructions. As with earlier assays, the EC80 for FLT3L activation of ERK was determined (476 pM) and used to test the inhibitory activity of candidate anti-FLT3L antibody clones. Assay utility was confirmed using a commercially available mouse anti-human FLT3L antibody as a positive control for effective neutralization (FIG. 8B).

Using these established parameters, lead clones were tested using in vitro expanded primary CD133+ stem cells that were validated for FLT3 expression prior to use. Lead clones were pre-incubated with 476 pM FLT3L for 30 mins, then added to CD133+ stem cells. After 8 mins incubation at 36° C., cells were harvested, lysed and assayed for phosphorylated ERK and MEK using MSD assays as per the manufacturer's instructions. Commercially available mouse anti human FLT3L was used as a positive control.

Figure 9A:
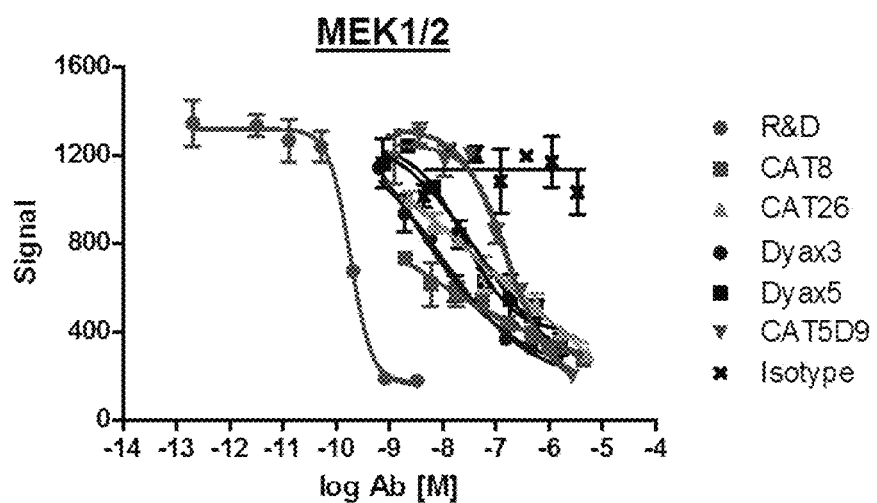
FIGS. 9A and 9B. Lead candidate blocking of MEK 1/2 and ERK downstream signaling.
Figure 9B:
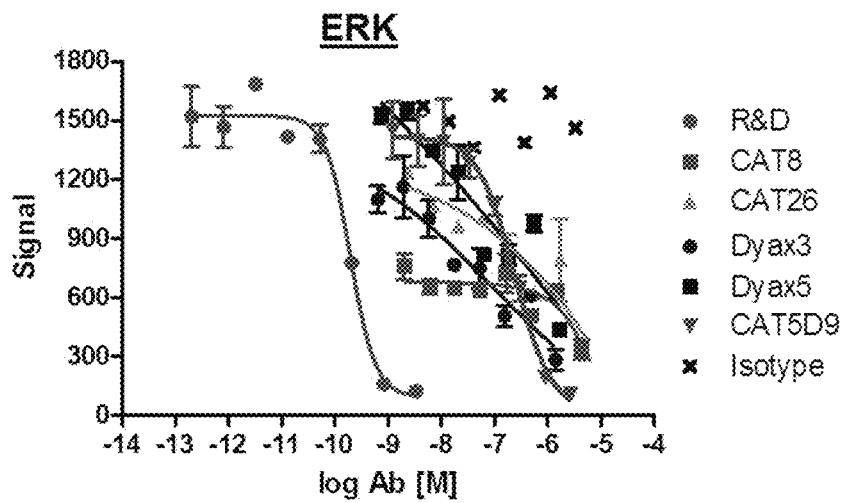

All candidate clones appeared to inhibit the induction of MEK (FIG. 9A) and ERK (FIG. 9B) by FLT3L. However, only CAT5D9 reached $IC_{MAX}$ and displayed the expected S-shaped dose-response curve (Table 5). Combined, the results presented in the examples suggested CAT5D9 was the best clone of the lead candidates, and should proceed for optimization conditional to biophysical evaluation of affinity and epitope binding site.

TABLE 5

| IC50 (nM) against 0.476 nM FLT3L | | |
|---|---|---|
| | MEK | ERK |
| R&D | 0.19 | 0.19 |
| CAT8 | $7.4e^6$ | 0 |
| CAT26 | $2.1e^{17}$ | $2.4e^{38}$ |
| DYAX3 | 93 | 2.4 |
| DYAX5 | $2.4e^7$ | 25 |
| CAT5D9 | 181 | 187 |

Example No. 8. Confirmation of Target Specificity

CAT5D9 appeared to be the best lead candidate by functional evaluation in biological assays. Octet epitope binning was used to determine the CAT5D9 binding region relative to the receptor FLT3.

Epitope binning was used to determine lead antibodies that share the same binding region with FLT3 receptor on FLT3L. Binning was carried out in three phases. In phase I, Biotin-FLT3L binding to avidin probe was performed. In phase II, individual antibodies were bound to Biotin-FLT3L. In phase III, each of the test antibodies was added to the phase II antibody. Any additional binding detected was indicative of the two antibodies having non-competing binding sites to the target FLT3L. Buffer only, with no antibody added at phase III and FLT3-Fc were used as negative and positive controls, respectively. If buffer only was added at phase III, the resulting dissociation kinetics of the antibody to FLT3L reflects the clone's inherent affinity for the target.

Figure 10A:
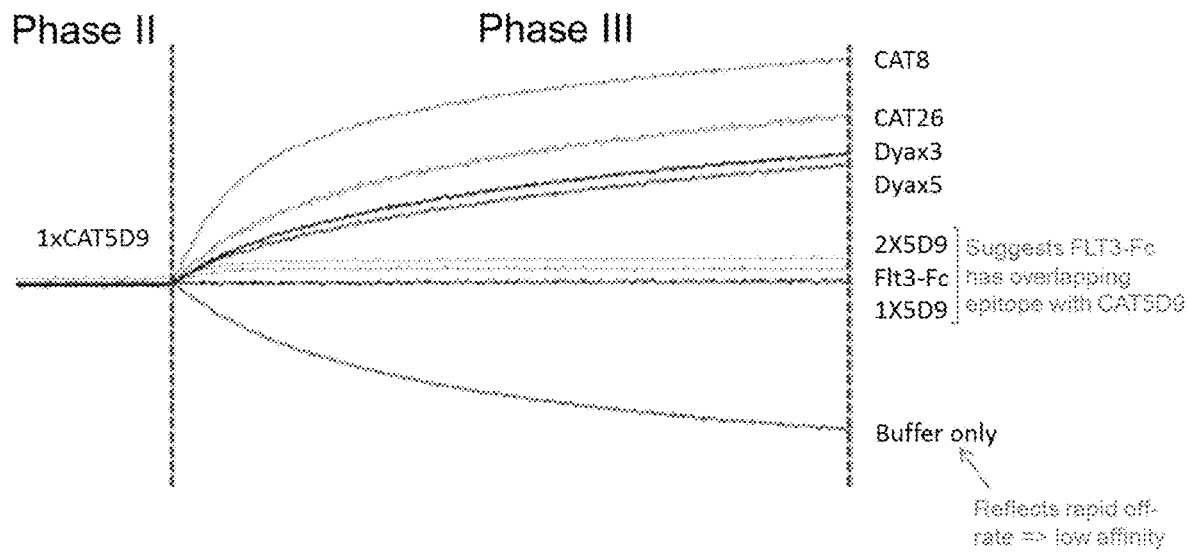
FIGS. 10A and 10B. Target specificity and binding kinetics of lead candidates.
Figure 10B:
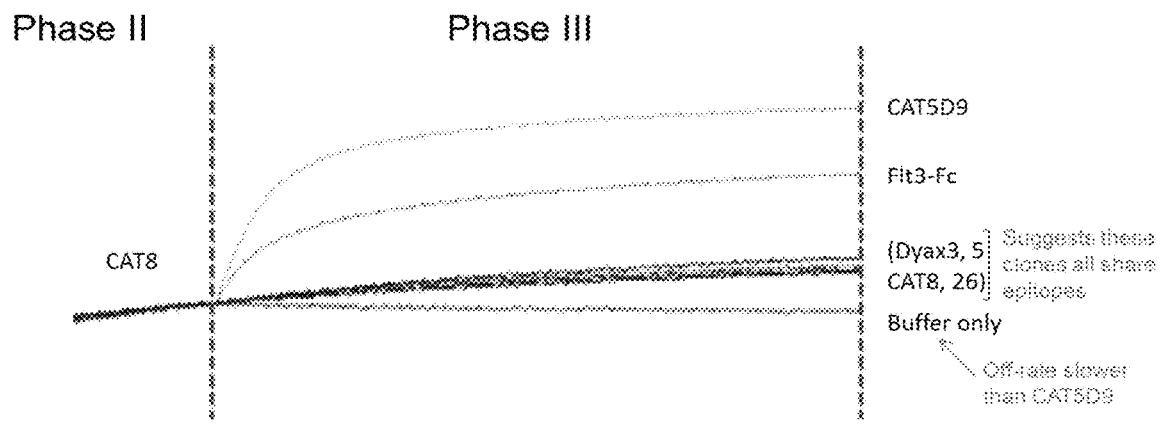

Only CAT5D9, added at 1× and 2× concentrations, inhibited binding by FLT3-Fc, suggesting that CAT5D9 was hitting the desired target site on FLT3L (i.e., it shares the same or overlapping epitope as FLT3-Fc) (FIG. 10A). Importantly, in contrast, the remaining four candidate clones were not inhibited by CAT5D9, suggesting that they bound to a different FLT3 epitope (FIG. 10A). In addition, the rapid off rate when buffer alone was added supports the previous experiment suggesting the affinity of CAT5D9 is low (meaning its potential for improved performance with optimization was high). Consistent with this, when each of the 4 remaining clones was bound in Phase II (CAT8 shown as representative chart presented in FIG. 10B), additional binding of CAT5D9 and FLT3-Fc can be detected in Phase III, reflecting their different binding sites. It was also observed that each of the other 4 clones binned together and that when buffer alone was added, their dissociation rate was relatively slow.

Together, these data confirm that only CAT5D9 directly competed with FLT3 at the FLT3L binding region and appeared to be doing so with low affinity binding, suggesting its potential for optimization. On the other hand, the remaining clones were all hitting a site that, based on functional data, was not directly competing with FLT3. Their slow dissociation rate suggested they were already binding with reasonable affinity to FLT3L and would have little potential for optimization. Inhibition originally present in initial screening assays was likely due to steric hindrance or partial blocking of the receptor binding site.

Example No. 9. Biacore Binding Kinetics (C9)

Biacore analysis was used to determine binding kinetics of the antibody leads and confirm the Octet data that suggested CAT5D9 had poor affinity for FLT3L. Kinetics of anti-FLT3L fragment antigen binding and human and cynomolgus monkey FLTL3 were determined in human CAT8, CAT26, Dyax3, and Dyax5. In addition, binding kinetics of CAT5D9 fragment antigen was determined for both human and cynomolgus monkey FLT3L.

Results are presented in Table 6. The equilibrium dissociation constant ($K_D$) was more than 50× greater in the CAT5D9 human and cynomolgus monkey compared to the remaining lead antibodies. CAT5D9 exhibited low quality, fast off kinetics (hu=70.72, cyno=70.66). As a result steady-state binding data was obtained as a check on the kinetic data $K_D$. Steady-state binding supported the results of kinetic binding, showing similar values (Table 3). These data confirm the low affinity of CAT5D9 and its potential for improved performance with optimization.

TABLE 6

Binding kinetics of Anti-FLT3L antibody leads.

| Anti-FLT3L Fabs | FLT3L species | kon (xE + 5/Ms) | koff (xE − 3/s) | $K_D$ (kin: koff/kon) (nM) | $K_D$ (steady-state) (nM) |
|---|---|---|---|---|---|
| CAT8 | hu | 6.28 | 5.56 | 8.85 | NA |
| CAT26 | hu | 1.91 | 0.84 | 4.37 | NA |
| Dyax3 | hu | 0.66 | 1.23 | 18.69 | NA |
| Dyax5 | hu | 2.28 | 5.01 | 21.96 | NA |
| CAT5D9 | hu | 0.61 | 70.72 | 1157 | 1595 |
| CAT5D9 | cyno | 0.61 | 70.66 | 1157 | 1607 |

Fabs = Fragment antigen Binding;
Hu = Human;
cyno = cynomolgus monkey;
kon = Binding association constant;
Koff = Binding dissociation constant;
$K_D$ = Equilibrium dissociation constant Example No. 10. Absence of CAT5D9 Cross-Reactivity In addition to confirming CAT5D9 bound to the correct FLT3L epitope, it was also important to confirm that it would not bind to the close structural homologues of FLT3L, stem-cell factor (SCF) and colony stimulating factor (CSF1). Both factors are ligands for protein tyrosine kinase receptors (c-Kit and CSFR1, respectively) that are the primary off-target hits for small-molecule FLT3 inhibitors currently used in the oncology setting to manage malignancy arising from the constitutively activated FLT3-IT9D mutation.

To test this, an ELISA plate was coated with 2 □g of recombinant human SCF or CSF1. After washing, the plate was blocked with 3% milk in Tris-Phosphate Buffered Saline (TPBS) and lead antibodies were added in serial (×2) dilution, starting at 50 □□g/ml. After incubation, unbound antibody was removed by washing and bound antibody was detected using anti-human IgG-HRP in combination with TMB substrate for color development. Commercially available goat anti-SCF pAb and mouse anti-CSF1 mAb were used as positive binding controls.

Figure 11A:
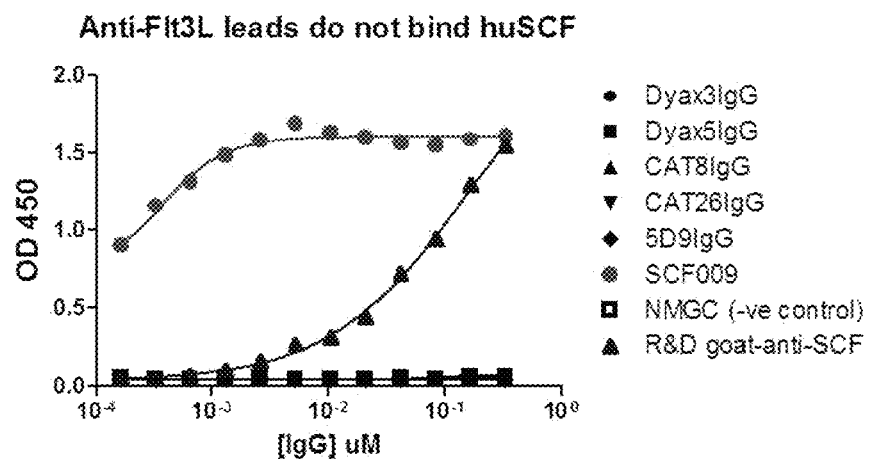
FIGS. 11A and 11B. Cross reactivity of lead candidates to huSCF and huCSF.
Figure 11B:
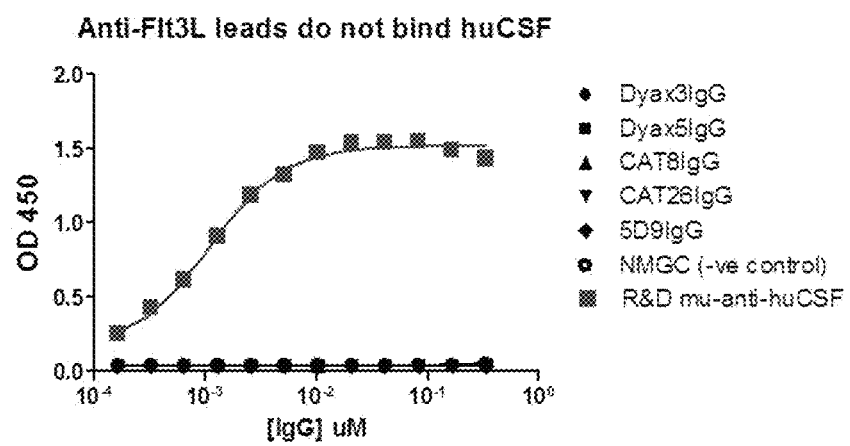

None of the lead candidates cross-reacted with huSCF (FIG. 11A) or huCSF1 (FIG. 11B). Importantly, these results demonstrate selectivity of CAT5D9 in binding only FLT3L but not structurally similar TKR ligand molecules.

Example No. 11. Affinity Optimization of CAT5D9

As discussed above, CAT5D9 bound FLT3L with low affinity and therefore demonstrated potential for improved performance with affinity optimization. The desired KD of 300 pM was set based on PK modelling. An optimization campaign was designed to achieve up to a 10,000-fold improvement of KD.

After germlining of frameworks, two parallel strategies were employed —parsimonious mutagenesis and block mutagenesis. Parsimonious mutagenesis mutates every position in all 6 CDRs to all 20 amino acids, one at a time. Clones were screened using high throughput methods and individual beneficial mutations are combined together. Block mutagenesis mutates continuous stretches of 5 to 6 positions in CDRs in an overlapping pattern, and resulting libraries of about 1E6 to 1E7 clones are first enriched using phage display panning techniques and later screened using high throughput methods.

After the first optimization round, 30 clones from parsimonious mutagenesis and 24 clones from block mutagenesis were tested in an IgG format. Using molecular modelling techniques, we identified and combined the best mutations resulting in clone 5D9-Clone 6, which achieved a KD of 1610 nM (measured by Biacore), a 700× improvement of affinity over the parental 5D9 (see Table 7). The affinity of lead clones SC4017 and AM40 exceeded CDTP criteria (<300 pM). Further both optimized clones bind to and neutralize endogenous cell-surface FLTL, bind endogenous soluble FLT3L in human serum, and bind to and neutralize cyno FLT3L.

TABLE 7

Binding Data Summary for Lead Clones from Optimization of CAT5D9.

| | | kon (1E+5/Ms) | koff (1E−4/s) | $K_D$ (pM) |
|---|---|---|---|---|
| hFLT3 receptor/hFLT3L | | 3.6 | 81.2 | 22,340 |
| 5D9 parent/hFLT3L | Parental | 0.6 | 707.2 | 1,157,000 |
| 5D9-C06/hFLT3L | Round 1 | 5.5 | 8.8 | 1,610 |
| AM40/hFLT3L | Round 2 | 10.9 | 1.8 | 170 |
| AM40/cFLT3L | Round 2 | 26.6 | 1.7 | 63 |

TABLE 7-continued

Binding Data Summary for Lead Clones
from Optimization of CAT5D9.

|  |  | kon (1E+5/Ms) | koff (1E−4/s) | $K_D$ (pM) |
|---|---|---|---|---|
| SC4017/hFLT3L | Round 2 | 14.5 | 0.5 | 37 |
| SC4017/cFLT3L | Round 2 | 58.4 | 0.5 | 8.8 |

Figure 12A:
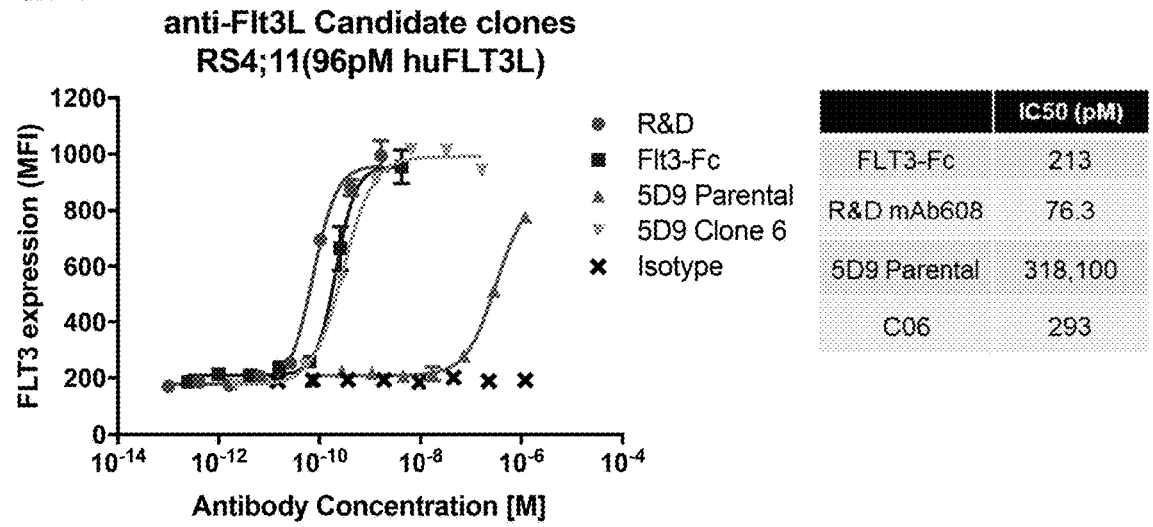
FIGS. 12A and 12B. Clone optimization.

This increase in affinity translated to a >1000-fold improvement in functional activity as measured by FLT3 downregulation on RS4;11 cells (FIG. 12A) using the method described for earlier clone selections.

Figure 12B:
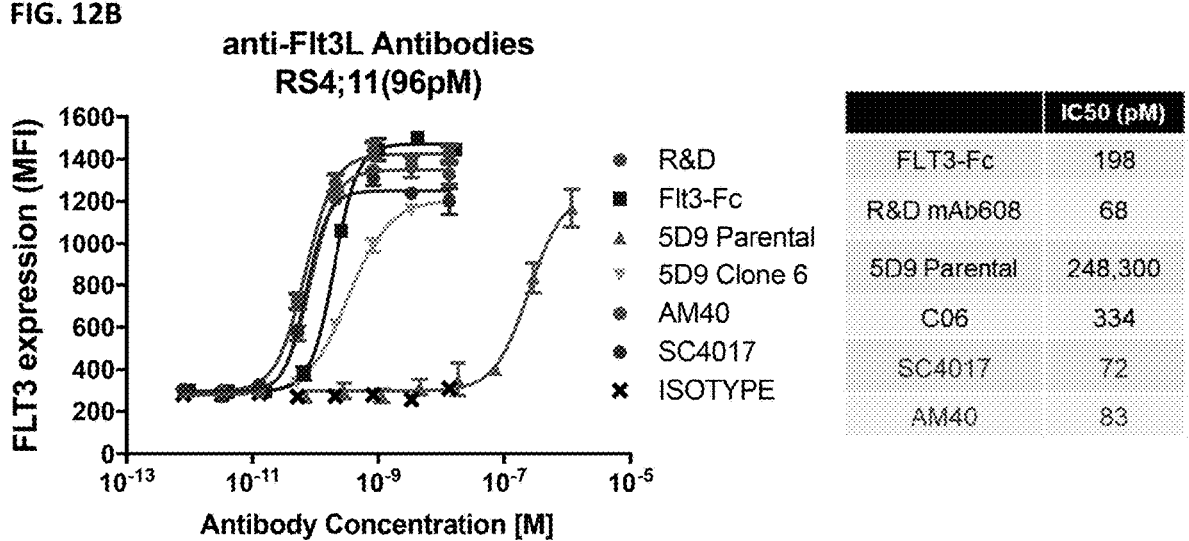

In order to achieve affinity of 300 pM, a second round of affinity optimization was performed. Clone 6 (C06) was mutated, and the resulting mutants were screened in a similar fashion as in the first optimization round. As a part of phage panning in block mutagenesis, Clone 6 was used in an IgG format as a competitor to enrich for clones with substantially higher affinity. The best clone from block mutagenesis was clone AM40 with KD=170 pM. Several combinatorial clones of AM40 and mutations from the second round of parsimonious mutagenesis were combined and produced one superior clone, SC4017 with a KD=37 pM. This higher affinity was again reflected in improved functional inhibition of FLT3L as demonstrated by FLT3 downregulation on RS4;11 cells (FIG. 12B). However, further analysis attributed the superior performance of SC4017 to a single additional tryptophan incorporated adjacent to the binding region. This represented a development risk given the vulnerability of exposed tryptophan residues to oxidation. For this reason AM40 was selected as the lead IgG clone. Despite its slightly lower affinity (170 pM) compared with SC4017 (37 pM), AM40 still exceeded the original target of 300 pM and was determined to have lower risks for development.

Figure 13A:
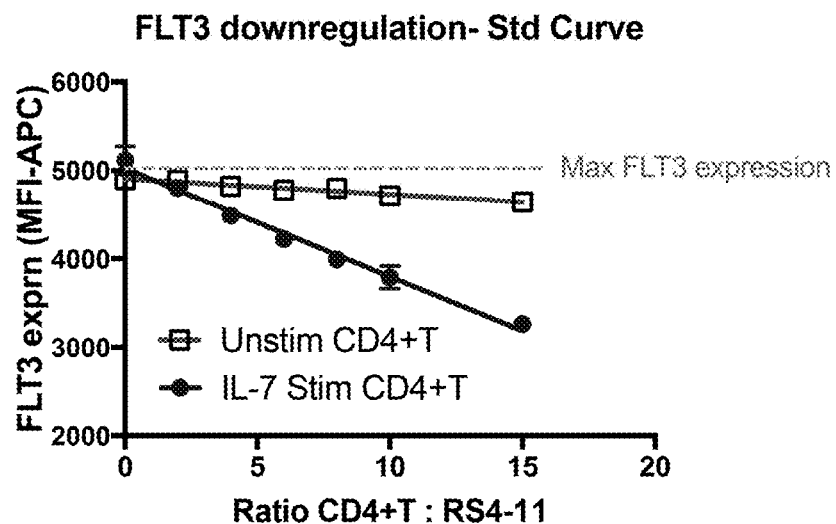
FIGS. 13A and 13B. Effective neutralization of endogenous cell-surface FLT3L.
Figure 13B:
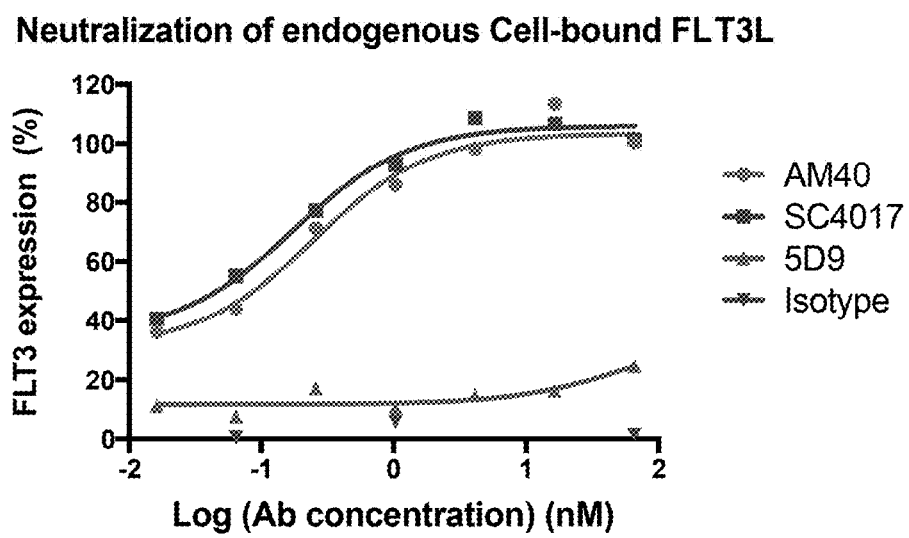

Finally, we confirmed both clones could neutralize endogenous FLT3L on the cell surface by developing an assay using primary T cells stimulated with 20 ng/ml IL-7 for 7 days (found to be the most effective protocol for inducing cell-surface FLT3L expression on primary T cells) in co-culture with FLT3+RS4;11. Briefly, IL-7 stimulated CD4+ T cells were incubated with RS4;11 cells overnight at a ratio of 15:1 (dose ratio response shown in FIG. 13A), either alone or in the presence of serial dilution of candidate clones, SC4017 and AM40. FLT3 downregulation was measured by flow cytometric methods as described previously. Both clones were shown to completely prevent FLT3 downregulation on RS4;11 cells at concentrations above 1 nM (FIG. 13B) with similar efficacy.

Example No. 12. Neutralizing FLT3L in Healthy Non-Human Primates

To determine safety and persistence of AM40 in neutralizing FLT3L, a toxicity study was performed over a period of one month using once-weekly repeat dosing. An eight week treatment follow-up period was included to follow animal progress. The study outline is depicted in FIG. 14. As shown in FIG. 15A, free soluble FLT3L levels dropped precipitously after the first administration of AM40 at all doses, but at 0.3 mg/kg was insufficient to maintain target engagement for the full week. The higher dosage groups (1 mg/kg and 30 mg/kg) exhibited complete target engagement (reflected as free soluble FLT3L below BLQ) consistently through day 57, at which point soluble FLT3L levels returned to baseline in the 1.0 mg/kg group.

Figure 15B:
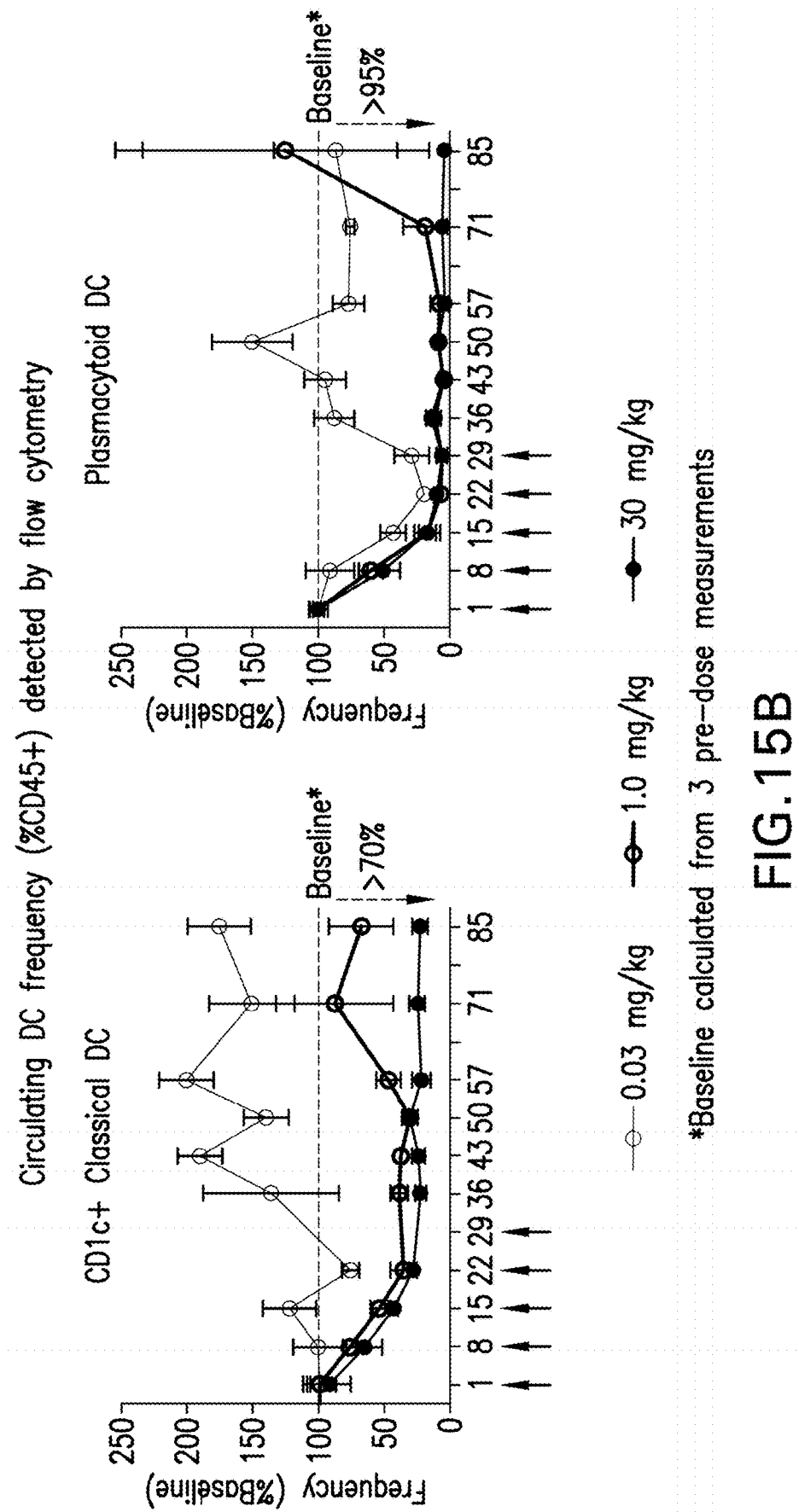

Similarly, measuring circulating DC frequency (% total CD45+ cells detected by via flow cytometry and expressed as a percentage of pre-study baseline levels) revealed a steady decline in CD1c+(classical) DC and plasmacytoid DC frequency through day 22 in the 1.0 and 30 mg/kg groups (FIG. 15B). Circulating CD1c+DC frequency remained suppressed through day 50 and day 85 for the 1 mg/kg group and 30 mg/kg group respectively. Circulating pDC frequency remained reduced through day 71 and day 85 for the 1 mg/kg group and 30 mg/kg group respectively. The return of DC populations in the 1.0 mg/kg group correlated with the return of free serum FLT3L which occurred at some point between days 57 and 85. These results indicate that DC populations drop when FLT3L is neutralized by AM40 but return to baseline rapidly when free FLT3L becomes available.

Example No. 13. FLT3L Expression Correlates with Severity of Systemic Lupus Erythematosus (SLE)

SLE is an autoimmune disease characterized by chronic inflammation and can affect almost any organ in the body and all age groups. SLE commonly affects joints, skin, kidneys, lungs, heart, and the brain. Given its role in proinflammatory signaling, the expression of FLT3L in individuals with SLE was investigated to look for correlations between FLT3L levels and disease severity. Published studies to date have relied largely on serum FLT3L levels when deriving correlations with disease and while this is the most practical measurement in clinical settings, it has the inherent disadvantage of being a reflection of production minus what is taken up by DC and other activated FLT3L-consuming cells. In inflammatory settings the number of FLT3-expressing cells and their consumption of FLT3L will vary greatly and this is likely explains the variations in findings between studies and why none have shown direct correlations between serum FLT3L and clinical scores of disease progression. Knowing that T cells are one of the predominant sources of FLT3L in the inflammatory setting, we developed an assay to measure FLT3L expression directly on the T cell surface using freshly isolated peripheral blood mononuclear cells (PBMC).

Serum and PBMC were isolated from individuals with SLE (n=24) and healthy donors (HD; n=15). Serum FLT3L was measured with ELISA (R&D Systems) as per the manufacturer's instructions and the frequency of FLT3L-expressing CD4+ T cells was determined using flow cytometric analysis developed in-house, with FLT3L detected with fluorescently labeled anti-FLT3L clone, MAB608 (R&D Systems). The SLE Disease Activity Index (SLEDAI) was used to determine lupus activity in the same individuals. Significance was determined using Mann Whitney and Spearman Correlation for comparison of healthy versus disease cohorts and correlations with SLEDAI respectively.

Figure 16A:
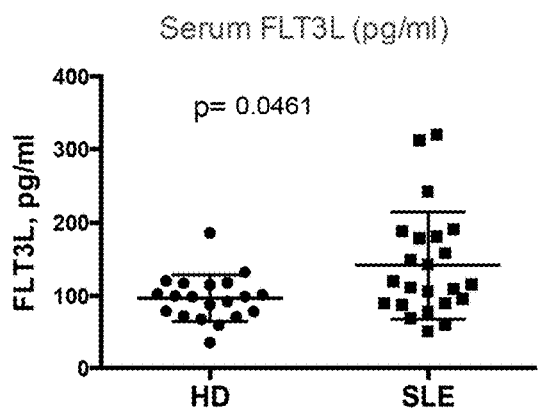
FIGS. 16A-16D. Measurement of FLT3L-expression and SLEDAI score correlation in SLE patients comparing serum measurement and flow cytometric analysis of T cells.
Figure 16B:
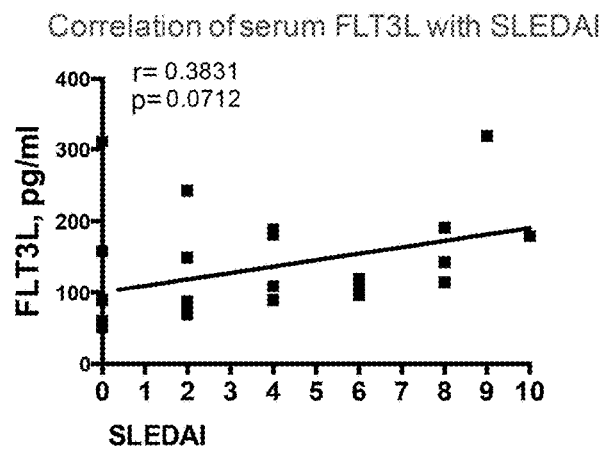
Figure 16C:
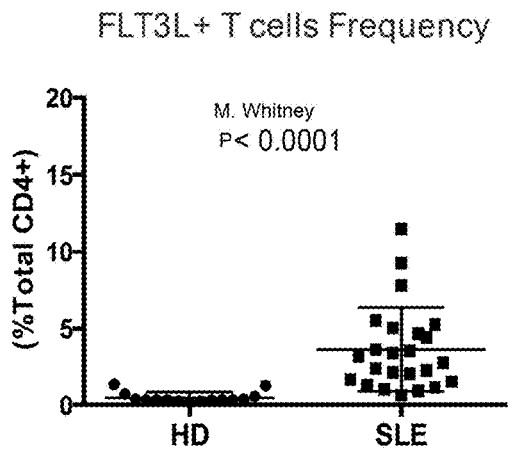
Figure 16D:
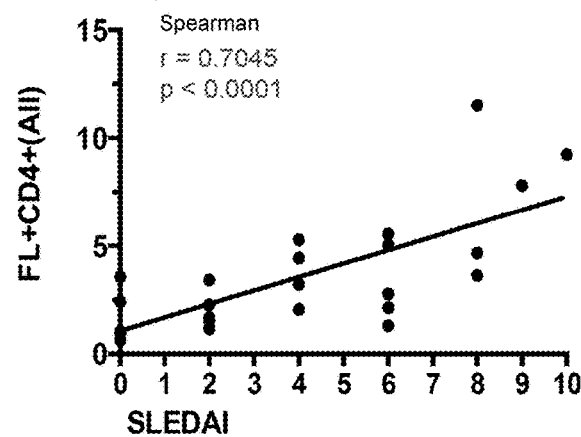

Consistent with previous literature, serum FLT3L levels were elevated in SLE donors compared with HD (p<0.05; FIG. 16A) but no significant correlation was found with disease activity (SLEDAI) (p<0.07; FIG. 16B). By contrast, when FLT3L production was measured by the frequency of FLT3L expressing CD4+ T cells, there was a highly significant increase SLE donors compared to HD (p<0.0001; FIG. 16C) and a strong correlation with SLEDAI scores (r=0.7045; p<0.0001; FIG. 16D). This data suggests that measuring FLT3L expression on T cells may be particularly relevant in the disease setting.

Upon finding of a correlation between SLEDAI scores and FLT3L expressing CD4+ T cells, subsets of CD4+ cell were examined to determine if (1) FLT3L expression across CD4+T cell subsets from SLE patients was consistent with known biology and (2) if subset expression correlates with SLEDAI scores. CD4+ subsets studied were naive T cells ($T_{naive}$), effector memory cells ($T_{EM}$), and central memory ($T_{CM}$) cells. The same protocols and significance levels, as described above, were used to study expression and correlations.

Figure 17A:
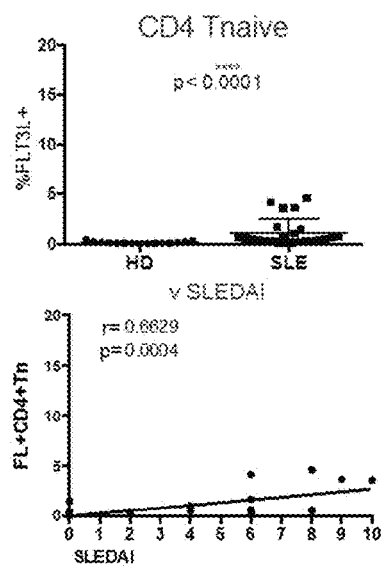
FIGS. 17A-17C. FLT3L expression in CD4+ T cell subsets and SLEDAI scores.
Figure 17B:
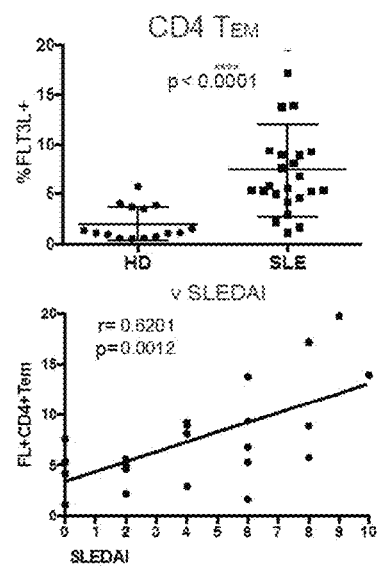
Figure 17C:
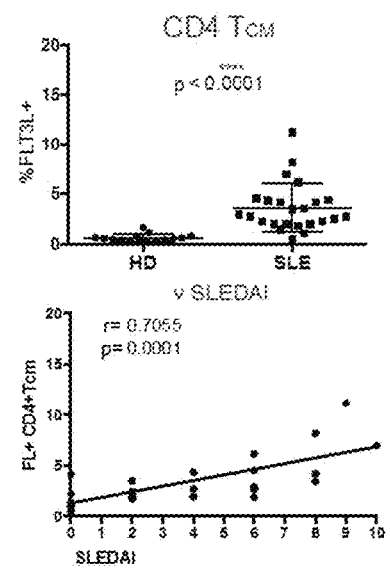

FLT3L expression across the CD4+ T cell subsets was consistent with the known biology of FLT3L expression. Specifically, FLT3L expression was generally not observed on $T_{naive}$ cells in HD, though there was a small, but significant elevation in SLE donors (FIG. 17A, Top). FLT3L expression on $T_{naive}$ cells from SLE donors was significantly correlated with SLEDAI scores (FIG. 17A, Bottom; r=0.6629; p=0.0004). Importantly, FLT3L expression was observed on both HD and SLE CD4+ $T_{EM}$, as would be expected in this population that captures recently activated T cells that would have been exposed to □-chain cytokines known to induce FLT3L expression. Although this response was seen in both HD and SLE donors, it was significantly elevated in the latter and again, expression in SLE donors correlated with SLEDAI (FIG. 17B, Bottom; r=0.6201; p=0.0012). Finally, FLT3L expression declines in healthy CD4+ T cells as they differentiate from $T_{EM}$ to $T_{CM}$, but is maintained in the PBMC of SLE donors (FIG. 17C, Top; p<0.0001). Again, a significant correlation exists between the frequency of FLT3L+ T cells and SLEDAI, suggesting that expression in this group is a reflection of the chronic inflammatory state Collectively, these studies demonstrate that FLT3L expression on CD4+ T cells of SLE patients is significantly increased compared to those of HD. Moreover, the increased FLT3L expression is highly correlated with SLEDAI scores. Thus, administration of anti-FLT3L antibodies to SLE patients is a reasonable therapeutic strategy for reducing FLT3L-expressing T cell populations to reduce inflammation in SLE patients.

The method used above was validated using PrimeFlow in situ detection of IC FLT3L RNA and confirmed using APC-conjugated AM40.

Example No. 14. FLT3L Expression in Myositis

Myositis is chronic muscle inflammation that is characterized by weakness, swelling, and muscle pain. At the cellular level, myositis is characterized by elevated levels of interferon type 1 proteins and pDCs. Myositis can be associated with SLE and other proinflammatory conditions. Therefore, the expression of FLT3L in individuals with myositis was investigated to look for correlations between FLT3L levels and disease severity.

PBMC from individuals with myositis and HD were studied for FLT3L expressing CD4+ T cells using FACS. CD4+ T cells were divided into $T_{naive}$, $T_{EM}$, and $T_{CM}$ subsets. Significance between myositis and HD samples was determined using Mann Whitney analysis.

Figure 18A:
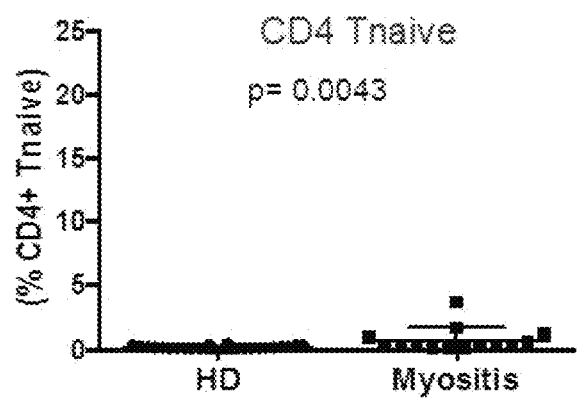
FIGS. 18A-18C. FLT3L expression in PBMC CD4 subsets from individuals with myositis.
Figure 18B:
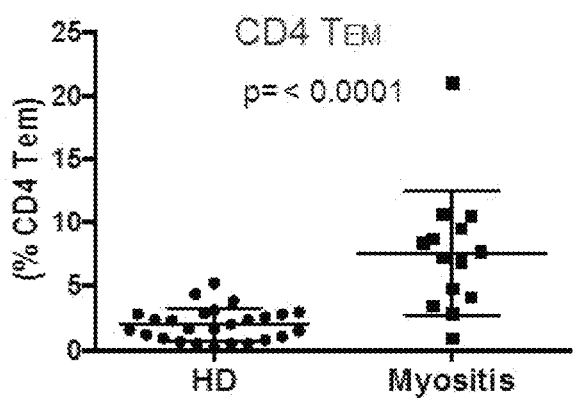
Figure 18C:
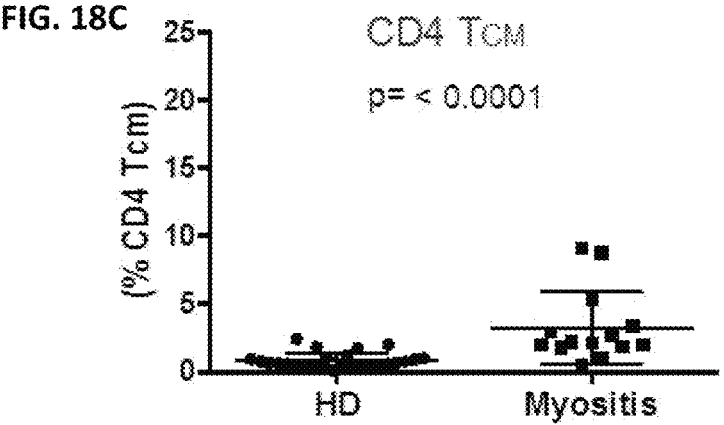

As seen in FIGS. 18A and 18B, the expression of FLT3L in PBMCs from individuals with myositis parallel the findings from SLE patients, as they were characterized by significant increases in the percentage of CD4+ T cells positive for FLT3L ($T_{naive}$ (p<0.05; FIG. 18A), $T_{EM}$ (p<0.0001; FIG. 18B), and $T_{CM}$ (p<0.0001; FIG. 18C)). In light of these results, administration of anti-FLT3L antibodies to myositis patients is a reasonable therapeutic strategy for reducing FLT3L-expressing T cell populations to reduce inflammation in myositis patients.

Example No. 15. FLT3L Expression in Nephritis

Nephritis is an immune disorder that affects the kidneys and associated renal structures. The condition can originate from SLE, certain toxins, or certain infections. Nephritis can result in permanent loss of kidney function, which can be fatal. Dendritic cells have been shown to infiltrate the kidney in lupus nephritis (Fiore et al., (2008) Mol Immunology v45: 259-265) and are thought to play a role in driving inflammation in the kidney, thus, it was hypothesized that FLT3L blockade could suppress DC and prevent progressive loss of kidney function.

Figure 19A:
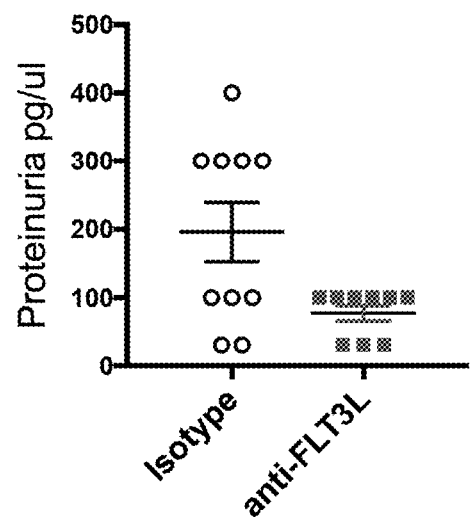
FIGS. 19A-19B. Proteinuria and nephritis scores in MRL mice.
Figure 19B:
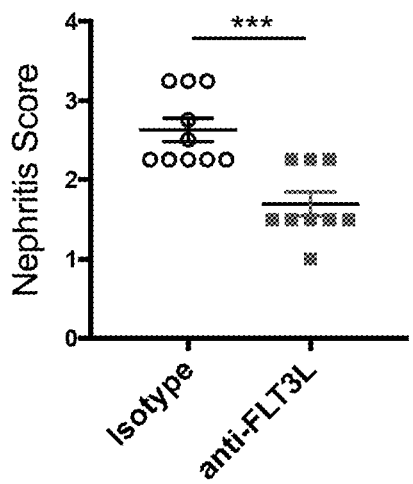

The Murphy Roths Large/lymphoproliferative (MRL.lpr) nephritis mouse model and a mouse surrogate anti-FLT3L antibody (LFC-1) were used to study the effects of FLT3L blockade on proteinuria levels and nephritis score. An isotype control was included, as well as an anti-IFNAR antibody treatment group. Mice administered anti-FLT3L antibody exhibited significant reductions in proteinuria at 17 weeks post-administration (FIG. 19A). In addition, nephritis scores at 18 weeks were reduced in mice administered anti-FLT3L antibody compared to isotype controls (FIG. 19B). Importantly, proteinuria and nephritis scores in mice administered anti-FLT3L antibody were reduced compared to mice administered. These results support a role for FLT3L-mediated inflammation in nephritis. In light of these results, administration of anti-FLT3L antibodies to nephritis patients is a reasonable therapeutic strategy for reducing FLT3L-expressing T cell populations to reduce inflammation in nephritis patients.

Figure 20A:
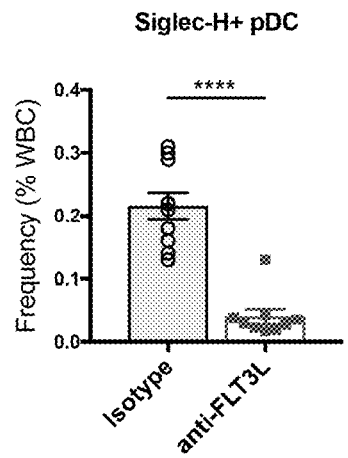
FIGS. 20A-20C. Splenic dendritic populations in MRL mice.
Figure 20B:
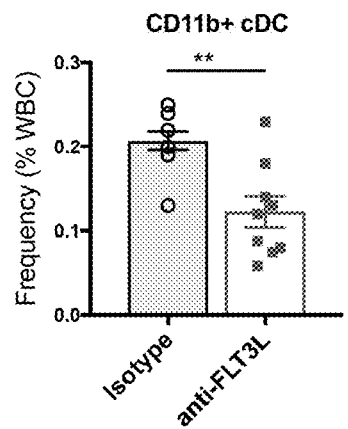
Figure 20C:
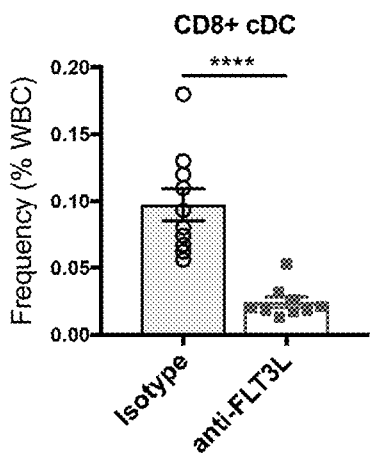

Splenic DC populations were also examined to provide insights into FLT3L-associated changes in white blood cell populations in nephritis. The spleen was harvested from MRL mice at 18 weeks and changes in splenic DC populations were examined. Anti-FLT3L antibody treatment significantly reduced circulating DCs in MRL mice (FIG. 20A-C). Specifically Siglec-H+-pDC were significantly reduced compared to isotype controls after anti-FLT3L antibody administration (FIG. 20A). Similarly, significant reductions were observed in CD11b+ cDCs (equivalent to human CD1c+DC) and CD8+ cDCs (equivalent to human CD141+DC) (FIGS. 20B and 20C). Further, no incidences of dermatitis in anti-FLT3L treated mice were observed compared to the usual occurrence of 30-40% in mice without treatment. Therefore, anti-FLT3L antibody treatment reduced circulating DC populations and improved secondary pathology (dermatitis) in a nephritis model. In light of these results, administration of anti-FLT3L antibodies to nephritis patients may reduce inflammation and tissue damage by suppressing DC populations.

Example No. 16. FLT3L Expression in SjöGren's Syndrome

Primary Sjögren's syndrome (pSS) is an autoimmune condition characterized by extensive dryness of the eyes and salivary glands. In addition, the condition can cause multi-organ dysfunction. The syndrome occurs alone or in the presence of additional autoimmune diseases such as lupus or rheumatoid arthritis. Serum levels of FLT3L are increased in individuals with pSS and there is evidence of local expression of both FLT3L and its receptor in the inflamed salivary gland (Tobon et al., (2010) Arthritis and Rheumatism v62: 344).

Figure 25B:
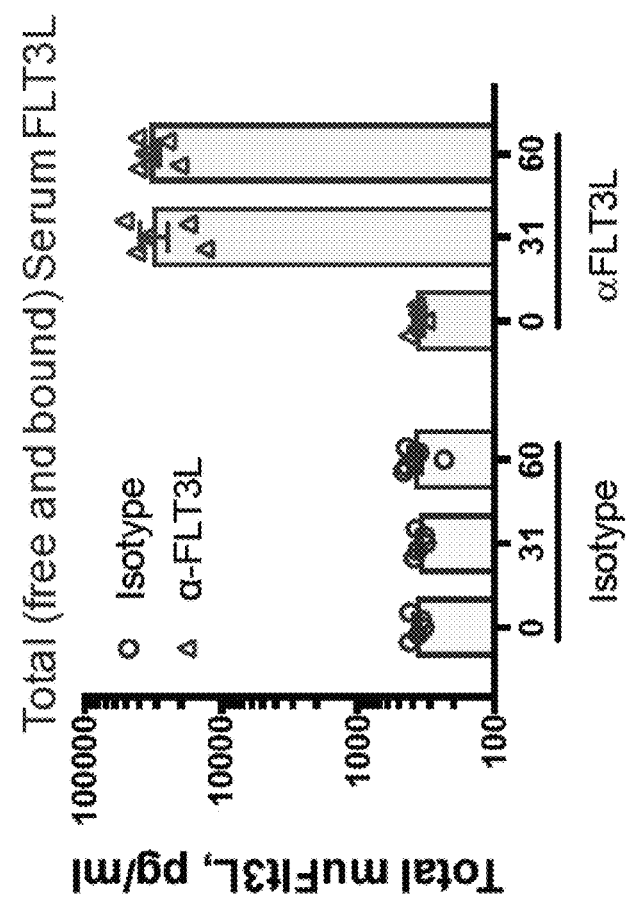
FIGS. 25A-25B. Anti-FLT3L monoclonal antibody (LFC-1) effectively neutralizes FLT3L throughout the course of treatment and results in an accumulation of circulating drug/ligand complex.
Figure 25A:
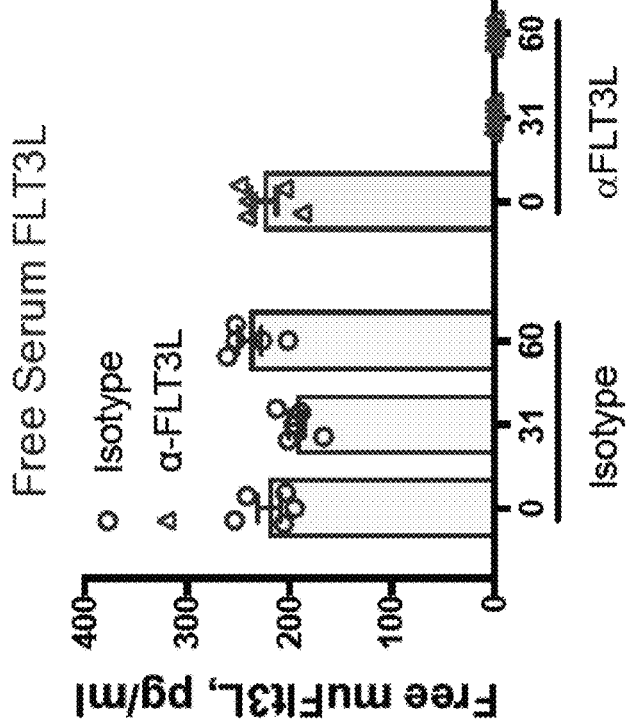
Figure 26A:
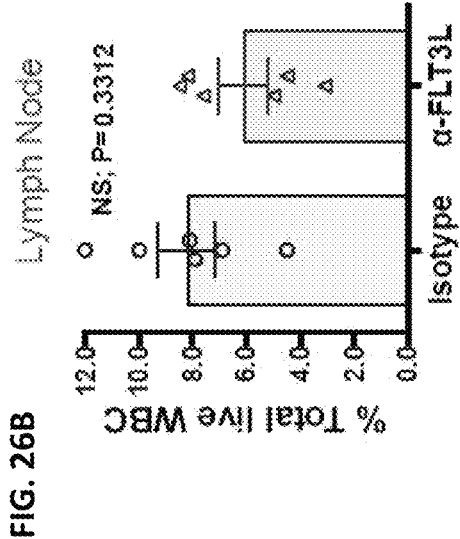
FIGS. 26A-26D. Blockade of FLT3L suppresses T cell activation in the spleen and SG-draining lymph node (LN) of aged NOD-$H2^{h4}$ mice. FLT3L blockade with an anti-FLT3L monoclonal antibody (LFC-1) leads to a reduction in antigen experienced $CD44^{HI}$ CD4+ and CD8+ T cell frequency in spleen and salivary gland-draining LN (at the end of the study at 24-26 weeks of age). The bar graphs are derived from flow cytometric analysis of spleen and draining LN. Each bar represents the average +/- standard error of the mean (SEM) of n=4-5 mice.
Figure 26B:
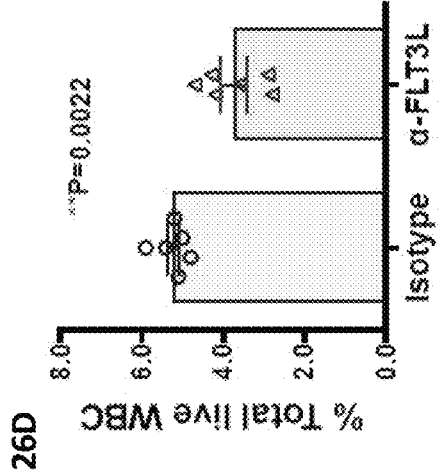
Figure 26C:
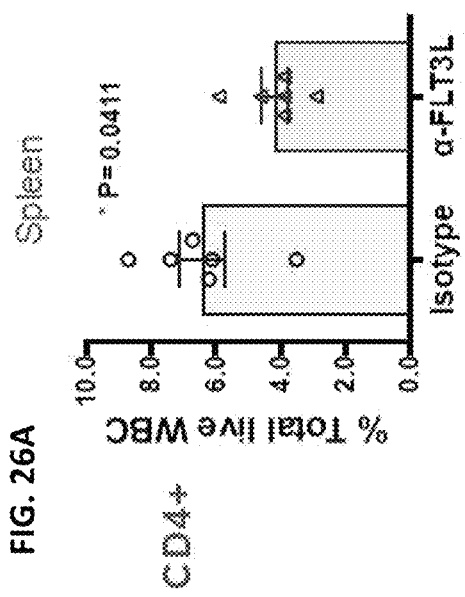
Figure 26D:
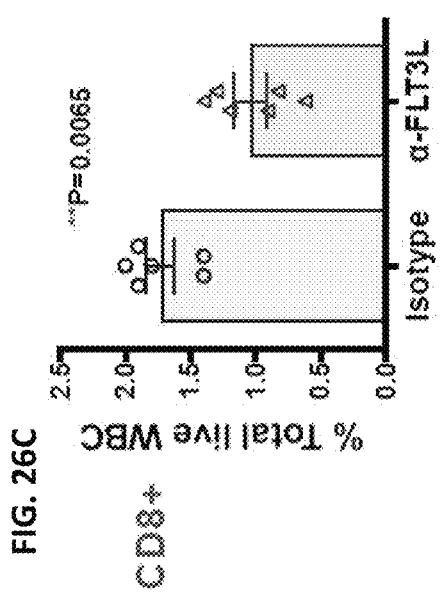

A NOD.H2h4 Sjögren's mouse model was used to study salivary gland pathology following prolonged anti-FLT3L antibody (LFC-1) treatment. By 16 weeks of age, these mice develop tertiary lymphoid structures (TLS) in the salivary gland (SG) which comprise largely of DCs, B220+B cells and CD3+ T cells, in a manner that closely resembles pathological changes seen in humans. This tissue damage is preceded by the development of autoantibodies and the formation of spontaneous germinal centers in the spleen (Mahmoud et al., 2016 Science Translational Medicine, v8 361ra137). Mice were treated using either a prophylactic (commencing at 5 weeks of age) or therapeutic (commencing at 17 weeks of age) protocol with isotype IgG controls (5 mg/kg), an anti-FLT3L antibody (5 mg/kg). For both protocols, treatment continued with twice weekly dosing until end of study (26 weeks). Anti-FLT3L monoclonal antibody (LFC-1) effectively neutralized FLT3L throughout the course of treatment (FIG. 25A) and resulted in an accumulation of circulating drug/ligand complex (FIG. 25B).

Figure 27:
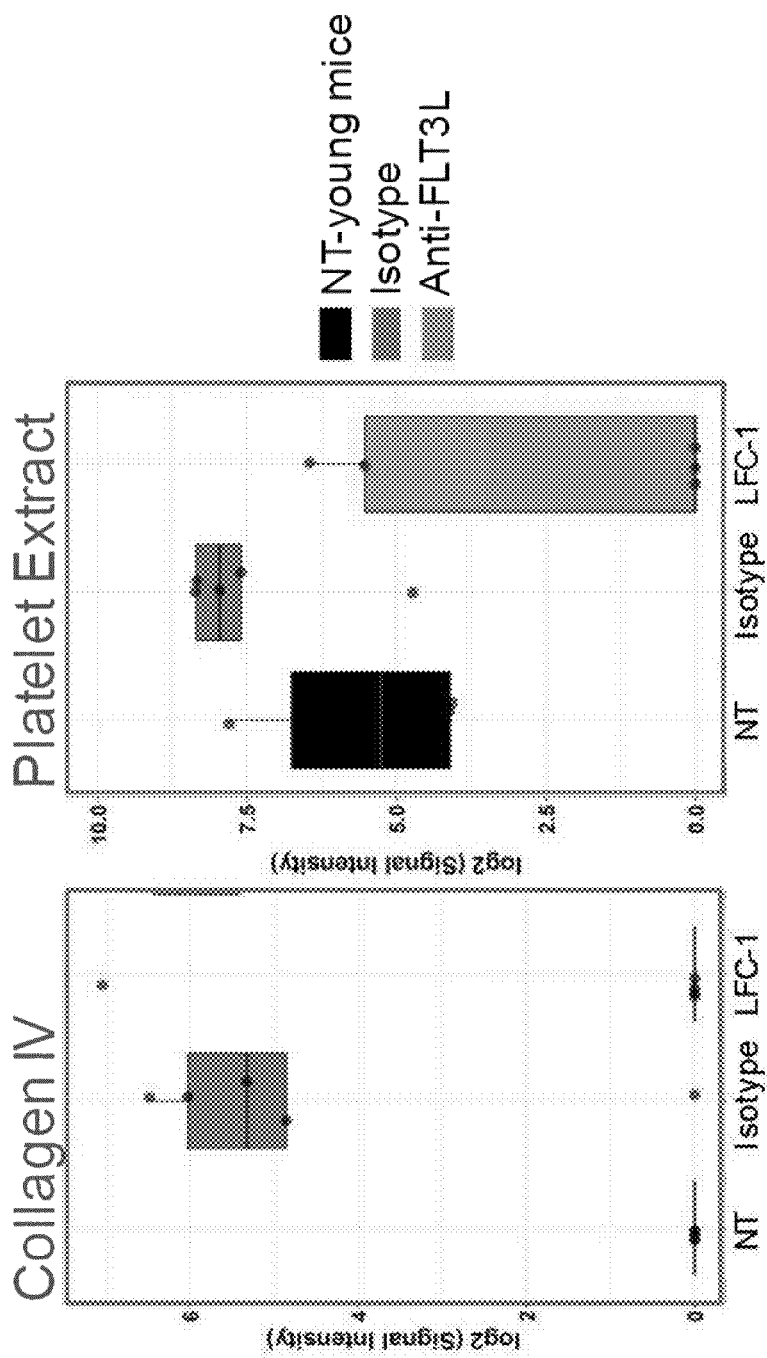
FIG. 27. Therapeutic anti-FLT3L blockade selectively reduces two serum IgG autoantibody specificities. Corresponding serum samples were measured by UTSW IgG autoantibody analysis.

Lymphoid organs were collected to evaluated changes to peripheral immune cell populations and salivary glands (SG) were harvested and evaluated for tissue pathology (TLS frequency). While it's been previously reported that prophylactic treatments may prevent disease onset, there have been limited previous reports that tissue damage could be delayed or prevented by therapeutic intervention after disease onset. Anti-FLT3L monoclonal antibody (LFC-1) reduced antigen experienced $CD44^{HI}$ CD4+ and CD8+ T cell frequency in spleen and salivary gland-draining LN (at the end of the study at 24-26 weeks of age) (FIGS. 26A-26D), as well as selectively reduced specific autoantibodies to collagen IV and platelet extract (FIG. 27).

Figure 21A:
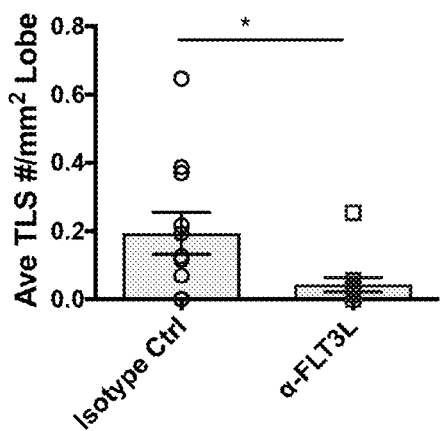
FIGS. 21A and 21B. Salivary gland pathology score in NOD.H2h4 Sjögren's Syndrome mouse model.
Figure 21B:
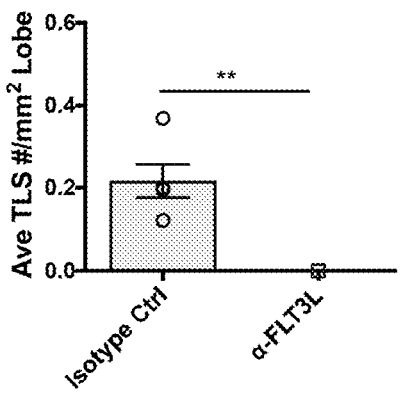
Figure 22A:
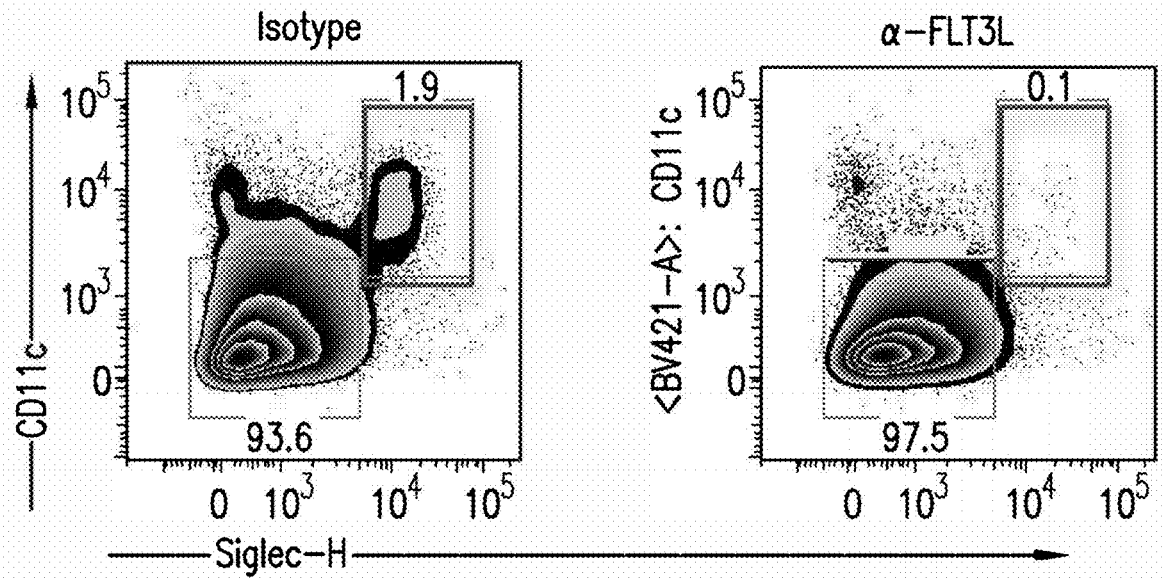
FIGS. 22A-22D. Changes in dendritic cell presence after anti-FLT3L antibody administration.
Figure 22B:
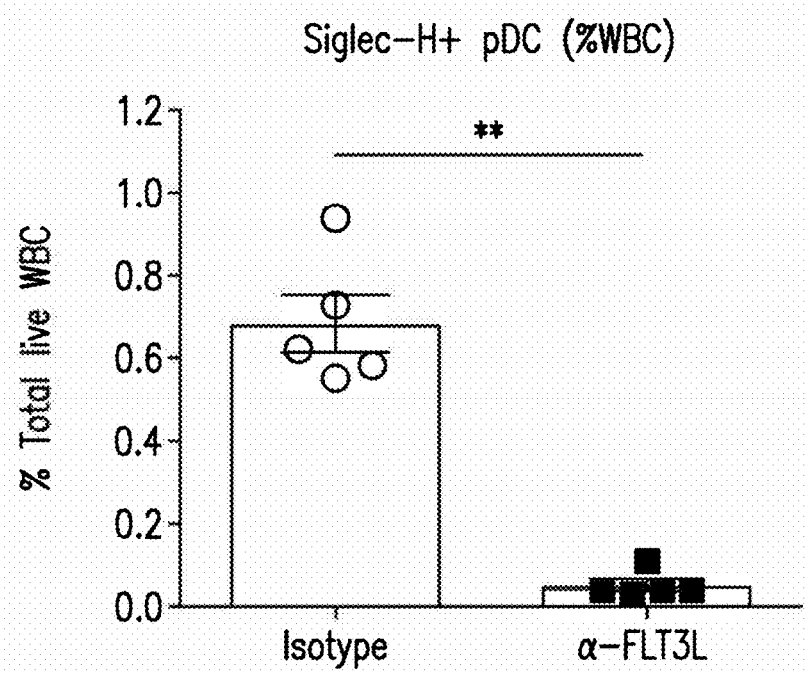
Figure 22C:
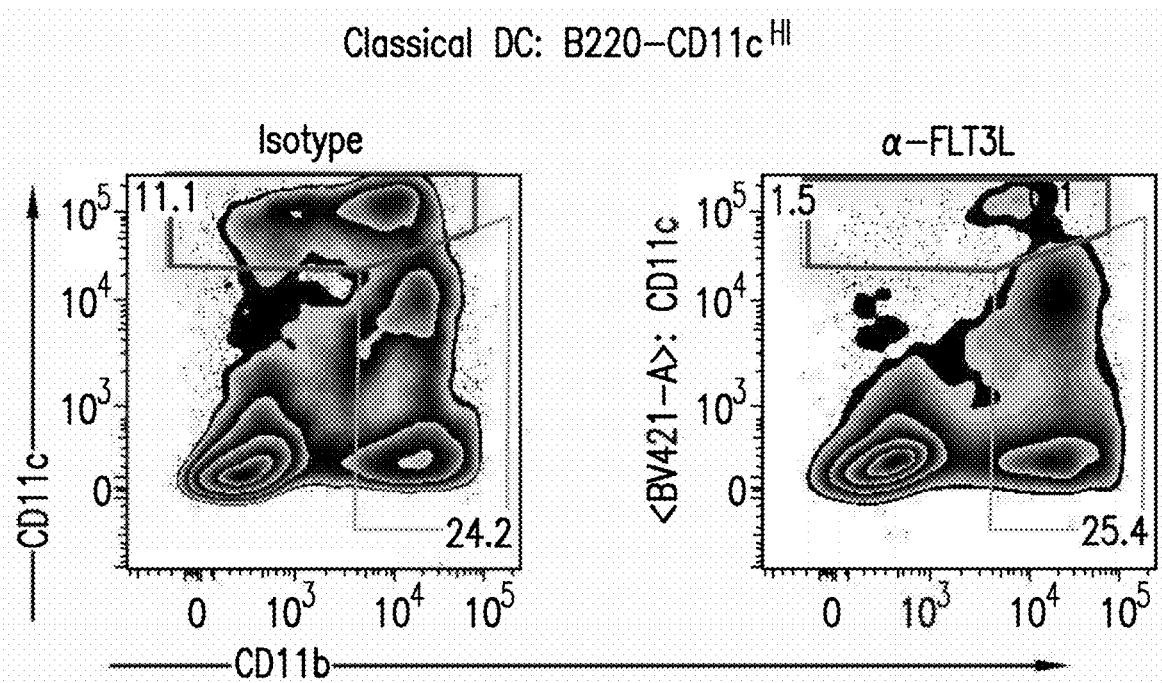
Figure 22D:
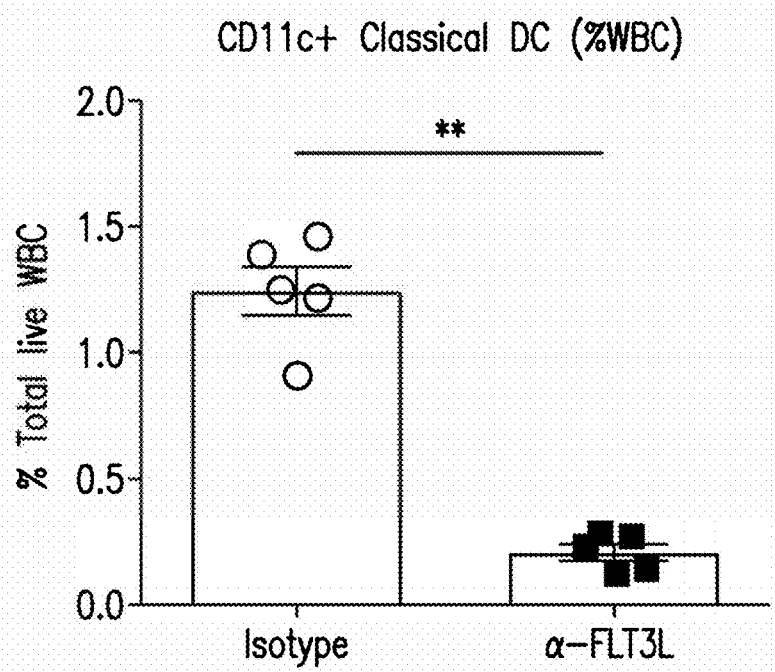
Figure 23C:
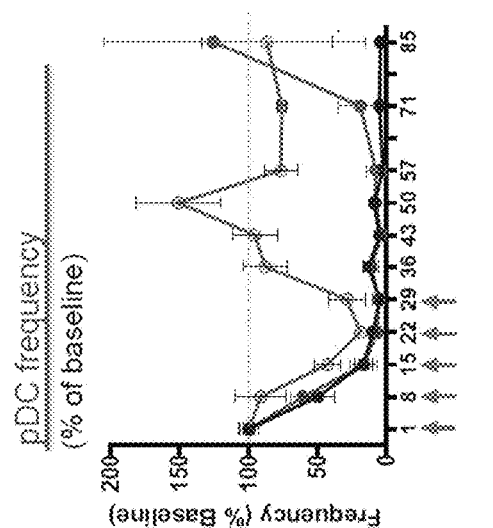
FIGS. 23A-23C. Anti-FLT3L antibody (MEDI1116) PK in cynomolgus monkeys correlates with functional neutralization of FLT3L, confirmed by the suppression and return of pDCs. As indicated by the arrows, anti-FLT3L antibody (MEDI1116) was administered to cynomolgus monkeys once a week at days 1, 8, 15, 22, 29.
Figure 23B:
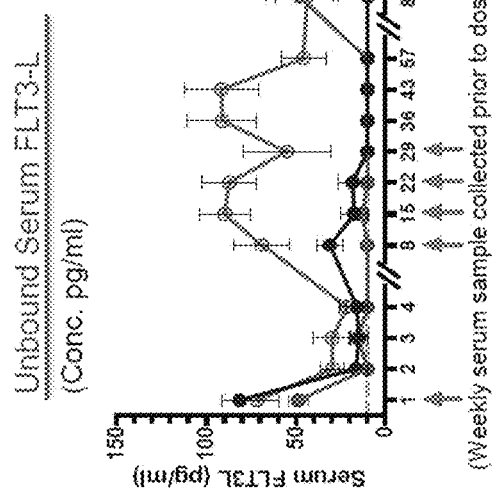
Figure 23A:
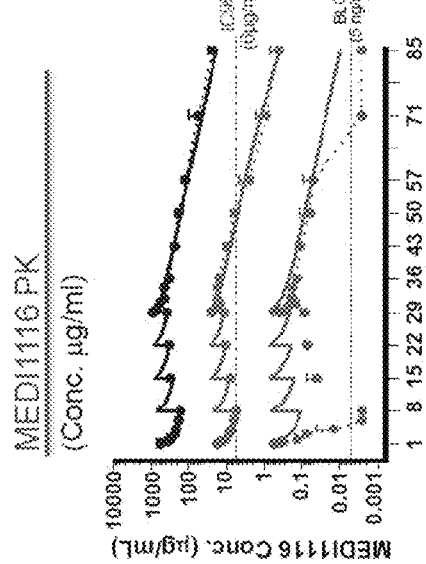

As expected, animals treated with isotype control IgG had increased TLS formation in the salivary gland (measured as frequency per $mm^2$ tissue) by 26 weeks of age, indicative of salivary gland damage. Mice treated with anti-FLT3L, even when dosed therapeutically, had a significant reduction in tissue SG damage (FIG. 21A) and disease was prevented completely when dosed prophylactically (FIG. 21B). DC populations, as measured in the spleen, were significantly suppressed, though not deleted entirely (FIGS. 22A-D). None-the-less, this was sufficient to make a significant impact on disease onset and progression by reducing inflammatory infiltration into the salivary gland. These results support that inflammation in pSS is driven by FLT3L-mediated mechanisms. In light of these results, administration of anti-FLT3L antibodies is a reasonable therapeutic strategy for treating pSS in human subjects.

From the foregoing description, it will be apparent that variations and modifications may be made to the disclosure described herein to adopt it to various usages and conditions. Such embodiments are also within the scope of the following claims. The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof. All patents and publications mentioned in this specification are herein incorporated by reference to the same extent as if each independent patent and publication was specifically and individually indicated to be incorporated by reference.

---

What is claimed is:

1. A method of treating an autoimmune disease, comprising administering to a subject in need thereof a pharmaceutically effective amount of a human monoclonal antibody that comprises:
   (1) a heavy chain comprising: (i) a variable region (VH) that comprises the amino acid sequence of SEQ ID NO:1, and (ii) a human IgG1 heavy chain constant domain; and
   (2) a light chain comprising: (i) a variable region (VL) that comprises the amino acid sequence of SEQ ID NO:2, and (ii) a human lambda light chain constant domain.

2. The method of claim 1, wherein said heavy chain comprises the amino acid sequence of SEQ ID NO:61, and said light chain comprises the amino acid sequence of SEQ ID NO: 62.

3. The method of claim 1, wherein said autoimmune disease is associated with increased level of FLT3L-expressing CD4+ T cells.

4. The method of claim 1, wherein said autoimmune disease is systemic lupus erythematosus (SLE).

5. The method of claim 1, wherein said autoimmune disease is Sjögren's syndrome.

6. The method of claim 1, wherein said autoimmune disease is rheumatoid arthritis.

7. The method of claim 1, wherein said autoimmune disease is nephritis.

8. The method of claim 1, wherein said autoimmune disease is multiple sclerosis.

9. The method of claim 1, wherein said autoimmune disease is psoriasis.

10. The method of claim 1, further comprising administering to said subject a second immunoregulatory agent.

11. A human monoclonal antibody comprising:
   (1) a heavy chain comprising: (i) a variable region (VH) that comprises the amino acid sequence of SEQ ID NO:1, and (ii) a human IgG1 heavy chain constant domain; and
   (2) a light chain comprising: (i) a variable region (VL) that comprises the amino acid sequence of SEQ ID NO:2, and (ii) a human lambda light chain constant domain.

12. The antibody of claim 11, wherein said heavy chain comprises the amino acid sequence of SEQ ID NO:61, and said light chain comprises the amino acid sequence of SEQ ID NO: 62.

13. A pharmaceutical formulation comprising the antibody of claim 11, further comprising a pharmaceutically acceptable excipient.

14. The pharmaceutical formulation of claim 13, wherein said excipient comprises a surfactant, a stabilizer, an isotonic agent, a buffer, or any combination thereof.

15. A nucleic acid encoding a human monoclonal antibody, said antibody comprises:
   (1) a heavy chain comprising: (i) a variable region (VH) that comprises the amino acid sequence of SEQ ID NO:1, and (ii) a human IgG1 heavy chain constant domain; and
   (2) a light chain comprising: (i) a variable region (VL) that comprises the amino acid sequence of SEQ ID NO:2, and (ii) a human lambda light chain constant domain.

16. The nucleic acid of claim 15, wherein said heavy chain comprises the amino acid sequence of SEQ ID NO:61, and said light chain comprises the amino acid sequence of SEQ ID NO: 62.

17. A host cell comprising the nucleic acid of claim 15.

18. The host cell of claim 17, wherein said host cell is a Chinese hamster ovary (CHO) cell or a HEK293 cell.

19. A method of making the antibody of claim 11, comprising (a) culturing a host cell expressing said antibody; and (b) isolating said antibody from said cultured host cell.

\* \* \* \* \*